(12) United States Patent
Bayley et al.

(10) Patent No.: US 11,213,797 B2
(45) Date of Patent: Jan. 4, 2022

(54) DROPLET ASSEMBLY BY 3D PRINTING

(71) Applicant: Isis Innovation Limited, Oxford (GB)

(72) Inventors: John Hagan Pryce Bayley, Oxford (GB); Gabriel Villar, Oxford (GB); Alexander D. Graham, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 546 days.

(21) Appl. No.: 14/649,394

(22) PCT Filed: Dec. 6, 2013

(86) PCT No.: PCT/GB2013/053229
§ 371 (c)(1),
(2) Date: Jun. 3, 2015

(87) PCT Pub. No.: WO2014/087175
PCT Pub. Date: Jun. 12, 2014

(65) Prior Publication Data
US 2016/0136888 A1    May 19, 2016

(30) Foreign Application Priority Data

Dec. 7, 2012   (GB) .................................... 1222052

(51) Int. Cl.
*B29C 64/112*  (2017.01)
*A61K 9/127*   (2006.01)
(Continued)

(52) U.S. Cl.
CPC ............... *B01J 13/04* (2013.01); *A61K 9/127* (2013.01); *A61K 9/1277* (2013.01);
(Continued)

(58) Field of Classification Search
CPC ......... B33Y 10/00; B33Y 30/00; B29C 64/00; B01L 3/0268; A61K 9/127; A61K 9/1277
See application file for complete search history.

(56) References Cited

U.S. PATENT DOCUMENTS 4,812,856 A * 3/1989 Wallace .................. B41J 2/175
118/610
4,934,564 A * 6/1990 Piatt ...................... B01L 3/0268
222/14
(Continued)

FOREIGN PATENT DOCUMENTS

CA   2 564 120 A1   8/1998
EP   1 707 965 A1   10/2006
(Continued)

OTHER PUBLICATIONS

Bayley et al., "Droplet interface bilayers," Mol. Biosystems, Dec. 2008, 4(12), pp. 1191-1208 (Year: 2008).*
(Continued)

*Primary Examiner* — Matthew J Daniels
*Assistant Examiner* — Andrew D Graham
(74) *Attorney, Agent, or Firm* — Hamilton, Brook, Smith & Reynolds, P.C.

(57) ABSTRACT

The invention relates to an apparatus for producing a droplet assembly, which apparatus comprises a droplet generator. A process for producing a droplet assembly, using an apparatus comprising a droplet generator is also described. The invention also relates to droplet assemblies comprising a plurality of droplets. Various uses of the droplet assemblies are also described.

29 Claims, 16 Drawing Sheets

Fig. 2b

(51) Int. Cl.
*B01J 13/04* (2006.01)
*B01L 3/02* (2006.01)
*C09B 67/02* (2006.01)
*C09B 57/00* (2006.01)
*B29C 69/00* (2006.01)
*B33Y 10/00* (2015.01)
*B33Y 30/00* (2015.01)
*B33Y 50/02* (2015.01)
*B33Y 80/00* (2015.01)
*B29K 105/00* (2006.01)
*B29L 31/00* (2006.01)

(52) U.S. Cl.
CPC .......... *B01L 3/0268* (2013.01); *B29C 64/112* (2017.08); *B29C 69/00* (2013.01); *C09B 57/001* (2013.01); *C09B 67/0097* (2013.01); *B01L 2300/0819* (2013.01); *B01L 2400/0433* (2013.01); *B29K 2105/0058* (2013.01); *B29L 2031/753* (2013.01); *B33Y 10/00* (2014.12); *B33Y 30/00* (2014.12); *B33Y 50/02* (2014.12); *B33Y 80/00* (2014.12)

(56) References Cited

U.S. PATENT DOCUMENTS

| | | | | |
|---|---|---|---|---|
| 5,464,629 | A * | 11/1995 | Monshipouri | A61K 9/127 424/450 |
| 5,858,399 | A | 1/1999 | Lanza | |
| 5,925,511 | A * | 7/1999 | Fuhr | A01N 1/02 435/1.3 |
| 6,531,156 | B1 * | 3/2003 | Clark | A61K 9/5026 424/489 |
| 6,713,021 | B1 * | 3/2004 | Shvets | B01L 3/0265 137/487.5 |
| 6,962,747 | B1 * | 11/2005 | Sasaki | A61K 47/6911 424/1.21 |
| 6,995,024 | B2 * | 2/2006 | Smith | B01L 3/0244 222/57 |
| 7,217,410 | B2 * | 5/2007 | Suslick | A61K 49/001 424/1.11 |
| 8,268,627 | B2 | 9/2012 | Bayley et al. | |
| 8,562,807 | B2 * | 10/2013 | Srinivasan | B01L 3/0268 204/600 |
| 8,784,929 | B2 | 7/2014 | Wallace et al. | |
| 8,992,984 | B1 | 3/2015 | Brinker et al. | |
| 9,223,317 | B2 * | 12/2015 | Winger | G05D 7/0629 |
| 9,831,010 | B2 | 11/2017 | Bayley et al. | |
| 10,548,852 | B2 | 2/2020 | Bayley et al. | |
| 10,950,376 | B2 | 3/2021 | Bayley et al. | |
| 10,978,218 | B2 | 4/2021 | Baylet et al. | |
| 2001/0051334 | A1 * | 12/2001 | Barth | B01J 19/0046 435/6.1 |
| 2002/0106308 | A1 * | 8/2002 | Zweifel | B01L 3/0262 422/400 |
| 2003/0035842 | A1 | 2/2003 | Kazakov et al. | |
| 2003/0048341 | A1 * | 3/2003 | Mutz | B01J 19/0046 506/12 |
| 2003/0119193 | A1 * | 6/2003 | Hess | B01F 5/0085 436/44 |
| 2003/0128267 | A1 * | 7/2003 | Teung | B01L 3/0265 347/112 |
| 2004/0191518 | A1 | 9/2004 | Naito et al. | |
| 2004/0237822 | A1 * | 12/2004 | Boland | B01L 3/0268 101/483 |
| 2005/0056713 | A1 * | 3/2005 | Tisone | B01D 19/0047 239/690 |
| 2006/0210443 | A1 * | 9/2006 | Steams | B01L 3/0268 422/400 |
| 2007/0120280 | A1 * | 5/2007 | Anchordoquy | B01J 13/04 264/4.1 |
| 2007/0148697 | A1 * | 6/2007 | Delaney, Jr. | B01J 19/0046 435/7.1 |
| 2007/0243634 | A1 * | 10/2007 | Pamula | B01F 13/0071 436/518 |
| 2007/0248541 | A1 | 10/2007 | Tagawa et al. | |
| 2007/0275415 | A1 * | 11/2007 | Srinivasan | B01F 13/0071 435/7.4 |
| 2007/0293449 | A1 | 12/2007 | Cui et al. | |
| 2008/0017736 | A1 * | 1/2008 | Lee | B01L 3/0268 239/690.1 |
| 2008/0053205 | A1 | 3/2008 | Pollack et al. | |
| 2008/0063794 | A1 | 3/2008 | Krotz | |
| 2008/0153150 | A1 * | 6/2008 | Holden | C12M 35/00 435/287.1 |
| 2009/0012187 | A1 * | 1/2009 | Chu | A61K 9/113 516/54 |
| 2009/0074988 | A1 * | 3/2009 | Faris | B01J 19/00 427/596 |
| 2009/0131543 | A1 * | 5/2009 | Weitz | A61K 9/113 516/54 |
| 2009/0208466 | A1 * | 8/2009 | Yoo | C12N 5/0062 424/93.7 |
| 2009/0289213 | A1 | 11/2009 | Pipper et al. | |
| 2010/0032627 | A1 * | 2/2010 | Bayley | G01N 33/5432 252/408.1 |
| 2010/0147450 | A1 * | 6/2010 | Takeuchi | G01N 33/68 156/245 |
| 2010/0173394 | A1 * | 7/2010 | Colston, Jr. | B01F 3/0807 435/287.2 |
| 2010/0316696 | A1 * | 12/2010 | Wiggenhorn | A61K 9/1277 424/450 |
| 2011/0041978 | A1 * | 2/2011 | Wallace | G01N 33/5432 156/60 |
| 2011/0076734 | A1 | 3/2011 | Zhou et al. | |
| 2011/0250688 | A1 | 10/2011 | Hasan | |
| 2011/0305761 | A1 * | 12/2011 | Shum | A61K 9/1273 424/489 |
| 2011/0306539 | A1 * | 12/2011 | Shen | A61K 9/14 514/1.1 |
| 2011/0311408 | A1 * | 12/2011 | Azimi | B01L 3/5027 422/509 |
| 2012/0006681 | A1 * | 1/2012 | Kaier | B01F 3/0815 204/453 |
| 2012/0116568 | A1 * | 5/2012 | Murphy | B41J 3/407 700/118 |
| 2012/0220481 | A1 * | 8/2012 | Wallace | G01N 33/5432 506/9 |
| 2012/0322162 | A1 * | 12/2012 | Collier | B01F 13/0071 436/172 |
| 2013/0017564 | A1 * | 1/2013 | Guillemot | B01L 3/0268 435/8 |
| 2013/0319861 | A1 * | 12/2013 | Khandros | B81B 1/00 204/452 |
| 2014/0023697 | A1 * | 1/2014 | Dimauro | C30B 29/54 424/450 |
| 2014/0356289 | A1 | 12/2014 | Bayley et al. | |
| 2015/0248949 | A1 | 9/2015 | Bayley et al. | |
| 2015/0270043 | A1 | 9/2015 | Bayley et al. | |
| 2015/0285781 | A1 * | 10/2015 | Heron | B01D 69/122 436/89 |
| 2016/0136888 | A1 | 5/2016 | Bayley et al. | |
| 2018/0096751 | A1 | 4/2018 | Bayley et al. | |
| 2020/0214988 | A1 | 7/2020 | Bayley et al. | |

FOREIGN PATENT DOCUMENTS

| | | |
|---|---|---|
| EP | 2 253 378 | 11/2010 |
| GB | 1119032.9 | 7/1968 |
| JP | 2001-505224 | 4/2001 |
| JP | 2001-515853 | 9/2001 |
| JP | 2001-1515853 | 9/2001 |
| JP | 2010-503417 | 2/2010 |
| JP | 2010-222282 | 10/2010 |
| JP | 2010-536551 | 12/2010 |
| JP | 2012/166159 | 9/2012 |
| KR | 20120038662 | 4/2012 |
| WO | WO 1991/00084 A1 | 1/1991 |
| WO | WO 98/33483 | 8/1998 |
| WO | WO 99/12523 | 3/1999 |

(56) References Cited

FOREIGN PATENT DOCUMENTS

| WO | WO 2005/053643 A1 | 6/2005 | | |
|---|---|---|---|---|
| WO | WO 2006/096571 A2 | 3/2006 | | |
| WO | WO 2006/096571 A2 | 9/2006 | | |
| WO | WO 2007/010668 A1 | 1/2007 | | |
| WO | WO 2007/094739 A1 | 8/2007 | | |
| WO | WO 2007/0101174 A2 | 9/2007 | | |
| WO | WO 2008/012552 A1 | 1/2008 | | |
| WO | WO 2008/034180 A1 | 3/2008 | | |
| WO | WO 2009/024775 A1 | 2/2009 | | |
| WO | WO 2009/049089 A1 | 4/2009 | | |
| WO | WO 2009/148598 A1 | 12/2009 | | |
| WO | WO 2010/110471 A1 | 9/2010 | | |
| WO | WO 2011/015870 A1 | 2/2011 | | |
| WO | WO 2012/050359 A2 | 4/2012 | | |
| WO | WO 2013/041983 A1 | 3/2013 | | |
| WO | WO 2013/064837 | 5/2013 | | |
| WO | WO-2013064837 A1 * | 5/2013 | ............ | A61K 9/113 |
| WO | WO 2014/064459 A2 | 5/2014 | | |
| WO | WO 2014/064461 A1 | 5/2014 | | |
| WO | WO 2014/087175 A2 | 6/2014 | | |

OTHER PUBLICATIONS

Sunghee Lee et al., Sensitivity of cationic surfactant templates to specific anions in liquid interface crystallization, Mar. 11, 2012, Journal of Colloid and Interface Science, Elsevier, vol. 376, pp. 152-159 (Year: 2012).*

Villar et al., "Formation of droplet networks that function in aqueous environments," Dec. 2011, Macmillan Publishers Ltd, vol. 6, Nature Nanotechnology, published online Nov. 6, 2011, pp. 803-808 (Year: 2011).*

European Search Report for European Patent Application No. 13 805 487.9, "Droplet Assembly by 3D Printing", Date of completion: Jun. 21, 2016.

U.S. Appl. No. 61/592,062, Multisomes: Encapsulated Droplet Networks, filed Jan. 30, 2012.

International Search Report and Written Opinion from International Application No. PCT/GB2013/052794; Filing Date: Oct. 25, 2013; Entitled: "Hydrogel Network"; dated Jul. 1, 2014.

International Preliminary Report on Patentability from International Application No. PCT/GB2013/052794; Filing Date: Oct. 25, 2013; Entitled: "Hydrogel Network", dated Apr. 28, 2015.

International Search Report and Written Opinion from International Application No. PCT/GB2013/052796; Filing Date: Oct. 25, 2013; Entitled: "Droplet Assembly Method", dated Jan. 28, 2014.

International Preliminary Report on Patentability from International Application No. PCT/GB2013/052796; Filing Date: Oct. 25, 2013; Entitled: "Droplet Assembly Method", dated Apr. 28, 2015.

International Search Report and Written Opinion from International Application No. PCT/GB2013/053229; Filing Date: Dec. 6, 2013; Entitled: "Droplet Assembly By 3D Printing," dated Jun. 17, 2014.

International Preliminary Report on Patentability from International Application No. PCT/GB2013/053229; Filing Date: Dec. 6, 2013; Entitled: "Droplet Assembly By 3D Printing"; dated Jun. 9, 2015.

International Search Report and Written Opinion from International Application No. PCT/GB2012/052736, entitled: "Multisomes: Encapsulated Droplet Networks", dated Apr. 25, 2013.

International Preliminary Report on Patentability from International Application No. PCT/GB2012/052736, entitled: "Multisomes: Encapsulated Droplet Networks", dated May 6, 2014.

Abbott, A., "Biology's new dimension", Nature, 424: 870-872 (Aug. 21, 2003).

Abramoff, M. D., et al., "Image processing with Image J", Biophotonics International, 11: 36-42 (2004).

Aghdaei, S., et al., "Formation of artificial lipid bilayers using droplet dielectrophoresis", Lab Chip, 8: 1617-1620 (2008).

Akashi, K., et al., "Preparation of Giant Liposomes in Physiological Conditions and Their Characterization Under an Optical Microscope", Biophysical Journal, 71: 3242-3250 (Dec. 1996).

Aronson, M. P. and Princen, H. M., "Contact angles associated with thin liquid-films in emulsions", Nature, 286: 370-372 (Jul. 24, 1980).

Astier, Y., et al., "Protein components for nanodevices", Current Opinion in Chemical Biology 9: 576-584 (2005).

Bai, Y. et al., "A double droplet trap system for studying mass transport across a droplet-droplet interface", Lab Chip, 10: 1281-1285 (2010).

Bayley, H. et al., "Droplet interface bilayers", Molecular BioSystems, 4(12): 1191-1208 (Dec. 2008).

Bodor, N. and Buchwald, P., "Soft Drug Design: General Principles and Recent Applications", Med. Res. Rev., 20:58-101 (2000).

Boland, Thomas et al., "Application of inkjet printing to tissue engineering", Biotechnology Journal, 1: 910-917 (2006).

Bolinger, P.-Y. et al., "Integrated Nanoreactor Systems: Triggering the Release and Mixing of Compounds Inside Single Vesicles", J. Am. Chem. Soc., 126(28): 8594-8595 (2004).

Boroske, E., and Elwenspoek, M., "Osmotic Shrinkage of Gian Egg-Lecithin Vesicles", Biophys. J., 34: 95-109 (Apr. 1981).

Bowden, N., et al., "Molecule-Mimetic Chemistry and Mesoscale Self-Assembly", Acc. Chem. Res. 34(3): 231-238 (2001).

Bowden, N., et al., "Self-Assembly of Mesoscale Objects into Ordered Two-Dimensional Arrays", Science, 276: 233-235 (Apr. 11, 1997).

Channon, K., et al., "Synthetic biology through biomolecular design and engineering", Current Opinion in Structural Biology, 18: 491-498 (2008).

Cheley, S. et al., "Spontaneous oligomerization of a staphylococcal alpha-hemolysin conformationally constrained by removal of residues that form the transmembrane beta-barrel", Protein Engineering, 10: 1433-1443 (1997).

Chiarabelli, C. et al., "Chemical approaches to synthetic biology", Current Opinion in Biotechnology, 20: 492-497 (2009).

Choi, I. S. et al., "MacroscopicHierarchial, Two-Dimensional Self-Assembly", Angew. Chem. Int. Ed, 38(20): 3078-3081 (1999).

Chu, C.-J. et al., "Efficiency of Cytoplasmic Delivery by pH-Sensitive Liposomes to Cells in Culture", Pharmaceutical Research, 7(8): 824-834 (1990).

Chu, L.-Y. et al., "Controllable Monodisperse Multiple Emulsions", Angew. Chem. Int. Edit., 46: 8970-8974 (2007).

Clancy, K. and Voigt, C. A., Programming cells: towards an automated 'Genetic Compiler', Current Opinion in Biotechnology, 21: 572-581 (2010).

Clavel, F. and Hance, A. J., "Medical Progress HIV Drug Resistance", New England Journal of Medicine, 350(10): 1023-1035 (Mar. 4, 2004).

Cukierman, E. et al., "Cell interactions with three-dimensional matrices", Current Opinion in Cell Biology, 14: 633-639 (2002).

Cukierman, E. et al., "Taking Cell-Matrix Adhesions to the Third Dimension", Science, 294: 1708-1712 (Nov. 23, 2001).

Devine, D. V., et al., "Liposome-complement interactions in rat serum: implications for liposome survival studies", Biochim. Biophys. Acta, 1191: 43-51 (1994).

Dixit, S. S., et al., "Droplet Shape Analysis and Permeability Studies in Droplet Lipid Bilayers", Langmuir, 28: 7442-7451 (2012).

Dixit, S. S., et al., "Light-Driven Formation and Rupture of Droplet Bilayers", Langmuir 26(9): 6193-6200 (2010).

Drummond, D. C. et al., "Current status of pH- sensitive liposomes in drug delivery", Progress in Lipid Research, 39: 409-460 (2000).

Du, Y., et al., "Directed assembly of Cell-laden microgels for fabrication of 3D tissue constructs", Proc. Natl. Acad. Sci. (PNAS), 105(28): 9522-9527 (2008).

Evans, E., "Probing the Relation Between Force-Lifetime-and Chemistry in Single Molecular Bonds," Annu. Rev. Biophys. Biomol. Struct., 30:105-128 (2001).

Forterre, Y., et al., "How the Venus Flytrap Snaps," Nature, 43:421-425 (2005).

Funakoshi, et al., "Lipid Bilayer Formation by Contacting Monolayers in a Microfluidic Device for Membrane Protein Analysis," Anal. Chem., 78(24): 8169-8174(2006).

Gibson, D. G et al., "Creation of a Bacterial Cell Controlled by a Chemically Synthesized Genome," Science, 329:52-56 (2010).

(56) References Cited

OTHER PUBLICATIONS

Gijs, M. A., et al., "Microfluidic Applications of Magnetic Particles for Biological Analysis and Catalysis," *Chem. Rev.*, 110:1518-1563 (2010).

Gross, L.C., et al., "Determining Membrane Capacitance by Dynamic Control of Droplet Interface Bilayer Area," *Langmuir*, 27:14335-14342 (2011).

Gu, L. Q., et al., "Stochastic Sensing of Organic Analytes by a Pore-Forming Protein Containing a Molecular Adapter," *Nature*, 398:686-690 (1999).

Gu, L. Q., et al., "Interaction of the noncovalent molecular adapter, betacyclodextrin, with the staphylococcal alpha-hemolysin pore," *Biophys. J.*, 79:1967-1975 (2000).

Hamer, W. J., et al., "Osmotic Coefficients and Mean Activity Coefficients of Uni-Univalent Electrolytes in Water at 25° C.," *J. Phys. Chem. Ref. Data*, 1:1047-1100 (1972).

Hamilton, J. A., et al., "Transfer of Oleic Acid Between Albumin and Phosphholipid Vesicles," *Proc. Natl Acad. Sci. USA*, 83:82-86 (1986).

Harada, A., et al., "Macroscopic Self-Assembly Through Molecular Recognition," *Nat. Chem.* 3:34-37 (2011).

Harada, et al., "Bubble wrap of cell-like aggregates", *Nature*, 471:172-175 (2011).

Harriss, L. M., et al., "Imaging Multiple Conductance States in an Alamethicin Pore," *J. Am. Chem. Soc.*, 133:14507-14509 (2011).

Heron, A .J., et al., "Direct detection of membrane channels from gels using water-in-oil droplet bilayers," *J. Am. Chem. Soc.*, 129:16042-16047 (2007).

Heron, A. J., et al., "Simultaneous measurement of ionic current and fluorescence from single protein pores," *J. Am. Chem. Soc.*, 131:1652-1653 (2009).

Holden, M. A., et al., "Functional bionetworks from nanoliter water drops," *J. Am. Chem. Soc.*, 129:8650-8655 (2007).

Hu, Z. B., et al., "Synthesis and Application of Modulated Polymer Gels," *Science*, 269: 525-527 (1995).

Huang, J., et al., "Direct Quantitation of Peptide-MediatedProtein Transport across a Droplet-Interface Bilayer," *JACS*, 133:15818-15821 (2011).

Humphrey, W., et al., "VMD: Visual Molecular Dynamics," *J. Molec. Graphics*, 14:33-38 (1996).

Hwang, W. L., et al., "Electrical Behavior of Droplet Interface Bilayer Networks: Experimental Analysis and Modeling," *JACS*, 129:11854-11864 (2007).

Jeong, B., et al., "Lessons from Nature: Stim uli-Responsive Polymers and their Biomedical Applications," *Trends Biotechnol.*, 20:305-311 (2002).

Johnson, J. D., "Intracellular EDTA mimics parvalbumin in the promotion of skeletal muscle relaxation", *Biophys. J.* 76:1514-1522 (1999).

Kankare, J. et al., "Kinetics of Langmuirian Adsorption onto Planar, Spherical, and Cylindrical Surfaces," Langmuir,15:5591-5599 (1999).

Kim, J., et al., "Designing Responsive Buckled Surfaces by Half-tone Gel Lithography," Science,335:1201-1205 (2012).

Klein, Y., et al., "Shaping of Elastic Sheets by Prescription of Non-Euclidean Metrics," Science,315:1116-1120 (2007).

Korlach, J. et al., "Characterization of lipid bilayer phases by confocal microscopy and fluorescence correlation spectroscopy", *Proc. Natl. Acad. Sci. USA*, 96, 8461-8466 (1999).

Lahann, J., et al., "A Reversibly Switching Surface," *Science*, 299:371-374 (2003).

Lehmann, et al., "Two-dimensional magnetic manipulation of microdroplets on a chip as a platform for bioanalytical application," *Sensors and Actuators B*, 2(117):457-463 (2006).

Leptihn, S., et al., "In Vitro Reconstitution of Eukaryotic Ion Channels Using Droplet Interface Bilayers," *J. Am. Chem. Soc.*, 133:9370-9375 (2011).

Leunissen, M. E. et al., "Switchable Self-Protected Attractions in DNA-Functionalized Colloids," *Nat. Mater*, 8:590-595 (2009).

Levental, I., et al., "Soft Biological Materials and Their Impact on Cell Function," *Soft Matter*, 3:299-306(2007).

Liang, H. Y., et al., "Growth, Geometry, and Mechanics of a Blooming Lily," *Proc. Natl. Acad. Sci. USA*, 108:5516-5521 (2011).

Lichtenberg, D. et al., "Effect of surface curvature on stability, thermodynamic behavior, and osmotic activity of dipalmitoylphosphatidylcholine single lamellarvesicles," *Biochemistry (Mose.)*, 20:3462-3467 (1981).

Lindsey, H., et al., "Physicochemical characterization of 1,2-diphytanoyl-sn-glycero-3-phosphocholine in model membrane systems," *Biochim. Biophys. Acta*, 555:147-167 (1979).

Maglia, G. et al., "Analysis of single nucleic acid molecules with protein nanopores," *Method. Enzymol.* 475:591-623 (2010).

Maglia, G. et al., "Droplet networks with incorporated protein diodes show collective properties," *Nat. Nanotechn*,1(4)437-440 (2009).

Maglia, M. et al., "DNA strands from denatured duplexes are translocated through engineered protein nanopores at alkaline pH.," *Nano Lett.*, 9:3831-3836 (2009).

Mills, J. K., et al., "Lysolipid incorporation in dipalmitoylphosphatidylcholine bilayer membranes enhances the ion permeability and drug release rates at the membrane phase transition," *BBA-Biomembranes*, 1716:77-96 (2005).

Morisaku, T., et al., "Development of a new experimental system for monitoring biomembrade reactions: combinatin of laser spectroscopic techniques and biomembrane models formed at an oil/water interfacez," *Anal. Sci.*,20:1605-1608 (2004).

Nakagawa, S., et al., "Structural and functional studies of gap junction channels," *Curr. Opin. Struc. Biol.*, 20:423-430 (2010).

Naraghi, M., "T-jump study of calcium binding kinetics of calcium chelators," *Cell Calcium*, 22:255-268 (1997).

Nath, U., et al., "Genetic Control of Surface Curvature," *Science*, 299:1404-1407 (2003).

Needham, D. , et al., "The development and testing of a new temperature-sensitive drug delivery system for the treatment of solid tumors," *Adv. Drug Deliver. Rev.*, 53:285-305 (2001).

Niculescu-Duvaz, I., et al., "Antibody-directed enzyme prodrug therapy (ADEPT): a review," *Adv. Drug Deliver. Rev.*, 26:151-172 (1997).

Noireaux, V., et al., "A Vesicle Bioreactor as a sStep Toward an Artificial Cell Assembly," Proc. Natl. Acad. Sci. USA, 101:17669-17674 (2004).

Noireaux, V., et al., "Development of an Artificial Cell, from Self-Organization to Computation and Self-Reproduction," *Proc. Natl. Acad. Sci., USA*, 108:3473-3480 (2011).

Okushima, S., et al., "Controlled production of monodisperse double emulsions by two-step droplet breakup in microfluidic devices," *Langmuir*, 20:9905-9908 (2004).

Payne, G. F., "Biopolymer-Based Materials: The Nanoscale Components and their Hierarchical Assembly," *Curr. Opin. Chem. Biol.*, 11:214-219 (2007).

Poulin et al., "Influence of the Alkyl Surfactant Tail on the Adhesion Between Emulsion Drops," J. Phys. Chern. B, 103(25)5157-5159 (1999).

Poulin, P., et al., "Adhesion of Water Droplets in Organic Solvent," Langmuir, 14: 6341-6343 (1998).

Poulos, J. L., et al., "Electrowetting on Dielectric-Based Microfluids for Integrated Lipid Bilayer Formation and Measurement," Appl. Phys. Lett., 95:013706 (2009).

Pouponneau, P., et al., "Co-encapsulation of magnetic nanoparticles and doxorubicin into biodegradable microcarriers for deep tissue targeting by vascular MRI navigation," *Biomaterials*,32:3481-3486 (2011).

Rautio, J. et al., "Prodrugs: design and clinical applications," *Nat. Rev. Drug Discov.*, 7:255-270 (2008).

Raychaudhuri, P., et al., "Fluorinated Amphiphiles Control the Insertion of α-Hemolysin Pores into Lipid Bilayers," *Biochemistry* 50:1599-1606 (2011).

Ringeisen, B. R., et al., "Jet-based methods to print living cells", *Biotechnology Journal*,1:930-948 (2006).

Russew, M.-M., et al., "Photoswitches: From Molecules to Materials," *Adv. Mater*, 22:3348-3360 (2010).

Sacanna, S., et al., Lock and Key Colloids, *Nature*,464:575-578 (2010).

(56) References Cited

OTHER PUBLICATIONS

Sanjana, N. E., et al., "A fast flexible ink-jet printing method for patterning dissociated neurons in culture," *Journal of Neuroscience Methods*, 136(2):151-163 (2004).
Sapra, K. T., et al., "Lipid-coated hydrogel shapes as components of electrical circuits and mechanical devices," *Scientific Reports*,2(848):1-9 (2012).
Sapra, K. T., et al., "Three dimensional construction of bilayer networks using shape encoded hydrogel," *Biophysical Journal*, 100(3):502a (2011).
Sarles, S. A., et al., "Bilayer Formation between Lipid-Encased Hydrogels Contained in Solid Substrates," *ACS Applied Materials & Interfaces*, 2(12)3654-3663 (2010).
Sarles, S. A., et al., "Biomolecular material systems with encapsulated interface bilayers," *MRS Proceedings*, 1301, (2011).
Sarles, S. A., et al., "Cell-inspired electroactive polymer materials incorporating biomolecular materials" *Proceedings of SPIE*, 7976:797626-1-797626-9 (2011).
Schrum, J. P., et al., "The Origins of Cellular Life," Cold Spring Harb Perspect Biol 2, pp. 1-16 (2010).
Schwille, P., "Bottom-Up Synthetic Biology:Engineering in a Tinkerer's World," Science, 333: 1252-1254 (2011).
Seo, M. et al., "Microfluidic consecutive flow-focusing droplet generators," *Soft Matter* 3:986-992(2007).
Sharon, E., et al., "Buckling Cascades in Free Sheets," *Nature*, 419: 579-579 (Oct. 10, 2002).
Sharon, E., et al., "Geometrically Driven Wrinkling Observed in Free Plastic Sheets and Leaves," *Phys. Rev. E*, 75, 7 pages (2007).
Shum, H. C. et al., "Multicompartment Polymersomes from Double Emulsions" *Angew. Chem. Int. Edit.*, 50: 1648-1651 (2011).
Sidorenko, A., et al., Reversible Switching of Hydrogel-Acutated Nanostructures into Complex Micropatterns, *Science*, 315: 487-490 (Jan. 26, 2007).
Skotheim, J. M. & Mahadevan, L., "Physical Limits and Design Principles for Plant and Fungal Movements," *Science*, 308: 1308-1310 (May 27, 2005).
Small, D. M., et al., "The Ionization Behavior of Fatty Acids and Bile Acids in Micelles and Membranes," *Hepatology*, 4: 77S-79S (1984).
Solé, R. V. et al., "Synthetic Protocell Biology: From Reproduction to Computation", *Philos. T. R. Soc. B*, 362: 1727-1739 (2007).
Stanley, C.E. et al., "*A Microfluidic Approach for High-Throughput Droplet Interface Bilayer (DIB) Formation,*" *Chem Commun*, 46: 1620-1622 (2010).
Stoddart, D. et al., "Single-Nucleotide Discrimination in Immobilized DNA Oligonucleotides with a Biological Nanopore," *Proc. Natl. Acad. Sci. USA*, 106: 7702-7707 (May 12, 2009).
Strambio-De-Castillia, C. et al., "The Nuclear Pore Complex: Bridging Nuclear Transport and Gene Regulation," *Nat. Rev. Mol. Cell Bio.*, 11: 490-501 (Jul. 2010).
Syeda, R. et al., "Screening Blockers Against a Potassium Channel with a Droplet Interface Bilayer Array", *J. Am. Chem. Soc.*, 130: 15543-15548 (2008).
Synytska, A. et al., "Simple and Fast Method for the Fabrication of Switchable Bicomponent Micropatterned Polymer Surfaces," *Langmuir*, 23: 5205-5209 (2007).
Szostak, J.W., et al., "Synthesizing Life," *Nature*, 409: 387-390 (Jan. 18, 2001).
Tamaddoni, N. J. et al., "Fabricating Neuromast-Inspired Gel Structures for Membrane-Based Hair Cell Sensing," *Proceedings of SPIE*, vol. 8339: 833908-1-833908-11 (Apr. 3, 2012).
Theberge, A.B. et al., "Microdroplets in Microfluidics: An Evolving Platform for Discoveries in Chemistry and Biology," *Angew Chem. Int. Ed.*, 49: 5846-5868 (2010).
Tokarev, I. & Minko, S., "Stimuli-Responsive Porous Hydrogels at Interfaces for Molecular Filtration, Separation, Controlled Release, and Gating in Capsules and Membranes," *Adv. Mater*, 22: 3446-3462 (2010).
Torchilin, V. P., "Recent Advances with Liposomes as Pharmaceutical Carriers," *Nat. Rev. Drug Discov.*, 4: 145-160 (Feb. 2005).

Tsuchiya et al., "On-Chip Polymerase Chain Reaction Microdevice Employing a Magnetic Droplet-Manipulation System," *Sensors and Actuators B*, 130(2): 583-588 (2008).
Tuteja, A. et al., "Robust Omniphobic Surfaces," *Proc. Natl. Acad. Sci.*, 105: 18200-18205 (Nov. 25, 2008).
Ueno, M., et al., "Characteristics of the Membrane Permeability of Temperature-Sensitive Liposome," *Bull. Chem. Soc. Jpn.*, 64: 1588-1593 (1991).
Velev, O. D., et al., "On-Chip Manipulation of Free Droplets," *Nature*, 426: 515-516 (2003).
Villar, G., et al., "Formation of Droplet Networks that Function in Aqueous Environments," *Nat. Nanotechnol.*, 6: 803-808 (2011).
Walsh, C., "Molecular Mechanisms that Confer Antibacterial Drug Resistance," *Nature*, 406: 775-781 (Aug. 17, 2000).
Wang et al., "Controllable Microfluidic Production of Multicomponent Multiple Emulsions," RSC, *Lab Chip*, 11, 7 pages (2011).
Weibel, D. B. & Whitesides, G.M., "Applications of Microfluidics in Chemical Biology," *Curr. Opin. Chem. Biol.*, 10: 584-591 (2006).
Wheeldon, I., et al., "Nanoscale Tissue Engineering: Spatial Control over Cell-Materials Interactions," *Nanotechnology*, 22: 212001, 16 pages (2011).
White, N. "Antimalarial Drug Resistance and Combination Chemotherapy," *Phil. Trans. R. Soc. Lond. B*, 354: 739-749 (1999).
Whitesides, G. M., "The Origins and the Future of Microfluidics," *Nature*, 442: 368-373 (Jul. 27, 2006).
Williamson, A. J., et al,, "Templated Self-Assembly of Patchy Particles," *Soft Matter*, 7: 3423-3431 (2011).
Woolfson, D. N. & Bromley, E. H. C., "Synthetic Biology: A Bit of Rebranding, or Something New and Inspiring?" *Biochemist e-volution*, 33(1): 19-25 (Feb. 2011).
Wu, L.-Q. & Payne, G.F., *Biofabrication: Using Biological Materials and Biocatalysts to Construct Nanostructured Assemblies*, Trends Biotechnol., 22(11): 593-599 (Nov. 2004).
Xu, G. & McLeod, H. L., "Strategies for Enzyme/Prodrug Cancer Therapy," *Clin. Cancer Res.*, 7: 3314 3324 (Nov. 2001).
Xu, J., et al., "Synthetic Protocells to Mimic and Test Cell Function," *Adv. Mater.* 22: 120-127 (2010).
Yamada, K. M. & Cukierman, E., "Modeling Tissue Morphogenesis and Cancer in 3D," *Cell*, 130: 601-610 (2007).
Yoo, J.-W. & Mitragotri, S., "Polymer Particles that Switch Shape in Response to a Stimulus," *Proc. Natl. Acad. Sci.*, 107(25): 11205-11210 (Jun. 22, 2010).
Yue, B. Y. et al., "Phospholipid Monolayers at Non-Polar Oil/Water Interfaces. Part 1—Phase Transitions in Distearoyl-lecithin Films at the n-Heptane Aqueous Sodium Chloride Interface," *J. Chem. Soc. Farad. T.*, 1(72): 2685-2693 (1976).
Zagnoni, M. et al., "A Microdroplet-Based Shift Register," *Lab Chip*, 10: 3069-3073 (2010).
Zelikin, A. N. et al., "Poly(Methacrylic Acid) Polymer Hydrogel Capsules: Drug Carriers, Sub-Compartmentalized Microreactors, Artificial Organelles," *Small*, 6(20): 2201-2207 (2010).
Zhu, J. & Marchant, R.E., "Design Properties of Hydrogel Tissue-Engineering Scaffolds," *Expert Rev. Med. Devices*, 8: 607-626 (2011).
Zimmerberg, J. & Kozlov, M. M., How Proteins Produce Cellular Membrane Curvature,: *Nat. Rev. Mol. Cell Bio*, 7: 9-19 (Jan. 2006).
Pays et al.; "Coalescence in Surfactant-Stabilized Double Emulsions", *Langmuir*, 17: 7758-7769 (2001).
Rojas et al., "Temperature-Induced Protein Release from Water-in-Oil-in-Water", *Langmuir*, 24: 7154-7160 (2008).
Wang et al., "Liposomes in Double-Emulsion Glogules," *Langmuir*, 26(5): 3225-3231 (2010).
Non-Final Office Action for U.S. Appl. No. 14/354,706, "Multisomes: Encapsulated Droplet Networks" dated Sep. 9, 2016.
Non-Final Office Action for U.S. Appl. No. 14/438,345, "Hydrogel Network" dated Nov. 30, 2016.
Non-Final Office Action for U.S. Appl. No. 14/437,340, "Droplet Assembly Method" dated Nov. 4, 2016.
Kim, S., et al., "Preparation of Multivesicular Liposomes", Biochimica et Biophysica Acta., 728(1983): 339-348.
Final Office Action for U.S. Appl. No. 14/437,340, "Compact Spiral-Wound Filter Elements, Modules and Systems " dated Dec. 6, 2017.

(56) References Cited

OTHER PUBLICATIONS

Final Office Action for U.S. Appl. No. 14/437,340, "Droplet Assembly Method" dated: Sep. 10, 2018.
Office Action for U.S. Appl. No. 14/354,706, "Multisomes: Encapsulated Droplet Networks" dated Jul. 12, 2018.
Office Action for U.S. Appl. No. 14/437,340, "Droplet Assembly Method " dated Sep. 10, 2018.
Final Office Action for U.S. Appl. No. 14/437,340, "Droplet Assembly Method " dated Apr. 5, 2019.
Office Action for U.S. Appl. No. 14/354,706, "Multisomes: Encapsulated Droplet Networks" dated May 1, 2019.
Office Action for U.S. Appl. No. 15/788,441, "Hydrogel Network", dated May 14, 2019.
Notice of Allowance for U.S. Appl. No. 14/354,706, "Multisomes: Encapsulated Droplet Networks", dated Sep. 18, 2019.
Office Action for U.S. Appl. No. 14/437,340, "Droplet Assembly Method " dated Oct. 22, 2019.
Final Office Action for U.S. Appl. No. 15/788,441, "Hydrogel Network", dated Nov. 15, 2019.
Final Office Action for U.S. Appl. No. 14/437,340 "Droplet Assembly Method" dated Apr. 30, 2020.
Office Action for U.S. Appl. No. 15/788,441, "Hydrogel Network", dated May 27, 2020.
Ex Parte Quayle Office Action for U.S. Appl. No. 14/437,340, "Droplet Assembly Method", dated Oct. 14, 2020.
Notice of Allowance for U.S. Appl. No. 14/437,340, "Droplet Assembly Method", dated Nov. 3, 2020.
Notice of Allowance for U.S. Appl. No. 15/788,441, "Hydrogel Network" dated Dec. 9, 2020.
Supplemental Notice of Allowability for U.S. Appl. No. 15/788,441, "Hydrogel Network" dated Jan. 13, 2021.
Office Action for U.S. Appl. No. 16/721,302 "Multisomes: Encapsulated Droplet Networks" dated Mar. 3, 2021.

* cited by examiner

Fig. 8

Initialisation

- Set printing parameters
- Initialise communication with Arduino and manipulator
- Read ejection parameters
- Read maps
- Define goals for current layer and pass
- Set current goal
- Set high speed
- Go to initial goal
- ■ Reached initial goal?
- Set low speed ■ Stop until true
◆ If true, go to →
   If false, go to ↓

Direction

- ■ Reached current goal?
- ◆ Current goal first in pass?
  - → Reset interface
- Fire piezo according to current goal
- Pause (droplet delay)
- Find next goal
- ◆ Current pass done?
  - → Update pass and layer
    - ◆ All layers done?
      - → St high speed
        - Raise capillaries out of oil
    - Set goals for next pass and layer
- ◆ Reached end of row?
  - → Pause (row delay)
- Go to next goal Fig. 9
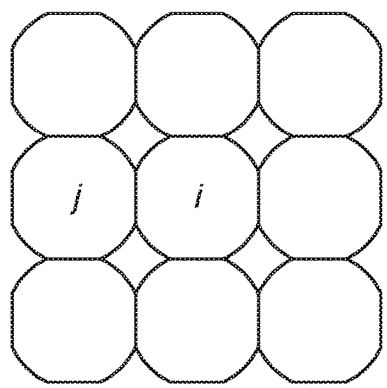
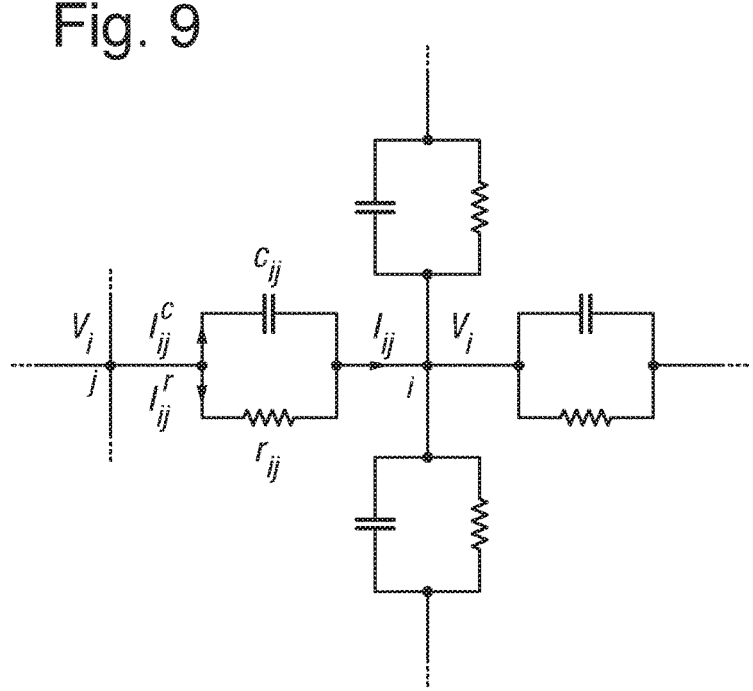

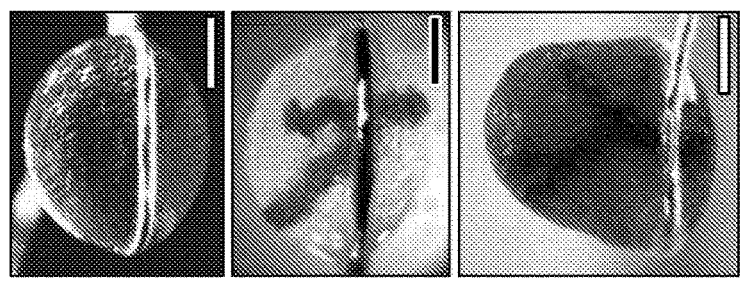
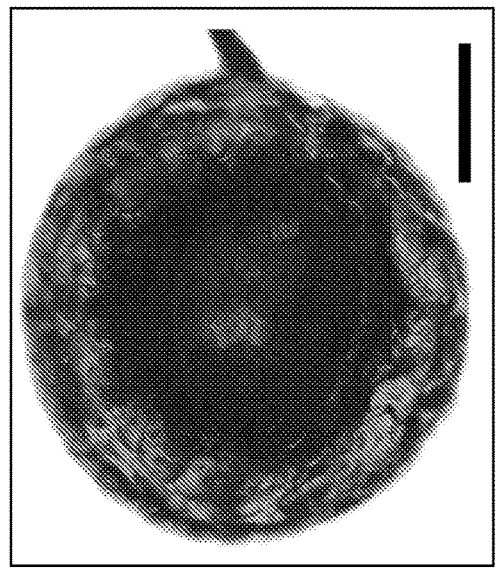
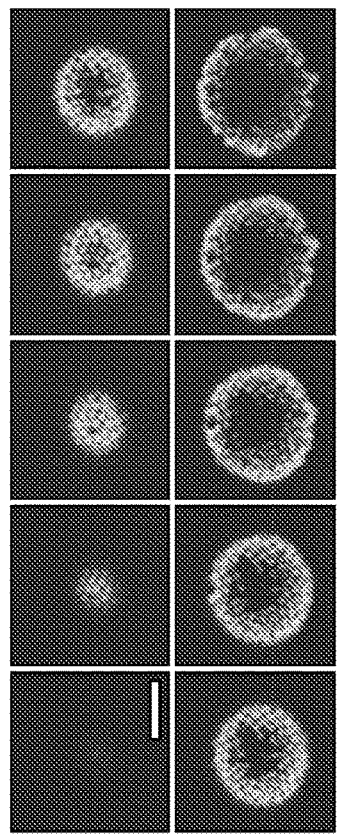
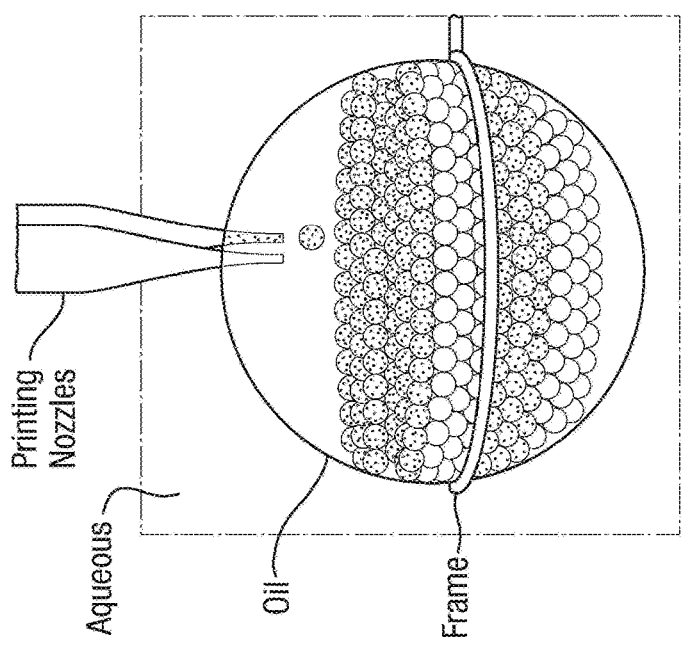

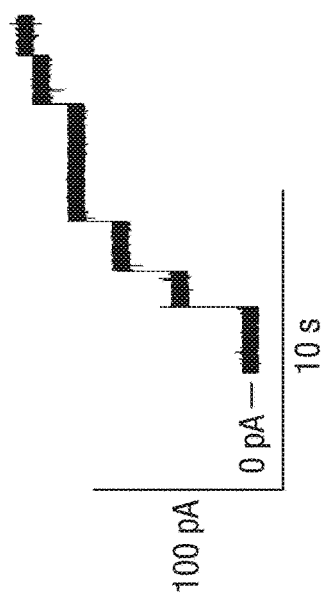
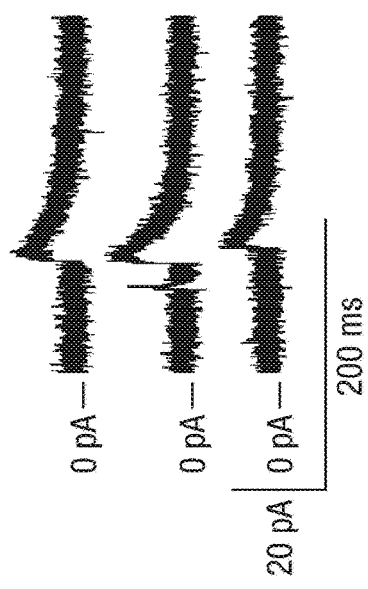
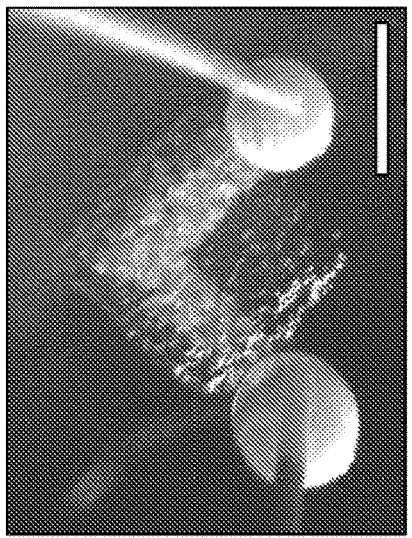
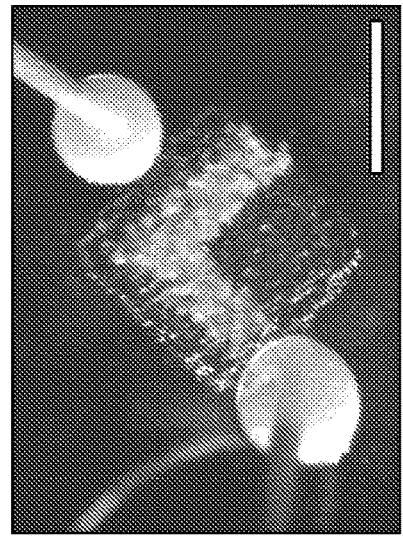
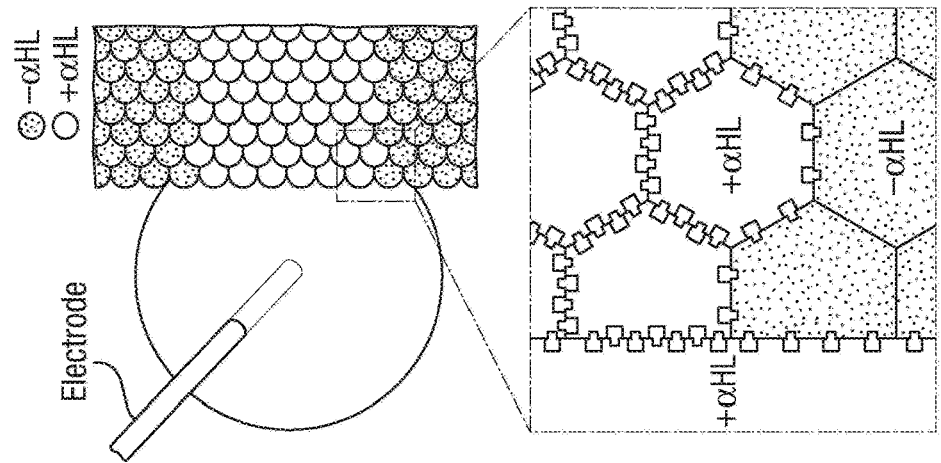

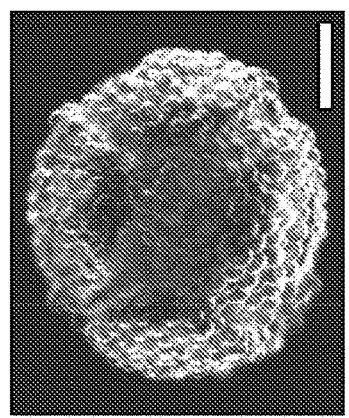
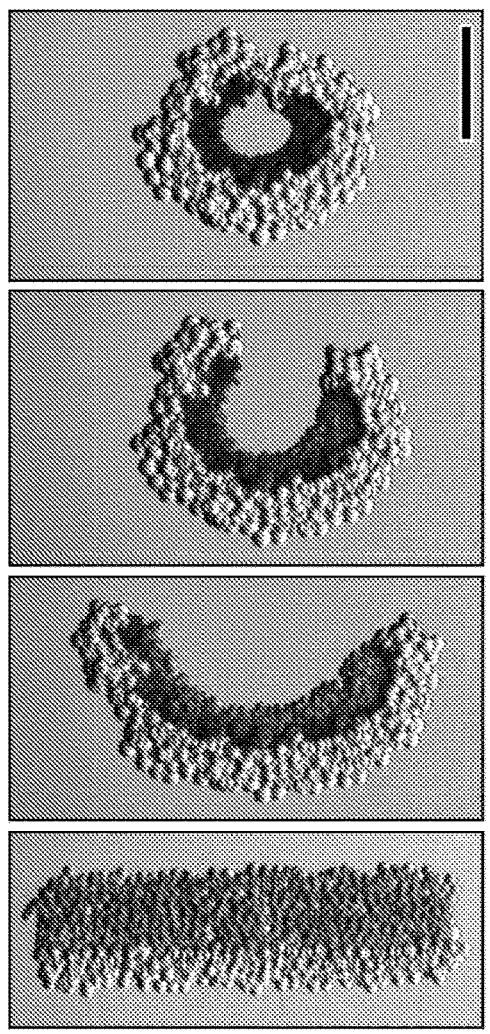
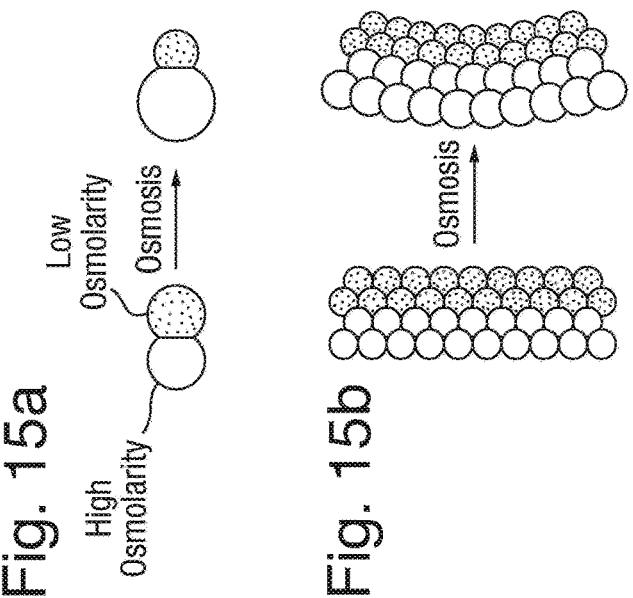
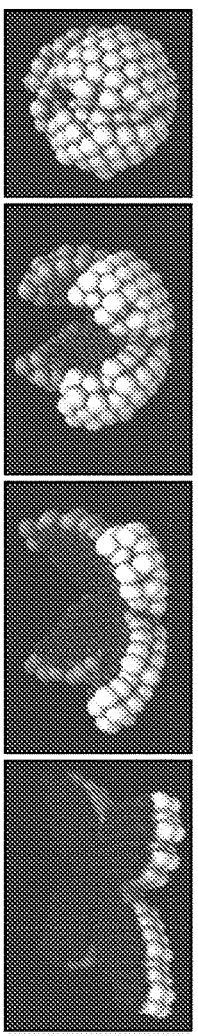

DROPLET ASSEMBLY BY 3D PRINTING

RELATED APPLICATION

This application is the U.S. National Stage of International Application No. PCT/GB2013/053229, filed Dec. 6, 2013, which designates the U.S., published in English, and claims priority under 35 U.S.C. §§ 119 or 365(c) to Great Britain Application No. 1222052.1, filed Dec. 7, 2012.

FIELD OF THE INVENTION

The invention relates to an apparatus for producing a droplet assembly, which apparatus comprises a droplet generator. A process for producing a droplet assembly, using an apparatus comprising a droplet generator is also described. The invention also relates to droplet assemblies comprising a plurality of droplets. Various uses of the droplet assemblies are also described.

BACKGROUND TO THE INVENTION

Aqueous droplets in a solution of lipids in oil adhere by forming lipid bilayers at their interfaces (Poulin, P. et al., Langmuir 14, 6341-6343 (1998) and Holden, M. A., et al., J. Am. Chem. Soc. 129, 8650-8655 (2007)). Networks of droplets functionalized with membrane proteins have been built and can act as light sensors (Holden, M. A., et al., J. Am. Chem. Soc. 129, 8650-8655 (2007)), batteries (Holden, M. A., et al., J. Am. Chem. Soc. 129, 8650-8655 (2007)) or simple electrical circuits (Maglia, G. et al., Nature Nanotech. 4, 437-440 (2009)). Droplet networks can be stabilized in bulk aqueous solution, and programmed to release their contents upon a change in pH or temperature (Villar, G., et al., Nature Nanotech. 6, 803-808 (2011)). However, defined networks have been limited to simple arrangements of few droplets, typically assembled manually (Holden, M. A., et al., J. Am. Chem. Soc. 129, 8650-8655 (2007) and Maglia, G. et al., Nature Nanotech. 4, 437-440 (2009)), by microfluidic means (Bai, Y. et al., Lab. Chip 10, 1281-1285 (2010), Zagnoni, M. et al., Lab. Chip 10, 3069-3073 (2010) and Stanley, C. E. et al., Chem. Commun. 46, 1620-1622 (2010)) or by manipulation with external fields (Aghdaei, S., et al., Lab. Chip 8, 1617-1620 (2008), Poulos, J. L., et al., Appl Phys Lett 95, 013706 (2009) and Dixit, S. S., et al., Langmuir 26, 6193-6200 (2010)).

There is therefore an ongoing need to develop a method of producing complex droplet assemblies, such as a three-dimensional droplet assembly, and an apparatus for the production of a droplet assembly.

SUMMARY OF THE INVENTION

The present invention relates to an apparatus for producing a droplet assembly, which apparatus enables droplet assemblies to be produced by an automated process. The invention also relates to an automated process for producing a droplet assembly.

The speed and precision with which a droplet assembly can be produced using the apparatus of the invention and the process of the invention allows complex assemblies of droplets to be created.

The inventors have demonstrated that millimetre-scale geometries comprising tens of thousands of droplets can be produced. Even larger structures with billions of droplets may also now be produced using this invention. Surprisingly, these structures are self-supporting and resistant to gentle perturbations. Further, the structures themselves may be complex and diverse, with structures not accessible by previously known methods now being achievable.

The precise location and composition of each droplet in the droplet assembly can be controlled. Thus the droplet assemblies can be easily functionalised, for instance, by the incorporation of membrane proteins into bilayers between specific contacting droplets. For example, the inventors have shown that a simple functional mimic of nervous tissue can been produced by the inclusion of membrane proteins in specific droplets within an assembly. The droplet assemblies may also be functionalised by the inclusion of a variety of different materials, including small molecules, enzymes and living cells, within specific droplets. Living cells may, for example, be allowed to grow within the droplets of the droplet assembly, and to break down the bilayers between droplets some time after printing.

The droplet assemblies may also be used as sacrificial templates for the patterning of solid materials. For example, inorganic materials may be included in specific droplets of the droplet assembly. Different inorganic materials can be placed in different droplets within the droplet assembly. The inorganic materials may then diffuse between specific droplets, and react to form inorganic solids such as cadmium sulphide.

Further, droplet assemblies can be built to comprise two or more different compartments. The individual compartments may communicate with each other and/or with the external environment by, for example, using membrane proteins. Sophisticated, compartmentalised systems may therefore be produced.

Utilising the process of osmosis, the inventors have also been able to create self-folding networks that fold in a predictable way. The ability of the droplet assembly to change shape allows new and more sophisticated structures to be developed. The assemblies could, for example, be designed as a hydraulic mimic of muscle tissue. Applications such as the use of a droplet assembly as an autonomously functioning entity, interacting with living organisms or electronics, are now a realistic prospect. An assembly may, for example, be used as a platform for drug delivery or even as part of an artificial tissue. The use of droplet networks in tissue engineering is a particularly interesting prospect as it could reduce or even overcome many issues commonly observed with living cells, such as the replication and migration of cells and the rejection of tissues by the body.

Accordingly, the invention provides an apparatus for producing a droplet assembly, which apparatus comprises: at least one droplet generator; a container which is moveable relative to the at least one droplet generator; and a control unit, which control unit is adapted to control the dispensing of droplets from the at least one droplet generator and the movement of the container relative to the at least one droplet generator, wherein the apparatus is adapted to produce a droplet assembly which comprises a plurality of droplets, wherein each of said droplets comprises (i) a droplet medium and (ii) an outer layer of amphipathic molecules around the surface of the droplet medium, wherein the droplet medium is an aqueous medium or a hydrophobic medium, and wherein at least one of said droplets contacts another of said droplets to form a layer of said amphipathic molecules as an interface between the contacting droplets.

The invention also provides a process for producing a droplet assembly using an apparatus for producing the droplet assembly, which droplet assembly comprises: a plurality of droplets, wherein each of said droplets comprises: (i) a droplet medium, and (ii) an outer layer of amphipathic molecules around the surface of the droplet medium, wherein the droplet medium is an aqueous medium or a hydrophobic medium, and wherein at least one of said droplets contacts another of said droplets to form a layer of said amphipathic molecules as an interface between the contacting droplets; which apparatus comprises: at least one droplet generator; a container which is moveable relative to the at least one droplet generator; and a control unit, which control unit is adapted to control the dispensing of droplets from the at least one droplet generator and the movement of the container relative to the at least one droplet generator; wherein said container of the apparatus contains a bulk medium, wherein: when the droplet medium is an aqueous medium the bulk medium is a hydrophobic medium, and when the droplet medium is a hydrophobic medium the bulk medium is an aqueous medium; which process comprises: (a) a plurality of dispensing steps, wherein each dispensing step comprises dispensing a droplet of the droplet medium from a said droplet generator into the bulk medium, in the presence of amphipathic molecules, and thereby forming in the bulk medium a droplet which comprises (i) said droplet medium and (ii) an outer layer of amphipathic molecules around the surface of the droplet medium; and (b) moving the container relative to the at least one droplet generator, to control the relative positioning of the droplets in the bulk medium.

In another aspect, the invention provides a droplet assembly which is obtainable by a process as defined hereinabove.

In a further aspect, the invention provides a droplet assembly which comprises a plurality of droplets, wherein each of said droplets comprises (i) an aqueous medium, and (ii) an outer layer of amphipathic molecules around the surface of the aqueous medium, and wherein each of said droplets contacts another of said droplets to form a bilayer of said amphipathic molecules as an interface between the contacting droplets, wherein the plurality of droplets comprises a first region of said droplets and a second region of said droplets, wherein each droplet in the first region contacts at least one other droplet in the first region to form a bilayer of said amphipathic molecules as an interface between the contacting droplets, and each droplet in the second region contacts at least one other droplet in the second region to form a bilayer of said amphipathic molecules as an interface between the contacting droplets, wherein the aqueous medium of the droplets in the first region has a first osmolarity and the aqueous medium of the droplets in the second region has a second osmolarity, wherein the first osmolarity is different from the second osmolarity.

Also provided by the invention is a droplet assembly which comprises a plurality of droplets, wherein each of said droplets comprises (i) an aqueous medium, and (ii) an outer layer of amphipathic molecules around the surface of the aqueous medium, and wherein each of said droplets contacts another of said droplets to form a bilayer of said amphipathic molecules as an interface between the contacting droplets, wherein the plurality of droplets defines a shell around a volume within the droplet assembly that does not comprise said droplets.

In further aspects, the invention provides various uses of the droplet assemblies of the invention as defined herein.

Thus, the invention provides the use of a droplet assembly of the invention as defined herein in synthetic biology.

The invention also provides the use of a droplet assembly of the invention as defined herein as a drug-delivery vehicle.

The invention also provides the use of a droplet assembly of the invention as defined herein in tissue engineering. A droplet of the droplet assembly may, for instance, comprise living cells.

The invention also provides the use of a droplet assembly of the invention as defined herein in material science and engineering.

Further provided by the invention is the use of a droplet assembly as defined herein for the droplet assembly of the invention as a template for the patterning of a solid material.

BRIEF DESCRIPTION OF THE FIGURES

FIG. 2 shows printed droplet networks.

FIG. 6 shows a printing pattern.

pixels.

FIG. 7 demonstrates printing distortions. All the networks in this figure were printed with the simple printing pattern of FIG. 6b.

FIG. 8 provides an outline of a printing algorithm. The instructions labelled Initialization are executed first, followed by those labelled Direction. The conditions marked by squares must be met before the algorithm continues to the next instruction. At the evaluation of the conditions marked by diamonds, the algorithm continues to the instruction marked by the horizontal arrow if the condition is true, or to that marked by the vertical arrow if the condition is false. The delays after making each droplet or row are explained in the Examples, under Supplementary Discussion.

FIG. 9 shows an electrical representation of a general droplet network. $V_i$ and $V_j$ are the electrical potentials at the droplets labelled i and j, respectively. $c_{ij}$ and $r_{ij}$ are, respectively, the capacitance and resistance between droplets i and j. $I_{ij}$ is the ionic current flowing from j into i, and consists of a capacitive component $I_{ij}^c$ and resistive component $I_{ij}^r$. The droplets are illustrated on a square grid only for clarity; the derivation in the Examples applies to a network in any arrangement.

FIG. 11 shows droplet networks printed in bulk aqueous solution. FIG. 11a provides a schematic of printing in aqueous solution. The nozzles eject aqueous droplets into a drop of oil that is suspended in bulk aqueous solution by a wire frame. FIG. 11b shows a micrograph of a network printed in aqueous solution, viewed from above. A core of light grey droplets is surrounded by a shell of darker grey droplets, which contain the fluorescent dye pyranine. The scale bar represents 400 μm.

FIG. 11c shows horizontal sections of the network in FIG. 11b obtained by confocal microscopy, showing the fluorescent shell of droplets around the non-fluorescent core. The sections span approximately the bottom 150 μm of the network. The scale bar represents 400 μm.

FIG. 11d shows micrographs of three other networks printed in bulk aqueous solution. The scale bars represent 400 μm.

FIG. 12 demonstrates an electrically conductive pathway. FIG. 12a shows a schematic of part of a network printed with a pathway that allows the flow of ionic current. Only the light grey droplets and the large drop contain α-hemolysin (αHL) pores. The large drop is impaled with an Ag/AgCl electrode. The magnified section illustrates the αHL pores in the bilayers around the αHL-containing droplets.

FIG. 12b provides a photograph of a printed network with electrode-impaled drops placed on either end of the conductive pathway. The light grey droplets contain αHL, while the other droplets contain no protein. The scale bar represents 500 μm. FIG. 12c shows a stepwise increase in the ionic current, as measured in the configuration in FIG. 12b, at 50 mV in 1 M KCl at pH 8.0.

FIG. 12d provides a photograph of the network in FIG. 12b, after separating one of the large drops and rejoining it onto the network at a position away from the pathway. The scale bar represents 500 μm. FIG. 12e shows selected portions of a single recording as measured in the configuration in d at 50 mV, showing transient increases in ionic current.

FIG. 13 illustrates electrical measurements of droplet networks with and without αHL.

FIG. 14 demonstrates electrical simulations of a conductive droplet pathway.

FIG. 15 illustrates self-folding networks. FIG. 15a provides a schematic of two droplets of different osmolarities joined by a lipid bilayer. The transfer of water through the bilayer causes the droplets to swell or shrink. FIG. 15b shows a schematic of a droplet network that comprises two strips of droplets of different osmolarities. The transfer of water between the droplets induces an overall deformation of the network. FIG. 15c provides a photographs of a rectangular network folding into a circle over ~3 h. The light grey and dark grey droplets initially contain 250 mM KCl and 16 mM KCl, respectively. The scale bar represents 250 µm.

FIG. 15d shows photographs of a flower-shaped network folding spontaneously into a sphere. The light grey and darker grey droplets initially contain 80 mM KCl and 8 mM KCl, respectively. The photographs cover a period of 8 h. The scale bar represents 200 µm. FIG. 15e shows the network in FIG. 15d in its final configuration, photographed from above. The scale bar represents 200 µm. FIG. 15f shows frames from a folding simulation of a network with a similar initial geometry to the network shown in FIG. 15d. Dark grey (top layer) and light grey (bottom layer) represent the lowest and highest initial osmolarities, respectively, and white (final frame) indicates the average of the two.

FIG. 16 illustrates the measurement of water permeability of droplet interface bilayers.

FIG. 17 demonstrates fracture of folding networks.

DETAILED DESCRIPTION OF THE INVENTION

Figure 1:
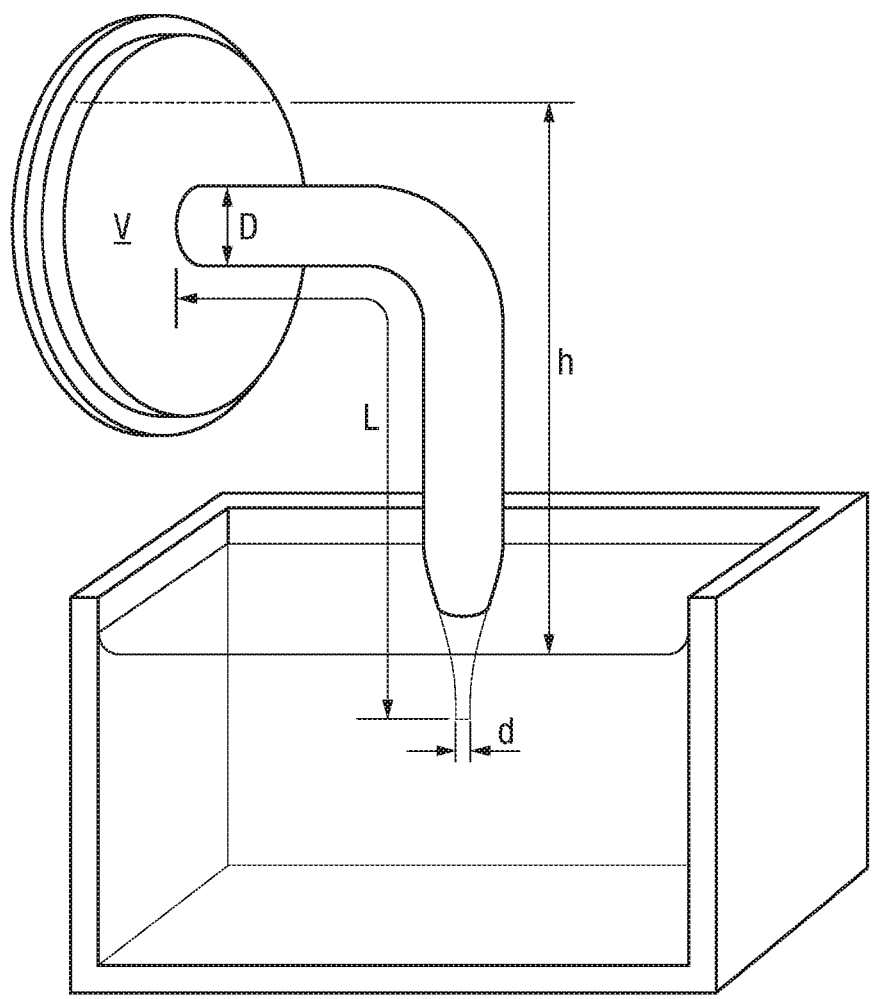
FIG. 1 shows a schematic of a droplet generator. The droplet generator chamber is filled with a volume V of aqueous solution. The nozzle of length L has an internal diameter D at its base, and a tip diameter d. The level of the aqueous solution in the chamber is a distance h above the level of the oil solution in the well.

The present invention relates to an apparatus for producing a droplet assembly, which apparatus comprises: at least one droplet generator; a container which is moveable relative to the at least one droplet generator; and a control unit, which control unit is adapted to control the dispensing of droplets from the at least one droplet generator and the movement of the container relative to the at least one droplet generator, wherein the apparatus is adapted to produce a droplet assembly which comprises a plurality of droplets, wherein each of said droplets comprises (i) a droplet medium, and (ii) an outer layer of amphipathic molecules around the surface of the droplet medium, wherein the droplet medium is an aqueous medium or a hydrophobic medium, and wherein at least one of said droplets contacts another of said droplets to form a layer of said amphipathic molecules as an interface between the contacting droplets.

Typically, the apparatus is adapted to produce said droplet assembly wherein each of said droplets contacts another of said droplets to form a layer of said amphipathic molecules as an interface between the contacting droplets.

The layer of said amphipathic molecules which is an interface between contacting droplets may, for instance, be a bilayer of said amphipathic molecules or a layer of a block copolymer. The layer of a block copolymer may, for example, be a layer of a triblock copolymer.

When the droplet medium is an aqueous medium the layer of said amphipathic molecules which is an interface between contacting droplets may, for instance, be a bilayer of said amphipathic molecules or a layer of a block copolymer.

When the droplet medium is a hydrophobic medium the layer of said amphipathic molecules which is an interface between contacting droplets may, for instance, be a bilayer of said amphipathic molecules or a layer of a block copolymer. In the bilayer of amphipathic molecules formed, the polar heads of the amphipathic molecules are in contact with each other. (See, for example, Aronson et al., Nature, Vol. 286, July 1980 and in Poulin et al., J. Phys. Chem. B, Vol. 103, no. 25, June 1999.)

Typically, the layer of said amphipathic molecules which is an interface between contacting droplets is a bilayer of said amphipathic molecules.

The droplet medium is typically an aqueous medium. Another embodiment is envisaged however in which the droplet medium is a hydrophobic medium.

Usually, the droplet medium is an aqueous medium. The aqueous medium may be any suitable aqueous medium. For instance, the aqueous medium may be pure water, or an aqueous buffer solution, or an aqueous solution of one or more salts. Alternatively, the aqueous medium may comprise a hydrogel. When the aqueous medium comprises a hydrogel, the aqueous medium may, for instance, comprise agarose and water. The concentration of the agarose in water is typically less than or equal to 10% w/v agarose. For instance, the concentration of the agarose in said water may be from 0.25 to 5% w/v agarose. Hydrogels other than agarose may also be used. For instance the aqueous medium may comprise methylcellulose, polyethylene glycol diacrylate, polyacrylamide, matrigel, hyaluronan, polyethylene oxide, polyAMPS (poly(2-acrylamido-2-methyl-1-propanesulfonic acid)), polyvinylpyrrolidone, polyvinyl alcohol, sodium polyacrylate, acrylate polymers or poly(N-isopropylacrylamide). Alternatively, the aqueous medium body may comprise a silicone hydrogel or LB (Luria broth) agar.

One important property of the aqueous medium is pH and this can be varied over a wide range. In some embodiments, for instance, the pH of the aqueous medium within the aqueous droplet or droplets may be in the range of from 5 to 9 (or for instance in the range of from 6 to 8) although higher and lower pH values are also possible. The aqueous medium may therefore be an aqueous buffer solution. Any suitable buffer can be employed, depending on the desired pH. The buffer solution may for instance comprise Tris-HCl and/or KCl. In some embodiments the pH of the aqueous buffer solution is from 5 to 9, or for instance from 6 to 8. The nature and concentration of the solutes can be varied to vary the properties of the solution.

The aqueous medium of each droplet in the droplet assembly may be the same or different.

The amphipathic molecules of a droplet need not be all of the same type. Rather, the amphipathic molecules may in some embodiments be a mixture of two or more different kinds of amphipathic molecule. Another important example is that the amphipathic molecules in the respective outer layers of different droplets in a droplet assembly may be of different types so that the bilayer(s) formed between the different droplets may be asymmetric.

Typically, the apparatus is adapted to produce a droplet assembly which is disposed in a bulk medium wherein when the droplet medium is an aqueous medium the bulk medium is a hydrophobic medium, and when the droplet medium is a hydrophobic medium the bulk medium is an aqueous medium. When the bulk medium is an aqueous medium, the aqueous medium may be as further defined hereinbefore. Similarly, when the droplet medium is a hydrophobic medium, the hydrophobic medium may be as further defined hereinbelow.

Usually, the droplet medium is an aqueous medium and the bulk medium is a hydrophobic medium, and the invention will generally be described hereinbelow in these terms. However, as the skilled person will appreciate, any of the embodiments of the invention described herein in those terms may also be performed "in reverse", using a hydrophobic medium as the droplet medium instead of an aqueous medium, and using an aqueous medium as the bulk medium instead of a hydrophobic medium.

Typically, the droplet medium is an aqueous medium and the apparatus is adapted to produce a droplet assembly which is disposed in a hydrophobic medium. The hydrophobic medium may, for instance, be a hydrophobic medium as further defined hereinbelow.

A droplet of the aqueous medium is usually dispensed into the hydrophobic medium in the presence of amphipathic molecules. The amphipathic molecules may, for instance, be disposed in the aqueous medium or in the hydrophobic medium. Typically, the amphipathic molecules are disposed in the hydrophobic medium.

When the aqueous medium is dispensed into the hydrophobic medium in the presence of amphipathic molecules, an aqueous droplet forms, which droplet comprises (i) an aqueous medium and (ii) an outer layer of amphipathic molecules around the surface of the aqueous medium.

The droplet assembly comprises at least two droplets in contact with each other. The boundary that is shared between contacting droplets, at the point of contact between the objects, is referred to herein as an interface. An interface is formed when part of the outer layer of one droplet contacts part of the outer layer of another droplet. For instance, when the droplet is brought into contact with the other droplet, a bilayer of amphipathic molecules may form at the interface between the two objects. The bilayer comprises amphipathic molecules from the outer layer of amphipathic molecules around the surface of the aqueous medium of each droplet at the interface. The bilayer forms as it is an energetically more favourable configuration for the amphipathic molecules to adopt. The contacting droplets will acquire the geometry with the lowest free surface energy.

Typically, the apparatus of the invention is adapted to produce said droplet assembly wherein each of said droplets contacts another of said droplets to form a bilayer of said amphipathic molecules as an interface between the contacting droplets.

The droplet assembly may comprise one interface, or it may comprise two or more interfaces. Typically, the droplet assembly comprises at least n of said droplets, and at least n–1 of said interfaces between contacting droplets, wherein n is equal to or greater than 2. The integer n may be equal to or greater than 3. More typically, n is equal to or greater than 4.

In some embodiments, when the droplet assembly comprises at least n of said droplets, the network may comprise n or more than n interfaces, wherein n is as herein defined, it being understood that any one droplet can be in contact with (and therefore form an interface with) more than one other droplet.

An advantage of the present invention is that the apparatus enables millimetre-scale, or larger, droplet assemblies to be produced. The integer n can in principle be very high, for instance of the order of millions. Such networks, which can in principle comprise millions of droplets, may, for instance, be useful for preparing prototissue (i.e. an multi-compartment analogue of protocells) or minimal tissue. In some embodiments, therefore, the integer n may be as high as several million, for instance up to about 100,000,000, or for instance up to about 50,000,000. The integer n may, for instance, be up to about 10,000,000, or for instance up to about 5,000,000.

In other embodiments, n may be at least several hundred, for instance at least about 500, or for instance at least about 1000. The integer n may for instance be an integer of from 500 to 5,000,000, or an integer of from 5,000 to 500,000. n may be an integer of from 10,000 to 50,000.

The droplet assembly may, for instance, be a droplet assembly as defined hereinbelow.

Droplet assemblies produced using the apparatus of the invention may be multi-compartment systems. The droplet assembly may, for instance, comprise a first compartment and a second compartment. The first compartment within the droplet assembly may communicate with the second compartment via membrane proteins. The first and/or second compartment may communicate with the external environment (i.e. environment external to the droplet assembly) via membrane proteins. In principle, a droplet assembly may comprise a large number of compartments and architecturally defined structures may thus be produced.

The control unit of the apparatus is usually adapted to coordinate (a) the movement of the container relative to the or each droplet generator and (b) the dispensing of the droplets, to create said droplet assembly.

The control unit may, for instance, be adapted to control the movement of the container. Alternatively, the control unit may be adapted to control the movement of the or each droplet generator. Typically, the control unit is adapted to control the movement of the container.

Figure 4:
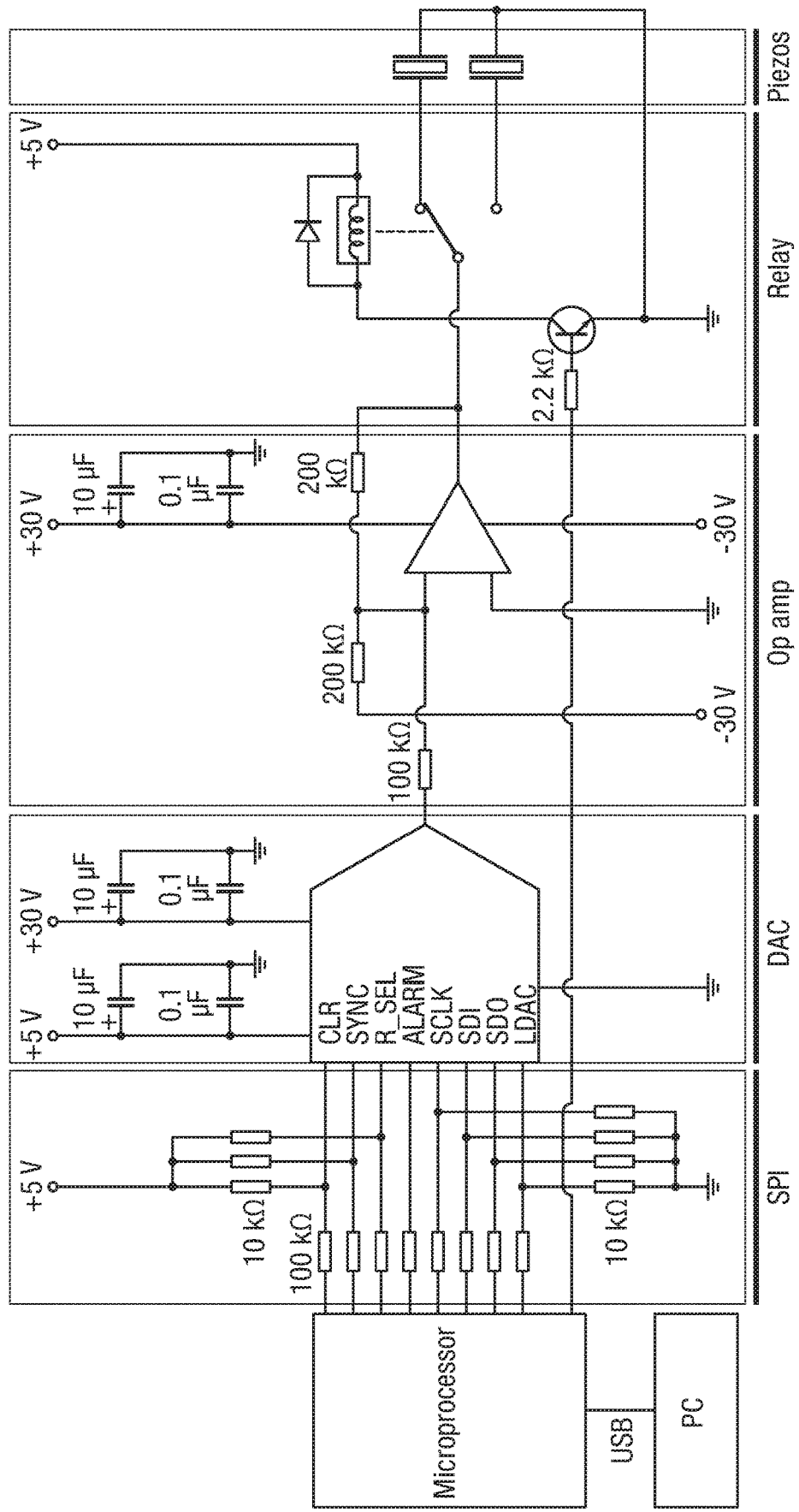
FIG. 4 provides a schematic of driving electronics for droplet generators. The electronics allow a computer to apply a voltage in the range −30 V to +30 V, with 12-bit resolution, to one of two piezoelectric transducers. Abbreviations: PC, personal computer; USB, universal serial bus; SPI, serial peripheral interface; DAC, digital-to-analog converter; op amp, operational amplifier.

Typically, the control unit comprises a computer or dedicated electronic hardware. More typically, the control unit comprises at least one computer. It usually comprises at least one personal computer (PC). The control unit may, for instance, be a PC. In some embodiments, the control unit comprises a PC and dedicated electronic hardware (as shown in FIG. 4).

Usually, the control unit is adapted to control the dispensing of droplets of the aqueous medium from the or each droplet generator. An example of the driving electronics for the or each droplet generator is provided in FIG. 4.

The droplet generator may, for instance, be a microfluidic system. It may, for instance, (a) generate droplets on demand or (b) produce droplets in a continuous stream and select specific droplets to be deposited. Usually, the droplet generator generates droplets on demand. The droplet generator may: (i) generate and expel a droplet in a single step; or (ii) generate and expel a droplet in separate steps. Usually, the droplet generator generates and expels a droplet in a single step.

Typically, the at least one droplet generator is a piezoelectric droplet generator. More typically, the at least one droplet generator is a piezoelectric droplet generator which comprises a piezoelectric transducer for dispensing droplets.

The aqueous medium may, for instance, be dispensed from the or each droplet generator by the application of a voltage pulse to the piezoelectric component. Usually, the control unit controls the application of the voltage pulses to the piezoelectric component. Typically, the voltage pulse has a peak-to-peak amplitude of from 5 V to 100 V, for instance, of from 10 V to 80 V. The peak-to-peak amplitude may, for instance, be of from 20 V to 60 V. Typically, each pulse has a duration of from 10 to 1,500 μs, for instance, of from 50 to 1,000 μs. More typically, each pulse has a duration of from 100 to 800 μs. Usually, the voltage pulse is a square voltage pulse.

Figure 10:
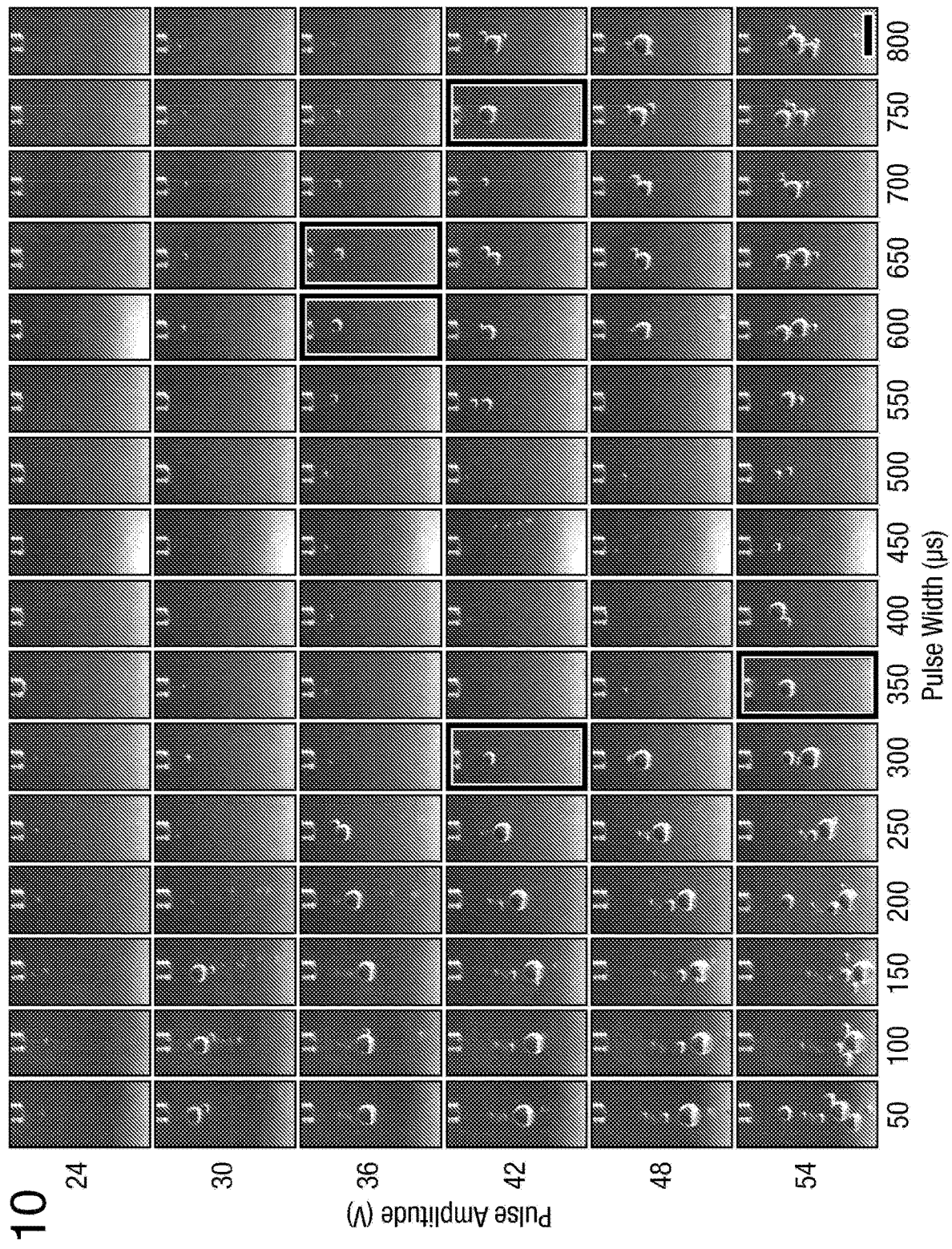
FIG. 10 demonstrates droplet ejection as a function of pulse width and voltage. Photographs were taken immediately after droplet ejection, for various widths and amplitudes of the voltage pulse applied to a droplet generator. To determine the reproducibility of the ejected droplets, each combination of pulse width and amplitude was applied five times with an interval of a few seconds between pulses. After every combination was tested, the entire procedure was repeated. Droplet production was consistent for each combination of pulse width and amplitude (n=10) for a given nozzle, but varied between nozzles. The highlighted photographs indicate conditions for this nozzle that produced single droplets of a suitable size for printing droplet networks. The scale bar represents 200 μm.
Figure 13A:
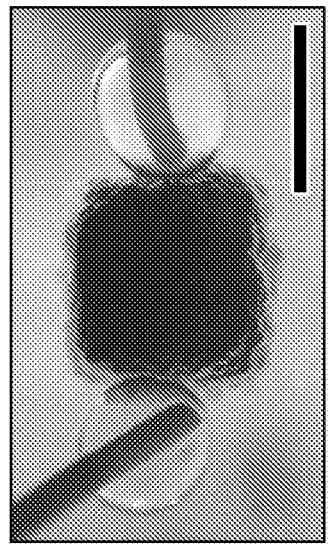
FIG. 13a shows a photograph of a network in which none of the droplets contained αHL. The network droplets and the large electrode-impaled drops contained 25 mM Tris (tris(hydroxymethyl)aminomethane) HCl, 1 M KCl, 100 μM EDTA, pH 8.0. The network droplets additionally contained 1 mM xylene cyanol FF, and the electrode-impaled drops additionally contained αHL and 10 mM pyranine. The scale bar represents 500 μm.
Figure 13B:
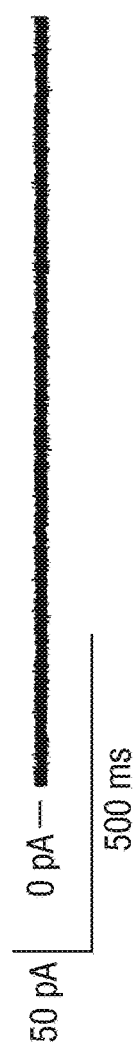
FIG. 13b provides a typical portion of the current measured at 50 mV in the configuration shown in FIG. 13a. No steps or transient spikes of current were measured from this network in any recording.
Figure 13C:
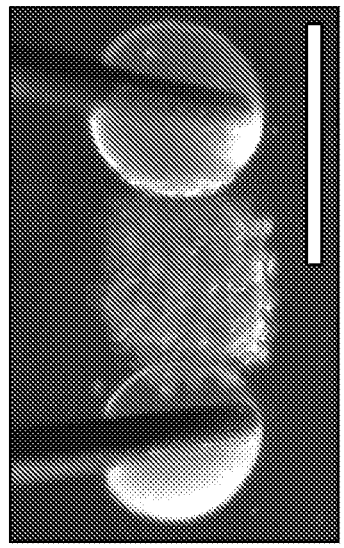
FIG. 13c provides a photograph of a network in which all of the droplets contained αHL. The network droplets and the electrode-impaled drops were of the same solution as the electrode-impaled drops in FIG. 13a. The scale bar represents 500 μm.
Figure 13D:
FIG. 13d shows a portion of the current measured at 150 mV in the configuration shown in FIG. 13c, immediately after the large drops were placed onto the network. Similar current steps were measured after twice removing and replacing the large drops onto the network.

As shown in FIG. 10, the diameter of the droplet may be tuned by varying the amplitude and duration of the voltage pulses. By varying these parameters, the droplet diameter can be tuned to a suitable diameter. The diameter may, for instance, be tuned to be from about 10 to 200 μm. Thus the control unit may be adapted to control the application of a first voltage pulse and a second voltage pulse where the first voltage pulse and the second voltage pulse are different. A single droplet generator can thus be used to produce droplets of different sizes. Alternatively, the first and second voltage pulses could be applied to the piezoelectric component of two different droplet generators.

The peak-to-peak amplitude defines the absolute value of the difference between the peak (or highest voltage) and the trough (or lowest value).

Figure 3:
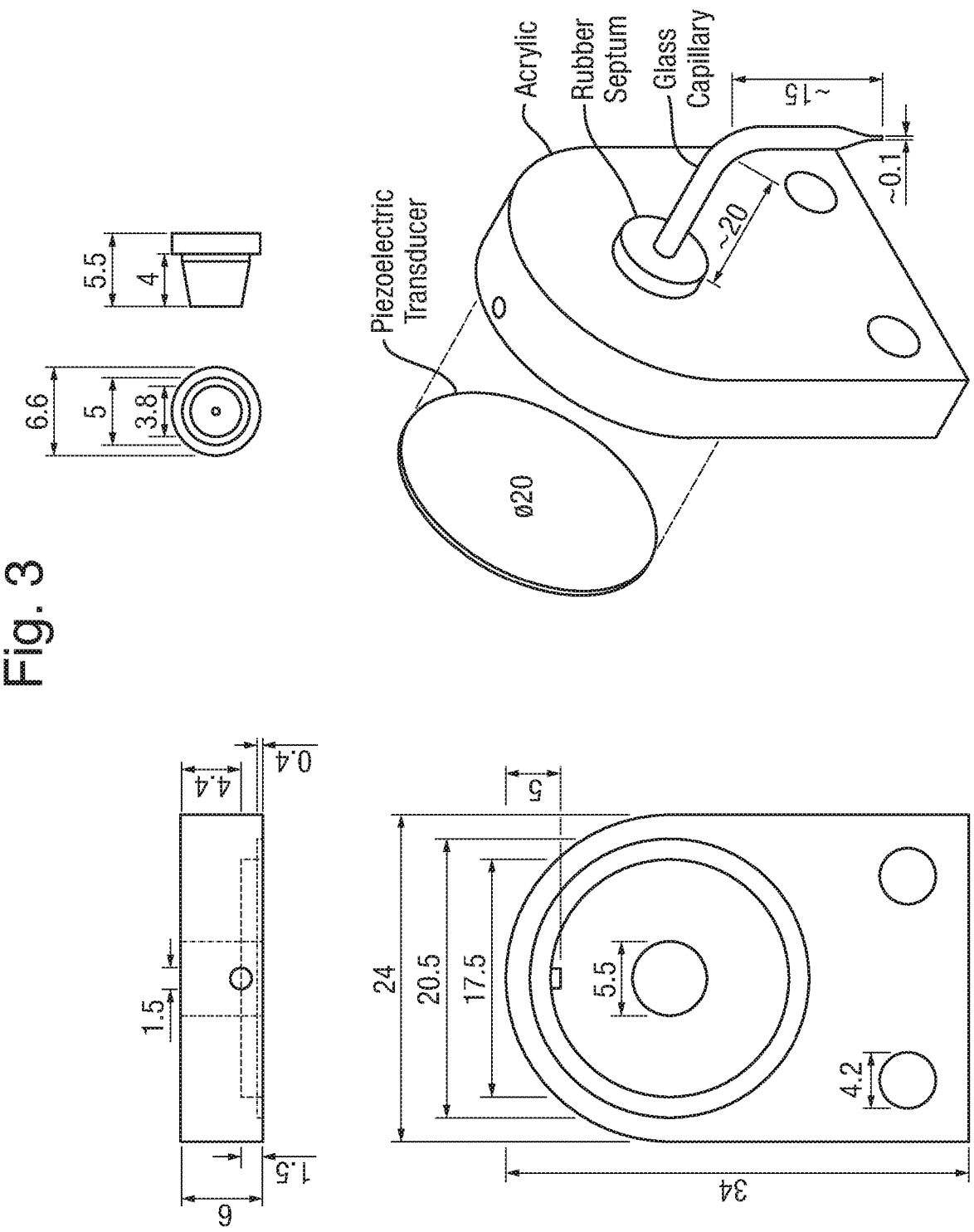
FIG. 3 provides a diagram of a droplet generator. The device consists of a piezoelectric transducer affixed onto a micromachined poly(methyl methacrylate) chamber. A rubber septum is fitted opposite the transducer, and into the septum is inserted a pulled and bent glass capillary. The two lower holes were used to fix one device in place, and to mount the other onto a manual micromanipulator. All dimensions are in mm.

The size of the droplets produce may be controlled by adapting the droplet generator. As illustrated in FIGS. 1 and 3, the droplet generator may comprise an outlet. The outlet may be adapted to control the size of the droplets produced. The outlet is discussed further below.

Typically, the control unit is adapted to control the dispensing of droplets of the aqueous medium from the or each droplet generator, so that droplets are dispensed at a rate of from 0.01 to 100 $s^{-1}$, for instance, at a rate of from 0.01 to 50 $s^{-1}$. Usually, the control unit is adapted to control the dispensing of droplets of the aqueous medium from the or each droplet generator, so that droplets are dispensed at a rate of from 0.01 to 10 $s^{-1}$.

Usually, the apparatus comprises two or more of said droplet generators. Typically, each droplet generator is as herein defined.

The size of a droplet produced may be controlled by adapting the droplet generator. Having two or more of said droplet generators enables differently-sized droplets to be produced.

The two or more droplet generators may dispense the same aqueous medium or the two or more droplet generators may dispense different aqueous media. Therefore, having two or more of said droplet generators allows droplets comprising different aqueous media to be produced. For instance, a droplet assembly comprising a first droplet comprising a first aqueous medium and a second droplet comprising a second aqueous medium may be produced using the apparatus of the invention.

Having two or more of said droplet generators allows, for example, (i) differently sized droplets to be produced and/or (ii) droplets comprising different aqueous media to be produced. Differently sized droplets may, for instance, be produced by applying different voltages to the piezoelectric components of the different droplet generators or by adapting the droplet generator.

When the amphipathic molecules are disposed in the aqueous medium, droplets comprising different amphipathic molecules may, for instance, be produced. For instance, a first droplet generator may comprise a first aqueous medium comprising a first amphipathic molecule and a second droplet generator may comprise a second aqueous medium comprising a second amphipathic molecule.

The apparatus of the invention usually further comprises a micromanipulator for moving the container relative to the or each droplet generator. Typically, the control unit is adapted to control movement of the container relative to the or each droplet generator using the micromanipulator.

More typically, the apparatus of the invention further comprises a micromanipulator for moving the container, and wherein the control unit is adapted to control movement of the container using the micromanipulator.

The micromanipulator is generally a motorized micromanipulator.

The container is typically disposed on the micromanipulator, so that the movement of the micromanipulator causes movement of the container. Typically, the control unit is adapted to control movement of the micromanipulator, which in turn causes movement of the container.

The control means is typically adapted to communicate with the micromanipulator for moving the container via an electrical or wireless signal. The control means is typically in electrical connection with the micromanipulator. Alternatively, the control means is capable of communicating with the micromanipulator wirelessly.

In some embodiments, the apparatus further comprises a micromanipulator for moving the or each droplet generator and, when the apparatus comprises more than one said droplet generator, for coordinating the relative displacement of the droplet generators.

Individual droplet generators may, for instance, be moved together or separately.

The micromanipulator for moving the container may be the same as micromanipulator for moving the or each droplet generator. Alternatively, the micromanipulator for moving the container may be the different from micromanipulator for moving the or each droplet generator. Typically, the micromanipulator for moving the container is the same as micromanipulator for moving the or each droplet generator.

The control means is typically adapted to communicate with the micromanipulator via an electrical or wireless signal. The control means is typically in electrical connection with the micromanipulator. Alternatively, the control means is capable of communicating with the micromanipulator wirelessly.

Typically, the or each droplet generator comprises a chamber for holding a droplet medium (typically an aqueous medium); an outlet; and a component for displacing a volume of said droplet medium through said outlet and thereby dispensing said volume as a droplet.

In some embodiments, the or each droplet generator further comprises an inlet.

Typically, the inlet allows entry of air into the chamber of the droplet generator upon the dispensing of a droplet from the outlet.

The inlet may, for instance, be for introducing an aqueous medium into the chamber. The chamber is typically filled with from 200 to 600 µl of the aqueous medium, for instance from 400 to 500 µl. For instance, the chamber may be filled with about 400 µl of the aqueous medium. Usually, the chamber is filled with the aqueous medium through capillary action. As the skilled person will appreciate, it may be possible for the aqueous medium to evaporate from the chamber. Evaporation may have an impact on the diameter of droplets dispensed from the droplet generator. The evaporation may be prevented by having a layer of a hydrophobic medium on top of the aqueous medium. Accordingly, in some embodiments, the aqueous medium has a layer of a hydrophobic medium on top of it. The hydrophobic medium may be any suitable hydrophobic medium. Typically, the hydrophobic medium will be a hydrophobic medium as defined herein.

There may be some applications for which only a small quantity of an aqueous medium is required. Thus, in other embodiments, the chamber is filled with from 0.5 to 50 µl of the aqueous medium, for instance from 1 to 10 µl. For instance, the chamber may be filled with about 5 µl. In these embodiments, the droplet generator is typically first filled with water. The outlet of the generator may then be immersed in a well comprising a hydrophobic medium, which hydrophobic medium may be as herein defined. Suction may then be applied at the inlet of the droplet generator, for instance, by using a micropipette. By doing this, the hydrophobic medium is drawn into the outlet. For instance, the amount of hydrophobic medium drawn into the outlet may be from 0.5 to 50 µl, for instance from 1 to 10 µl. The outlet may then be immersed into another well comprising the aqueous medium. Again, suction may be used to load from 0.5 to 50 µl of the aqueous medium, for instance from 1 to 10 into the outlet. The hydrophobic medium forms a plug within the nozzle that prevents the aqueous medium in the outlet tip from mixing with the larger volume of water. Usually, the volume of water and the hydrophobic medium together transmit the pulse of pressure created by the piezoelectric transducer to the tip of the outlet, where a droplet is formed from the aqueous medium. The outlet may, for instance, comprise a nozzle.

When the or each droplet generator comprises a chamber for holding a droplet medium (typically an aqueous medium); an outlet; and a component for displacing a volume of said droplet medium through said outlet and thereby dispensing said volume as a droplet, the means for displacing a volume of said droplet medium through said outlet may be any suitable component, such as any suitable moveable component, which is capable of displacing a volume of the droplet medium from the chamber and through the outlet of the droplet generator, and which is capable of being controlled by the control unit. The component for displacing a volume of said droplet (e.g. aqueous) medium may be a mechanical component under the control of the control unit. Typically, the component is a piezoelectric transducer.

Usually, the control means is adapted to communicate with the component for displacing a volume of said droplet (e.g. aqueous) medium through said outlet, and to thereby control the dispensing of droplets of the droplet medium from the outlet. Typically, the control means relays instructions to a microcontroller that is itself able to communicate with the component. The control means is typically in electrical connection with the microcontroller. Alternatively, the control means may be capable of communicating with the microcontroller wirelessly. When the component is a piezoelectric transducer, the microcontroller is able to control the application of a voltage pulse to the piezoelectric transducer, to cause movement of the piezoelectric transducer, which in turn causes displacement of a volume of droplet medium (e.g. aqueous medium) through the outlet of the droplet generator.

In some embodiments, the component for displacing a volume of said droplet medium (e.g. aqueous medium) through said outlet is a piezoelectric transducer. In other embodiments, the droplet is formed when a bubble of vapour behind the inlet is formed and pushed the fluid out.

Typically, the outlet has a diameter of less than 500 µm, for instance, of less than 250 µm. The diameter of the outlet provides a measure of the area through which a droplet is dispensed. The diameter is the internal diameter discussed in the Supplementary Methods and is indicated in FIG. 3. When the outlet is circular, the diameter of the outlet is the diameter of the circle. When the outlet is other than circular, the diameter of the outlet is the diameter of a circle with the same area as the outlet.

More typically, the outlet has a diameter of less than 200 µm, for instance, of less than 150 µm. For instance, the outlet typically has a diameter of from 20 µm to 200 µm, for instance from 60 µm to 120 µm. The outlet may, for instance, have a diameter of about 100 µm.

The inventors have found that it is preferable that the outlet be as small as possible relative to the droplets. This can help to reduce the drag force produced when the container is moved relative to the at least one droplet generator, for example, when the droplet assembly is disposed in a hydrophobic medium.

Typically, the outlet is cylindrical in shape.

Usually, the or each droplet generator further comprises a capillary tube to the chamber, wherein the capillary is the nozzle and the tip of the capillary is said outlet. The tip of the capillary typically has a diameter of less than 150 µm. For instance the tip of the capillary may have a diameter of from 20 µm to 200 µm, for instance from 60 µm to 120 µm. The tip of the capillary may, for instance, have a diameter of about 100 µm.

Typically, the droplet generator is adapted to dispense droplets having a diameter equal to or less than 1 mm, for instance, equal to or less than 200 µm.

Usually, the droplet generator is adapted to dispense droplets having a diameter of from 10 µm to 1 mm, for instance, from 10 µm to 200 µm. The droplet generator may, for instance, be adapted to dispense droplets having a diameter of from 30 µm to 60 µm. In some embodiments, the or each droplet generator is adapted to dispense droplets having a diameter of about 50 µm.

As mentioned above, the droplets are typically dispensed into a bulk medium. When the droplet medium is an aqueous medium the bulk medium is a hydrophobic medium. Usually, the tip of the droplet generator is immersed in said bulk medium. However, in some embodiments, the tip of the droplet generator is above said bulk medium.

The inventors have found that the height between the level of the droplet medium (usually the aqueous medium) in the chamber of the or each droplet generator and the level of the bulk medium (usually the hydrophobic medium) may affect the diameter of the droplets dispensed. Typically, the greater the difference in height, the larger the diameter of droplets dispensed. Usually, the difference in height is from 1 cm to 2 cm, for instance, about 1.5 cm.

The voltage pulse is discussed above. The required voltage pulse may depend upon the concentration of amphipathic molecules in the hydrophobic medium. As the concentration of amphipathic molecules increases, the adsorption of amphipathic molecules at the interface between the aqueous medium and the hydrophobic medium decreases the tension of that interface, lowering the energy required to form a droplet. Typically, the voltage pulse has a peak-to-peak amplitude of from 5 V to 100 V, for instance, of from 10 V to 80 V. The peak-to-peak amplitude may, for instance, be of from 20 V to 60 V.

The amphipathic molecules may be any suitable amphipathic molecule. Usually, the amphipathic molecules will be ones which are capable, when present in a high enough concentration, of forming a bilayer at any one of said interfaces. The type of amphipathic molecule that is capable of forming a bilayer may, for instance, depend on additional components of the contacting droplets. For example, if the droplets are disposed in a hydrophobic medium, the amphipathic molecules may be any suitable amphipathic molecules capable of forming a bilayer within a hydrophobic medium. The type of amphipathic molecules capable of forming a bilayer within the hydrophobic medium would typically depend on the nature of the hydrophobic medium and the aqueous medium of the droplets, but a wide range of amphipathic molecules are possible.

Amphipathic molecules are molecules which have both hydrophobic and hydrophilic groups. The outer layer of amphipathic molecules usually comprises a monolayer of amphipathic molecules on the surface of the droplet. The monolayer is typically formed and maintained naturally by the interaction of the hydrophilic and hydrophobic groups with the aqueous medium and the bulk medium so that the molecules align on the surface of the droplet with the hydrophilic groups facing inwards towards the aqueous medium and the hydrophobic groups facing outwards, for instance towards a hydrophobic medium.

The amphipathic molecules may, for instance, be non-polymeric amphipathic molecules. Alternatively, the amphipathic molecules may be polymeric amphipathic molecules.

An important class of amphipathic molecules which can be used in the droplet assembly is lipid molecules. The lipid molecules may be any of the major classes of lipid, including phospholipids, fatty acids, fatty acyls, glycerolipids, glycerophospholipids, sphingolipids, sterol lipids, prenol lipids, saccharolipids and polyketides. Some important examples include phospholipids and fatty acids, for instance phospholipids. The lipid molecules may be naturally occurring or synthetic. Whilst the formation of a bilayer from lipid molecules has been demonstrated the method is expected to be appropriate for any amphipathic molecules.

A common class of hydrophobic group that may be present in an amphipathic molecule is a hydrocarbon group, as for instance in most lipids. However, another suitable kind of hydrophobic group that may be employed is a fluorocarbon group. Thus, a further important class of amphipathic molecule is an amphipathic molecule that comprises at least one fluorocarbon group. An example of such a molecule would be a lipid-like molecule which comprises a hydrophobic fluorocarbon tail and a hydrophilic head group.

The amphipathic molecules of the droplet need not be all of the same type. Rather, the amphipathic molecules may in some embodiments be a mixture of two or more different kinds of amphipathic molecule. Another important example is that the amphipathic molecules in the respective outer layers of different droplets in a droplet assembly may be of different types so that, if bilayers are formed, the bilayer(s) formed between the different droplets may be asymmetric. In some embodiments, the lipid leaflets of two contacting droplets are different.

Typically, therefore, the amphipathic molecules comprise lipid molecules. The lipid molecules need not be all of the same type. Thus, the amphipathic molecules may comprise a single type of lipid or a mixture of two or more different types of lipid molecules. Likewise, when the droplet is in contact with another droplet, the lipid compositions of the outer layers of the individual droplets may be the same as or different from one another. Lipid molecules are particularly advantageous because lipid bilayers, or more generally bilayers of amphipathic molecules, are models of cell membranes and the droplet assembly may therefore serve as an excellent platform for a range of experimental studies, including for instance as novel platforms for the fundamental study of membrane proteins, or as multi-compartment protocellular chassis for "bottom-up" synthetic biology.

The lipid may, for instance, be sensitive to its environments (i.e. be a smart lipid). The lipid may, for instance, be sensitive to changes is pH, light or temperature. Thus the lipid may be a pH-sensitive lipid, a temperature-sensitive lipid or a light-sensitive lipid.

The lipid may allow a membrane protein (such as a natural, engineered or synthetic membrane protein) to act as a functional component of the minimal tissue.

Phospholipids are particularly preferred for reasons outlined above and also because they are a major component of all cell membranes, making droplets comprising phospholipids particularly suitable for synthetic biology applications, as well as for drug delivery.

Accordingly, the amphipathic molecules that form an outer layer on at least part of the surface of the aqueous medium typically comprise phospholipid molecules. The phospholipid molecules may be the same or different, i.e. the amphipathic molecules comprise a single kind of phospholipid, or a mixture of two or more different phospholipids. Phospholipids are well known to the skilled person and many are commercially available, from suppliers such as Avanti Polar Lipids. The phospholipid molecules may be glycerophospholipids or phosphosphingolipids or a mixture of the two. The phospholipid molecules may comprise anionic phospholipids, phospholipids comprising primary amines, choline-containing phospholipids and/or glycosphingoplipids. Usually, the amphipathic molecules comprise one or more glycerophospholipids. As the skilled person will appreciate, glycerophospholipids include, but are not limited to glycerophospholipids having a structure as defined in the following formula (I):

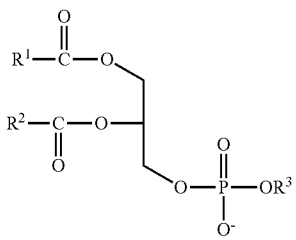

(I)

wherein:

R[1] and R[2], which are the same or different, are selected from $C_{10}$-$C_{25}$ alkyl groups and $C_{10}$-$C_{25}$ alkylene groups;

either R[3] is absent such that OR[3] is O[−], or R[3] is present and is H, $CH_2CH_2N(R^4)_3^+$, a sugar group, or an amino acid group; and each R[4], which is the same or different, is independently selected from H and unsubstituted $C_1$-$C_4$ alkyl.

Typically, when R[3] is $CH_2CH_2N(R^4)_3^+$, each R[4], which is the same or different, is selected from H and methyl. As the skilled person will appreciate, when each and every R[4] is methyl, the R[3] group is a choline group, and when each and every R[4] is H, the R[3] group is an ethanolamine group.

When R[3] is an amino acid group it may for instance be a serine group, i.e. —$CH_2CH(NH_2)(COOH)$. When R[3] is a sugar group, it may for instance be glycerol, i.e. —$CH_2CHOHCH_2OH$, or for instance inositol, i.e. —$CH(CHOH)_5$.

Typical examples of R[3] and R[2] groups are $C_{10}$-$C_{25}$ alkyl groups, including, but not limited to linear $C_{10}$-$C_{25}$ alkyl groups such as, for instance, $CH_3(CH_2)_{10}$—, $CH_3(CH_2)_{12}$—, $CH_3(CH_2)_{14}$—, $CH_3(CH_2)_{16}$—, $CH_3(CH_2)_{18}$—, $CH_3(CH_2)_{22}$— and branched $C_{10}$-$C_{25}$ alkyl groups such as for instance —$CH_2$—$CH(CH_3)$—$(CH_2)_3$—$CH(CH_3)$—$(CH_2)_3$—$CH(CH_3)$—$(CH_2)_3$—$CH(CH_3)_2$.

Further typical examples of R[1] and R[2] groups are unsubstituted $C_{10}$-$C_{25}$ alkylene groups, including, but not limited to, $CH_3(CH_2)_5CH=CH(CH_2)_7$—, $CH_3(CH_2)_7CH=CH(CH_2)_7$—, $CH_3(CH_2)_4CH=CHCH_2CH=CH(CH_2)_7$—, $CH_3(CH_2)_4(CH=CHCH_2)_3CH=CH(CH_2)_3$—, and $CH_3CH_2CH=CHCH_2CH=CHCH_2CH=CH(CH_2)_7$—.

As the skilled person will appreciate, the O[−] group in the phosphate group adjacent to the OR[3] group may in some embodiments be protonated, or associated with a suitable cation, for instance a metal cation such as Na[+].

Thus, the amphipathic molecules may comprise one or more glycerophospholipids having the structure of formula (I) as defined above.

For instance, the amphipathic molecules may comprise any one or more of the following glycerophospholipids: 1,2-diphytanoyl-sn-glycero-3-phosphocholine (DPhPC), 1,2-distearoyl-sn-glycero-3-phosphocholine (DSPC) 1,2-dipalmitoyl-sn-glycero-3-phosphocholine (DPPC), or 1,2-dipalmitoyl-sn-glycero-3-[phospho-rac-(1-glycerol)] (DPPG) can be employed as the amphiphilic molecules in the droplet, or a mixture of one or more thereof. The glycerophospholipid 1,2-dioleoyl-sn-glycero-3-phosphoethanolamine (DOPE) may also be used, and is typically used in combination with a pH-sensitive lipid, for instance a fatty acid.

Additionally or alternatively, the amphipathic molecules may comprise a steroid, which steroid comprises an alkyl side-chain. The amphipathic molecules may, for instance, comprise cholesterol, β-sitosterol and lanosterol.

In some embodiments, the amphipathic molecules comprise derivatives of phospholipids. For instance, the amphipathic molecules may comprise a phosphatidylcholine, such as POPC (1-Palmitoyl-2-oleoyl-sn-glycero-3-phosphocholine) or DPPC (1,2-dipalmitoyl-sn-glycero-3-phosphocholine), or a phosphatidylglycerol, such as POPG (1-palmitoyl-2-oleoyl-sn-glycero-3-phosphoglycerol).

Preferably, the amphipathic molecules comprise DPhPC.

The amphipathic molecules may, for instance, comprise one or more fatty acids, e.g. oleic acid. Fatty acids are of course well known to the skilled person and a wide range of these are commercially available.

The amphipathic molecules may for instance comprise a mixture comprising: (a) one or more phospholipids, and (b) one or more fatty acids.

In addition to the amphipathic molecules, the droplet may further comprise a PEGylated lipid. The term "PEGylated lipid", as used herein, refers to a lipid which has been derivatised with poly(ethylene glycol).

A PEGylated lipid may be particularly useful when the droplet assembly is in a volume (such as a drop) of a hydrophobic medium, which volume is in a hydrophilic medium such as an aqueous medium. A PEGylated lipid may, for example, be particularly useful when the droplet assembly forms part of a droplet encapsulate (for example, as defined below). The encapsulate may, for instance, be functionalised using a PEGylated lipid.

The inclusion of one or more PEGylated lipids in the droplet typically stabilises the droplet assembly in vivo, and in particular prolongs the plasma half-life of the droplet assembly. This means that, when the droplet assembly contains one or more therapeutic or diagnostic agents, for instance if it is being used as a drug-delivery vehicle the inclusion of one or more PEGylated lipids may also have the useful effect of prolonging the plasma half-life of the agent within a droplet assembly. Such effects have been observed previously when PEGylated lipids are used in liposomal drug formulations. PEGylated lipids are known in the art and are commercially available from suppliers such as NOF Corporation, Japan (see http://www.phospholipid.jp/phospholipid_2-3.html). Any suitable PEGylated lipid may be employed, including, but not limited to, PEG-phospholipids, diacylglycerol-PEG, cholesterol-PEG derivatives, and mixtures thereof.

The poly(ethylene glycol) (PEG) component of the PEGylated lipid may have any one of several different geometries. Thus, it could be substantially linear PEG or branched PEG. The branched PEG may for instance have from three to ten PEG chains emanating from a central core group. Alternatively, the branched PEG could be a star PEG, having from 10 to 100 PEG chains emanating from a central core group. Alternatively, the PEG may be a comb PEG, having multiple PEG chains grafted to a polymer backbone.

The one or more PEGylated lipids employed may for instance comprise a PEG-phospholipid of the following formula (II)

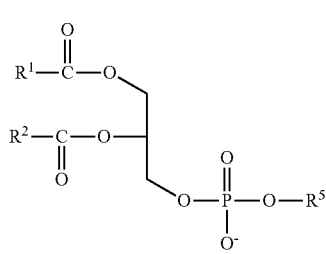

(II)

wherein R[1] and R[2] are as defined above for the glycerophospholipids of formula (I), and R[5] is a group which comprises poly(ethylene glycol).

The group which comprises poly(ethylene glycol) may for instance have the formula —$CH_2CH_2NHC(O)$—X, or for instance —$CH_2CH_2NHC(O)(CH_2)_3C(O)$—X wherein X comprises said poly(ethylene glycol). The group X may for instance comprise substantially linear PEG, or for instance a branched PEG, having, for instance, from three to ten PEG chains emanating from a central core group. Alternatively, it can be a star PEG, having, for instance, from 10 to 100 PEG chains emanating from a central core group. Or for instance it may be a comb PEG, having multiple PEG chains grafted to a polymer backbone.

Thus, $R^5$ may for instance be —$CH_2CH_2NHC(O)$—$(OCH_2CH_2)_qOCH_3$, —$CH_2CH_2NHC(O)(CH_2)_3C(O)$—$(OCH_2CH_2)_qOCH_3$, —$CH_2CH_2NHC(O)$—$(OCH_2CH_2)_qOH$, or —$CH_2CH_2NHC(O)(CH_2)_3C(O)$—$(OCH_2CH_2)_qOH$, wherein q is a positive integer. The integer q may for instance be from 5 to 10,000, or for instance from 10 to 1,000.

Alternatively, $R^5$ may be —$(CH_2CH_2O)_qCH_3$ or —$(CH_2CH_2O)_qH$, wherein q is a positive integer. The integer q may for instance be from 5 to 10,000, or for instance from 10 to 1,000.

Additionally or alternatively, the one or more PEGylated lipids may comprise a diacylglycerol-PEG of formula (III)

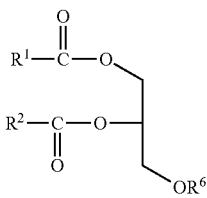

(III)

wherein $R^1$ and $R^2$ are as defined above for the glycerophospholipids of formula (I), and $R^6$ is a group which comprises poly(ethylene glycol).

The poly(ethylene glycol) may for instance comprise substantially linear PEG, or for instance a branched PEG, having, for instance, from three to ten PEG chains emanating from a central core group. Alternatively, it can be a star PEG, having, for instance, from 10 to 100 PEG chains emanating from a central core group. Or for instance it may be a comb PEG, having multiple PEG chains grafted to a polymer backbone.

$R^6$ may for instance be —$(CH_2CH_2O)_qCH_3$, —$(CH_2CH_2O)_qH$, —$CH_2CH_2NHC(O)$—$(OCH_2CH_2)_qOCH_3$, —$CH_2CH_2NHC(O)$—$(OCH_2CH_2)_qOH$, —$CH_2CH_2NHC(O)(CH_2)_3C(O)$—$(OCH_2CH_2)_qOCH_3$ or —$CH_2CH_2NHC(O)(CH_2)_3C(O)$—$(OCH_2CH_2)_qOH$ wherein q is a positive integer. The integer q may for instance be from 5 to 10,000, or for instance from 10 to 1,000.

Additionally or alternatively, the one or more PEGylated lipids may comprise a cholesterol-PEG derivative of formula (IV)

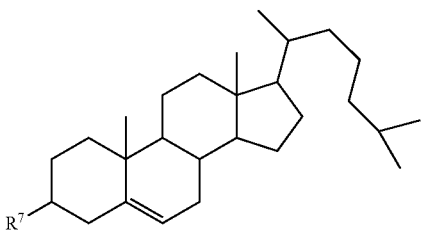

(IV)

wherein $R^7$ is a group which comprises poly(ethylene glycol).

Again, the poly(ethylene glycol) may comprise substantially linear PEG, or for instance a branched PEG, having, for instance, from three to ten PEG chains emanating from a central core group. Alternatively, it can be a star PEG, having, for instance, from 10 to 100 PEG chains emanating from a central core group. Or for instance it may be a comb PEG, having multiple PEG chains grafted to a polymer backbone.

$R^7$ may for instance be —$(OCH_2CH_2)_qOH$ or —$(OCH_2CH_2)_qOCH_3$ wherein q is a positive integer. The integer q may for instance be from 5 to 10,000, or for instance from 10 to 1,000.

Polyglycerine may be used instead of poly(ethylene glycol).

The concentration of amphipathic molecules may be any suitable concentration.

Typically, the concentration of amphipathic molecules is less than or equal to 15 mg mL$^{-1}$. For instance, the concentration of amphipathic molecules may be from 0 to 10 mg mL$^{-1}$. Usually, the concentration of amphipathic molecules is from 0.05 mg mL$^{-1}$ to 10 mg mL$^{-1}$, for instance, from 0.05 mg mL$^{-1}$ to 5 mg mL$^{-1}$. More typically, the concentration of amphipathic molecules is from 0.1 mg mL$^{-1}$ to 2.5 mg mL$^{-1}$, for instance, from 0.2 mg mL$^{-1}$ to 0.5 mg mL$^{-1}$.

Typically, the droplet medium is an aqueous medium and the droplet is disposed in a hydrophobic medium and the concentration of amphipathic molecules is the concentration of amphipathic molecules in the hydrophobic medium.

Additionally or alternatively, when the droplets are formed, the aqueous medium of the droplets may comprise amphipathic molecules. The concentration of amphipathic molecules may therefore be the concentration of amphipathic molecules in the aqueous medium.

The container of the apparatus of the invention usually contains a bulk medium. When the droplet medium is an aqueous medium, the bulk medium is a hydrophobic medium. When the droplet medium is a hydrophobic medium, the bulk medium is an aqueous medium.

Typically, the droplet medium is an aqueous medium and the container of the apparatus of the invention contains a hydrophobic medium.

The hydrophobic medium may be selected from a wide range of materials. The hydrophobic medium may comprise a single hydrophobic compound. Alternatively, it may comprise a mixture of two or more different hydrophobic compounds. The hydrophobic medium can, for instance, be selected to affect the buoyancy of the droplet and the speed of formation of the layer of amphipathic molecules around at least part of the droplet after the droplet is first introduced into the hydrophobic medium.

The hydrophobic medium is typically an oil. The oil may be a single, pure, compound, or the oil may comprise a mixture of two or more compounds. It is usually desirable that the oil does not significantly destabilize any bilayers formed.

The oil may for instance comprise silicone oil (for instance poly phenyl methyl siloxane). The oil may consist of a single silicone oil, for instance poly phenyl methyl siloxane. Alternatively, the oil may comprise a mixture of two or more different silicone oils.

Any suitable silicone oil may be used. For instance, the oil may comprise silicon oil DC200 (a polymer comprising monomer units of —O—$Si(CH_3)_2$—), poly(dimethylsiloxane) (PDMS), hydroxy terminated, or PDMS 200. In some embodiments, the silicone oil is a poly(methylphenylsiloxane), such as AR20.

Additionally or alternatively, the oil may comprise a hydrocarbon. When the oil comprises a hydrocarbon it may comprise a single hydrocarbon compound, or a mixture of two or more hydrocarbons.

In some embodiments, the oil is a mixture comprising: (a) one or more hydrocarbons, and (b) one or more silicone oils. The hydrocarbon may, for instance, be any suitable liquid hydrocarbon. Whether a particular hydrocarbon is liquid will depend upon the temperature of the hydrophobic medium. Thus the term liquid hydrocarbon refers to a hydrocarbon that is a liquid at the temperature that the hydrophobic medium is at. Typically, the hydrophobic medium will be at room temperature. However, in some embodiments, the hydrophobic medium may be above or below room temperature.

In some embodiments, the oil may comprise a solid. A solid hydrocarbon may, for instance, be used in combination with a silicone oil. The oil may, for instance, be a mixture of solids that dissolve to form a liquid.

When the oil comprises a hydrocarbon, the hydrocarbon may be branched or unbranched, for example a hydrocarbon having from 5 to 40 carbon atoms, or from 5 to 30 carbon atoms (although hydrocarbons of lower molecular weight would require control of evaporation). Preferably, the hydrocarbon is a liquid at the operating temperature of the droplet used in the invention. Suitable examples include alkanes or alkenes, such as hexadecane, decane, pentane or squalene. Usually, the oil comprises a hydrocarbon.

Typically the hydrocarbon is an unsubstituted $C_{10}$-$C_{20}$ alkane, for instance hexadecane.

Shorter alkanes may be suitable, for instance, in assemblies for which buoyancy effects are less important and whose outer layer of amphipathic molecules, on at least part of the surface of the droplet, may form more quickly.

In some embodiments the hydrocarbon is a longer-chain hydrocarbon, such as unsubstituted $C_{15}$-$C_{40}$ alkane. For instance, an unsubstituted $C_{16}$-$C_{30}$ alkane chain, such as squalene.

In one embodiment, the hydrophobic medium comprises an unsubstituted $C_{10}$-$C_{20}$ alkane and the amphipathic molecules comprise one or more glycerophospholipids. For instance, the hydrophobic medium may comprise hexadecane and the outer layer of amphipathic molecules may comprise DPhPC.

Other types of oil are possible. For example the oil may be a fluorocarbon. This might be useful for the study of some systems, for example to minimise loss of a particular membrane protein or solute from the droplet assembly or to control the content of gases such as oxygen. Because fluorocarbons can be both hydrophobic and lipophobic, an oil phase that comprises fluorocarbons can usefully prevent the adhesion of a droplet assembly to surfaces.

In another embodiment, the hydrocarbon is a bromo-substituted $C_{10}$-$C_{30}$ alkane, or for instance a bromo-substituted $C_{10}$-$C_{20}$ alkane, e.g. bromododecane.

Typically, the oil comprises silicone oil or a hydrocarbon. Any suitable silicone oil may be employed. Usually, the silicone oil is as herein defined.

Silicone oil is advantageous on account of its density being close to that of water, which ensures that the droplet is approximately neutrally buoyant in water. The silicone oil may for instance be poly phenyl methyl siloxane, which has a density of about 1 g cm$^{-3}$.

The hydrocarbon typically has from 5 to 40 carbon atoms (a $C_5$-$C_{40}$ hydrocarbon), more typically from 10 to 30 carbon atoms (a $C_{10}$-$C_{30}$ hydrocarbon). Typically, it is an alkane or an alkene. Thus, the hydrocarbon may be a $C_5$-$C_{30}$ alkane, or a $C_{10}$-$C_{20}$ alkane. In another embodiment, the hydrocarbon may be a $C_5$-$C_{20}$ alkene, or a $C_{10}$-$C_{20}$ alkene. The hydrocarbon is typically unsubstituted. In one embodiment it is squalene. In a preferred embodiment, the hydrocarbon is an unsubstituted $C_5$-$C_{20}$ alkane, preferably an unsubstituted $C_{10}$-$C_{20}$ alkane.

The hydrocarbon may for instance be squalene, hexadecane or decane. However, in some embodiments the hydrocarbon may be substituted with a halogen atom, for instance bromine.

In some embodiments, the hydrophobic medium comprises a mixture of silicone oil and a hydrocarbon. Such mixtures have been found to provide advantageously short incubation times required for stable bilayers to be formed. The silicone oil and hydrocarbon in the mixture may be as further defined above. Typically, the hydrocarbon is an unsubstituted $C_{10}$-$C_{20}$ alkane, preferably hexadecane. The silicone oil usually has a density close to, but less than, that of water, to control the sinking rate of droplets during printing. When the droplet assembly is in a volume (such as a drop) of a hydrophobic medium, which volume is in a hydrophilic medium (such as an aqueous medium), the silicone oil typically has a density close to that of water to ensure the droplets in the droplet assembly have approximately neutral buoyancy in the hydrophilic medium.

The silicon oil may for instance be poly phenyl methyl siloxane. Usually, the volume ratio of the silicone oil to the hydrocarbon is equal or greater than 0.5:1. The volume ratio of the silicone oil to the hydrocarbon may for instance be from 0.5:1 to 5:1, for instance about 1:1. In some embodiments, the volume ratio of the silicone oil to the hydrocarbon is equal to or greater than 5:1.

The hydrophobic medium employed may, for instance, have a density close to that of water, for instance a density of less than or equal to about 1 g cm$^{-3}$.

In one embodiment, the hydrophobic medium comprises both silicone oil and hexadecane. Typically the silicone oil is poly phenyl methyl siloxane. The volume ratio of the silicone oil to the hexadecane is typically equal or greater than 0.5:1, for instance from 0.5:1 to 5:1. It may for instance be about 1:1. In some embodiments, the volume ratio of the silicone oil to the hydrocarbon is equal to or greater than 5:1.

Preferably, the hydrophobic medium comprises hexadecane. In some embodiments, the hydrophobic medium further comprises silicone oil.

Typically, the hydrophobic medium comprises hexadecane and the amphipathic molecules comprise DPhPC. More typically, the hydrophobic medium comprises hexadecane, the amphipathic molecules comprise DPhPC and the aqueous medium comprises an aqueous buffer solution.

The container of the apparatus of the invention may be any suitable container.

Typically, the container comprises a polymer, such as poly(methyl methacrylate). For instance, the container may comprise a well micromachined from said polymer.

In some embodiments, the bottom surface of the container comprises glass. At least one droplet of said plurality of droplets is typically in contact with the glass. The glass prevents the droplet from moving around.

In other embodiments, the bottom surface of the container comprises a polymer, such as poly(methyl methacrylate). For instance, when the apparatus of the invention is used to produce a self-folding droplet assembly (for instance a self-folding assembly as discussed below), at least one droplet of said plurality of droplets is typically in contact with a polymer. Droplets of the self-folding droplet assembly usually does not adhere to the polymer surface, allowing the droplet assembly to fold.

In a further embodiment, the container comprises a polymer such as polystyrene. For instance, the container may comprise polystyrene when the apparatus of the invention is used to produce a droplet assembly in which the aqueous droplets are in a drop of a hydrophobic medium which is in turn within a second bulk medium which is an aqueous medium. Such droplet assemblies are discussed below.

Typically, the container contains the bulk medium, which is a hydrophobic medium, and amphipathic molecules. Additionally or alternatively, the droplet generator may comprise the droplet medium, which is an aqueous medium, and amphipathic molecules.

Usually, the droplet generator in the apparatus of the invention contains the droplet medium. As mentioned hereinbefore, the droplet medium is typically an aqueous medium. The aqueous medium may, for instance, be as further defined herein. In some embodiments, the droplet generator contains an aqueous medium and a membrane protein. Usually, the membrane protein is in an aqueous solution. Additionally or alternatively, the bulk hydrophobic medium may comprise a membrane protein.

The membrane protein may be of any type. The use of integral membrane proteins has been demonstrated, but it is equally expected that peripheral membrane proteins could be used. The membrane protein may for instance be a membrane pump, channel and/or pore, to allow for precise control over the exchange of material, and electrical communication, between (i) individual droplets within the assembly and (ii) the droplet assembly and an external solution. The membrane protein could for instance be an α-hemolysin (αHL) pore, such as a staphylococcal α-hemolysin pore. However, any suitable membrane protein can be used including one from the two major classes, that is, β-barrels or α-helical bundles. An important application is a membrane protein which is a pore or a channel. Besides a protein pore or channel, further possible membrane proteins include, but not exclusively, a receptor, a transporter or a protein which effects cell recognition or a cell-to-cell interaction. The channel can be a voltage-gated ion channel, a light-sensitive channel such as bacteriorhodopsin, a ligand-gated channel or a mechano-sensitive channel.

Suitable membrane proteins which allow for exchange of materials and electrical communication are known and readily available to the skilled person; many such proteins are either commercially available or can be prepared by known methods. For instance, wild type (WT) αHL monomers can be prepared by in vitro transcription-translation (IVTT), and heptamerised by incubation with rabbit red blood cell membranes. The heptamers are typically purified by sodium dodecyl sulphate polyacrylamide gel electrophoresis (SDS-PAGE) (Maglia, G. et al., Method. Enzymol. 475, 591-623, (2010). Also, Bayley, H. et al., Droplet interface bilayers. Mol. BioSyst. 4, 1191-1208 (2008) lists several proteins that were tested for insertion into droplet interface bilayers made in bulk oil. Other suitable membrane protein include, but are not limited to, bacterial peptides and ionophores.

The membrane protein may, alternatively, be an engineered membrane protein or synthetic membrane protein. The engineered membrane protein may, for instance, be a genetically engineered protein, or a covalent or non-covalent chemically engineering protein. The synthetic membrane protein may, for instance, be a peptide or an organic molecule.

Droplets can exchange chemical species with each other through membrane proteins incorporated in the bilayer between the droplets. Suitable membrane proteins include, but are not limited to, pumps, channels and/or pores, receptor proteins, transporter proteins, and/or proteins which effect cell recognition or a cell-to-cell interaction, for instance an αHL pore. Other suitable membrane protein include, but are not limited to, bacterial peptides and ionophores. The membrane protein may, alternatively, be an engineered membrane protein or synthetic membrane protein.

Thus, a droplet assembly may be capable of trafficking materials such as chemical compounds through the network, from object to object, as well as to and from the external environment. A droplet assembly may, additionally or alternatively, be capable of transferring electrical signals from object to object, or to and from the external environment. Complex transport systems can be built up in this way. The transport system comprises a droplet assembly.

Chemical species such as water may be exchanged through the bilayer.

A droplet assembly may, for instance, act as a sensor module, capable of sensing the presence of a particular chemical in the external environment, for instance, or capable of sensing light. Thus, a droplet may comprise a sensor molecule. The sensor molecule can be present in the aqueous medium of the droplet or in a bilayer and may be any suitable sensor molecule. The sensor molecule may be a molecule which is sensitive to the presence of a particular chemical (for instance a target analyte), or it may be a light-sensitive molecule, or it may be sensitive to changes in pH or temperature. In some embodiments, the sensor molecule may be sensitive to the presence (or absence) of a particular biochemical or enzyme.

Typically, the membrane protein is α-hemolysin (αHL).

Usually, when present, the concentration of membrane proteins is equal to or greater than $0.1$ ng mL$^{-1}$, for instance, equal to or greater than $1$ ng mL$^{-1}$. For instance, the concentration of membrane proteins is equal to or greater than $2$ ng mL$^{-1}$, for instance, equal to or greater than $10$ ng mL$^{-1}$. The concentration of membrane proteins may, for instance, be from $0.1$ ng mL$^{-1}$ to $100$ mg mL$^{-1}$. Typically, the concentration of membrane proteins is from $0.1$ ng mL$^{-1}$ to $10$ mg mL$^{-1}$, for instance from $1$ ng mL$^{-1}$ to $5$ mg mL$^{-1}$. More typically, the concentration of membrane proteins is from $2$ ng mL$^{-1}$ to $1$ mg mL$^{-1}$, for instance, from $2$ ng mL$^{-1}$ to $0.1$ mg mL$^{-1}$. In some embodiments, the concentration of membrane proteins is about $10$ ng mL$^{-1}$.

Typically, the concentration of membrane proteins is the concentration of membrane proteins in the aqueous medium of the droplet, when the droplet is formed. When a droplet comprising a membrane protein is contacted with another droplet (which may or may not comprise a membrane protein), a bilayer of amphipathic molecules is formed at the interface. That bilayer typically comprises a membrane protein. Therefore membrane proteins initially in the aqueous medium may move to the bilayer.

Suitable concentrations of the membrane protein may depend on a number of factors. The rate of insertion of the membrane protein into the bilayer may, for instance, decrease with time. Typically, this will put a lower limit on the concentrations of the membrane protein that may be used.

Surfactants may be added to the aqueous medium. The surfactant may, for instance, be added to catalyse the movement of membrane proteins from the aqueous medium into the bilayer. Usually, the concentration of the surfactant added would not be high enough to destabilize the bilayers.

The concentration may also depend on the time it takes to print the droplet assembly. If, for instance, the number of droplets in the droplet assembly is reduced, the concentration of the membrane protein may be reduced also.

When the droplet is in contact with another droplet, the concentration of membrane proteins in the droplet and the other droplet may be the same or different. Further, when the droplet is part of a droplet assembly, the concentration of membrane proteins in each droplet of the droplet assembly may be the same or different.

Typically, at least one bilayer comprises a membrane protein. The bilayer at an interface between contacting droplets, may comprise more than one membrane protein. For instance, a particular bilayer may contain multiple copies of the same membrane protein, or two or more different classes of membrane proteins. Where more than one class is present, the bilayer may contain multiple copies of each different class.

Suitable membrane proteins which allow for exchange of materials and electrical communication are known and readily available to the skilled person; many such proteins are either commercially available or can be prepared by known methods. For instance, WT αHL monomers can be prepared by in vitro transcription-translation (IVTT), and heptamerised by incubation with rabbit red blood cell membranes. The heptamers are typically purified by sodium dodecyl sulphate polyacrylamide gel electrophoresis (SDS-PAGE) (Maglia, G. et al., Method. Enzymol. 475, 591-623, 2010). Also, Bayley, H. et al., Droplet interface bilayers. Mol. BioSyst. 4, 1191-1208 (2008) lists several proteins that were tested for insertion into droplet interface bilayers made in bulk oil. Other suitable membrane protein include, but are not limited to, bacterial peptides and ionophores.

The membrane protein may, alternatively, be an engineered membrane protein or synthetic membrane protein. The engineered membrane protein may, for instance, be a genetically engineered protein, or a covalent or non-covalent chemically engineering protein. The synthetic membrane protein may, for instance, be a peptide or an organic molecule.

A droplet may, in some embodiments, comprise other materials, compounds or substances. For instance, a droplet may comprise a small molecule, such as a dye, or a magnet. Suitable dyes include, but are not limited to, xylene cyanol FF, orange G, pyranine, fluorescein and 5-cTAMRA (5-carboxytetramethylrhodamine). Alternatively, a droplet may comprise any suitable sensor molecule, for instance a sensor molecule that it sensitive to a particular chemical or is a light-sensitive molecule, or it may be sensitive to changes in pH or temperature. In some embodiments, the sensor molecule may be sensitive to the presence (or absence) of a particular biochemical or enzyme. As a further alternative, a droplet may comprise a therapeutic agent, such as a prodrug, or a diagnostic agent, such as a contrast agent. A droplet may comprise an enzyme.

A droplet may comprise a living cell (or living cells), for example for use in tissue engineering. For instance, the cells may be allowed to grow inside the droplet after printing and/or to break down the bilayers between droplets after printing.

A droplet assembly, once printed, may be used as a template for the patterning of a solid material. The solid material may, for instance, be used in electronics, optics, photonics, or other material science applications. A droplet, or droplets, may, for instance, comprise inorganic materials that could diffuse between specific droplets. The inorganic materials may then react to form inorganic solids such as cadmium sulphide.

In the apparatus of the invention, the or each droplet generator is typically adapted to dispense droplets having a diameter of equal to or less than 1 mm, for instance, equal to or less than 200 μm.

Typically, the droplets are spherical droplets and the diameter is equal to the diameter of a sphere. When the droplets are not spherical droplets, the diameter of the droplet is equal to the diameter of a sphere that has the same volume as the droplet.

As discussed above, the droplet size may be controlled by a variety of factors such as the nozzle geometry, the voltage pulse amplitude and the duration of the voltage pulse.

Usually, the or each droplet generator is adapted to dispense droplets having a diameter of from 10 μm to 1 mm. The or each droplet generator may, for example, be adapted to dispense droplets having a diameter of from 10 μm to 200 μm, for instance, of from 30 μm to 60 μm. In some embodiments, the or each droplet generator is adapted to dispense droplets having a diameter of about 50 μm.

Typically, the or each droplet generator is adapted to dispense droplets having a volume of equal to or less than 2 μL.

In some embodiments, the or each droplet generator is adapted to dispense droplets having a volume of from 0.001 nL to 100 nL, for instance, from 0.005 nL to 0.5 nL.

Typically, the control unit is adapted to control the dispensing of droplets at a rate of at least $0.01\ s^{-1}$, for instance, $0.25\ s^{-1}$. Usually, the control unit is adapted to control the dispensing of droplets at a rate of at least $0.5\ s^{-1}$.

Usually, the control unit is adapted to control the dispensing of droplets at a rate of from 0.01 to $100\ s^{-1}$, for instance, from 0.01 to $50\ s^{-1}$. Typically, the control unit is adapted to control the dispensing of droplets at a rate of from 0.01 to $10\ s^{-1}$, for instance, from 0.25 to $5\ s^{-1}$. More typically, the control unit is adapted to control the dispensing of droplets at a rate of from 0.5 to $2.5\ s^{-1}$, for instance, from 0.75 to $2\ s^{-1}$. Usually, the control unit is adapted to control the dispensing of droplets at a rate of about $1\ s^{-1}$.

When there are two or more droplet generators, the rate at which droplets are dispensed is the rate at which droplets are dispensed from an individual droplet generator and not necessarily the overall rate at which droplets are dispensed. For example, if multiple droplet generators are used in parallel, the overall printing rate would typically be approximately equal to the rate at which droplets are dispensed from one droplet generator, multiplied by the number of generators.

The use of more than one droplet generator may thus significantly increase the overall printing rate.

In some embodiments, there may be a pause between the dispensing of one droplet and the dispensing of another droplet. The dispensing of droplets is discussed in more detail below, for the process of the invention. The printing patterns and algorithms used are also illustrated in the Examples, under Supplementary Methods.

Usually, the apparatus of the invention comprises a plurality of said droplet generators. For instance, the apparatus may comprise two or more droplet generators. Typically, the apparatus comprises from 1 to 20 droplet generators, for instance from 1 to 10 droplet generators. More typically, the apparatus comprises from 1 to 5 droplet generators, for instance, 2 or 3 droplet generators. In some embodiments, the apparatus comprises two droplet generators.

Typically, the control unit is adapted to control the dispensing of droplets from each droplet generator.

As discussed above, an advantage of the apparatus comprising a plurality of said droplet generators is that each droplet generator may comprise a different droplet medium (typically aqueous medium). This allows diverse droplet assemblies to be printed. The droplet assemblies may, for instance, comprise multiple compartments with different functionalities and/or complex communications systems that allow droplets within the assemblies to communicate with each other or with their external environment.

Accordingly, in some embodiments, when the apparatus comprises a plurality of said droplet generators, the apparatus usually comprises a first droplet generator comprising a first droplet medium and a second droplet generator comprising a second droplet medium, wherein the first and second droplet media are different. The first droplet medium is usually an aqueous medium as herein defined. The second droplet medium is typically also an aqueous medium as herein defined. Accordingly, in some embodiments, when the apparatus comprises a plurality of said droplet generators, the apparatus comprises a first droplet generator comprising a first aqueous medium and a second droplet generator comprising a second aqueous medium, wherein the first and second aqueous media are different. The first aqueous medium is usually an aqueous medium as herein defined. The second aqueous medium is typically an aqueous medium as herein defined.

In some embodiments, the first aqueous medium comprises a membrane protein and the second aqueous medium does not comprise said membrane protein. The membrane protein may, for instance, be a membrane protein as herein defined. The membrane protein may for instance be a membrane pump, channel and/or pore, to allow for precise control over the exchange of material, and electrical communication, between (i) individual droplets within the assembly and (ii) the droplet assembly and an external solution. The membrane protein could for instance be an αHL pore. However, any suitable membrane protein can be used including one from the two major classes, that is, β-barrels or α-helical bundles. Besides a protein pore or channel, further possible membrane proteins include, but not exclusively, a receptor, a transporter or a protein which effects cell recognition or a cell-to-cell interaction. The channel can be a voltage-gated ion channel, a light-sensitive channel such as bacteriorhodopsin, a ligand-gated channel or a mechano-sensitive channel. In some embodiments, the membrane protein is in an aqueous solution. Other suitable membrane protein include, but are not limited to, bacterial peptides and ionophores. The membrane protein may, alternatively, be an engineered membrane protein or synthetic membrane protein. The engineered membrane protein may, for instance, be a genetically engineered protein, or a covalent or non-covalent chemically engineering protein. The synthetic membrane protein may, for instance, be a peptide or an organic molecule.

In another embodiment, the first and second aqueous media may have different concentrations of a membrane protein. The membrane protein may for instance be a membrane pump, channel and/or pore, to allow for precise control over the exchange of material, and electrical communication, between (i) individual droplets within the assembly and (ii) the droplet assembly and an external solution. The membrane protein could for instance be an αHL pore. However, any suitable membrane protein can be used including the two major classes, that is, β-barrels or α-helical bundles. Besides a protein pore or channel, further possible membrane proteins include, but not exclusively, a receptor, a transporter or a protein which effects cell recognition or a cell-to-cell interaction. The channel can be a voltage-gated ion channel, a light-sensitive channel such as bacteriorhodopsin, a ligand-gated channel or a mechano-sensitive channel. Other suitable membrane protein include, but are not limited to, bacterial peptides and ionophores. The membrane protein may, alternatively, be an engineered membrane protein or synthetic membrane protein. The engineered membrane protein may, for instance, be a genetically engineered protein, or a covalent or non-covalent chemically engineering protein. The synthetic membrane protein may, for instance, be a peptide or an organic molecule.

In some embodiments, the first and second aqueous media have different osmolarities, or the first and second media comprise different concentrations of a salt or buffer. For instance, when the first aqueous medium comprises a membrane protein, the first and second aqueous media may have different osmolarities, or the first and second aqueous media may comprise different concentrations of a salt or buffer. In other embodiments, the first aqueous medium comprises a first salt and the second aqueous medium comprises a second salt, wherein the first salt and the second salt are different. The first salt may, for instance, be a chloride, such as potassium chloride, and the second salt may be a carbonate, such as potassium carbonate.

The ratio of the osmolarity of the first aqueous medium to the osmolarity of the second aqueous medium may be from 2:1 to 50:1, and is preferably from 5:1 to 20:1. In some embodiments, the ratio of the osmolarity of the first aqueous medium to the osmolarity of the second aqueous medium is from 5:1 to 15:1.

The ratio of the concentration of the salt or buffer in the first aqueous medium to the concentration of the salt or buffer in the second aqueous medium may be from 2:1 to 50:1, and is preferably from 5:1 to 20:1.

In some embodiments, the concentration of the salt or buffer in the first aqueous medium is from 100 mM to 1,000 mM and the concentration of the salt or buffer in the second aqueous medium is from 0.1 mM to 100 mM. Typically, the concentration of the salt or buffer in the first aqueous medium is from 150 mM to 750 mM and the concentration of the salt or buffer in the second aqueous medium is from 0.5 mM to 75 mM. More typically, the concentration of the salt or buffer in the first aqueous medium is from 150 mM to 500 mM and the concentration of the salt or buffer in the second aqueous medium is from 5 mM to 25 mM. For instance, the concentration of the salt or buffer in the first aqueous medium may be about 250 mM and the concentration of the salt or buffer in the second aqueous medium be about 25 mM.

Usually, the concentration of the salt or buffer in the first aqueous medium and the concentration of the salt or buffer in the second aqueous medium is a concentration of an alkali metal halide salt, such as potassium chloride. For instance, the buffer solution may comprise Tris-HCl and/or KCl.

When two droplets comprising different concentrations of a salt are placed in contact with each other, water will typically transfer from one droplet to the other. The inventors have used this process to their advantage by creating networks of droplets of different osmolarities. The transfer of water between the droplets causes deformation of the network as long as adhesion between droplets is maintained, as illustrated in FIG. 15. By controlling factors such as the difference in osmolarity of droplets in the network, the apparatus of the invention may be adapted to produce a droplet assembly that folds in a predictable way, referred to herein as a self-folding network or self-folding droplet assembly. The apparatus may, for instance, be adapted to produce a droplet assembly as defined herein below in the product of the invention.

When osmosis occurs between contacting droplets in the droplet assembly that comprise different aqueous media, the flow of water from one droplet to another will cause a change in the relative size of the two droplets. Therefore, two droplets may, for instance, have the same diameter when they first come into contact with each other but they may have different diameters after osmosis has taken place.

In the apparatus of the invention, a first droplet generator may be adapted to dispense droplets having a first diameter, and a second droplet generator may be adapted to dispense droplets having a second diameter, wherein the first and second diameters are the same or different. In some embodiments, the first and second diameters are the same, when the droplets first come into contact with each other. In other embodiments, the first and second diameters are the different, when the droplets first come into contact with each other.

As mentioned above, the or each droplet generator typically comprises a chamber for holding a droplet medium (typically an aqueous medium); an outlet; and a component for displacing a volume of said droplet medium through said outlet and thereby dispensing said volume as a droplet. When, the apparatus comprises a plurality of said droplet generators, the outlet of the first droplet generator may have the same diameter as the outlet of the second droplet generator or it may have a different diameter from the outlet of the second droplet generator.

In some embodiments, the control unit is adapted to coordinate (a) the movement of the container relative to the or each droplet generator and (b) the dispensing of the droplets, to create a said droplet assembly which comprises at least one layer of droplets, wherein each of said droplets comprises (i) a droplet medium and (ii) an outer layer of amphipathic molecules around the surface of the droplet medium, wherein the droplet medium is an aqueous medium or a hydrophobic medium and wherein each droplet in the layer contacts at least one other droplet in the layer to form a layer of said amphipathic molecules as an interface between contacting droplets.

The layer of said amphipathic molecules which is an interface between contacting droplets may, for instance, be a bilayer of said amphipathic molecules or a layer of a block copolymer. The layer of a block copolymer may, for example, be a layer of a triblock copolymer. When the droplet medium is an aqueous medium the layer of said amphipathic molecules which is an interface between contacting droplets may, for instance, be a bilayer of said amphipathic molecules or a layer of a block copolymer. When the droplet medium is a hydrophobic medium the layer of said amphipathic molecules which is an interface between contacting droplets may, for instance, be a bilayer of said amphipathic molecules or a layer of a block copolymer.

Usually, the layer of said amphipathic molecules which is an interface between contacting droplets is a bilayer of said amphipathic molecules.

Typically the droplet medium is an aqueous medium. Thus, in some embodiments, the control unit is adapted to coordinate (a) the movement of the container relative to the or each droplet generator and (b) the dispensing of the droplets, to create a said droplet assembly which comprises at least one layer of droplets, wherein each of said droplets comprises (i) an aqueous medium and (ii) an outer layer of amphipathic molecules around the surface of the aqueous medium, and wherein each droplet in the layer contacts at least one other droplet in the layer to form a bilayer of said amphipathic molecules as an interface between contacting droplets.

The aqueous medium is usually as defined herein. The aqueous medium may, for instance, be any suitable aqueous medium. For instance, the aqueous medium may be pure water, or an aqueous buffer solution, or an aqueous solution of one or more salts, or an aqueous solution comprising agarose and water.

The amphipathic molecules may be as further defined herein.

Usually, the control unit is adapted to coordinate (a) the movement of the container relative to the or each droplet generator and (b) the dispensing of the droplets, to create a said droplet assembly which comprises a plurality of said layers of said droplets, wherein each layer is disposed adjacent to another layer, so that droplets in a layer contact droplets in an adjacent layer to form layers of amphipathic molecules as interfaces between the contacting droplets.

The layer of said amphipathic molecules which is an interface between contacting droplets may, for instance, be a bilayer of said amphipathic molecules or a layer of a block copolymer. The layer of a block copolymer may, for example, be a layer of a triblock copolymer. When the droplet medium is an aqueous medium the layer of said amphipathic molecules which is an interface between contacting droplets may, for instance, be a bilayer of said amphipathic molecules or a layer of a block copolymer. When the droplet medium is a hydrophobic medium the layer of said amphipathic molecules which is an interface between contacting droplets may, for instance, be a bilayer of said amphipathic molecules or a layer of a block copolymer.

Typically, the layer of said amphipathic molecules which is an interface between contacting droplets is a bilayer of said amphipathic molecules.

Usually, the control unit is adapted to coordinate (a) the movement of the container relative to the or each droplet generator and (b) the dispensing of the droplets, to create a said droplet assembly which comprises a plurality of said layers of said droplets, wherein one layer is deposited on another layer. Typically, the droplet assembly is built upwards in horizontal layers.

The droplet assembly may, for instance, comprise three or more layers. The number of layers of said droplets may, for instance, be equal to or greater than 5.

Typically, the number of layers of said droplets is equal to or greater than 10, for instance, equal to or greater than 15. More typically, the number of layers of said droplets is equal to or greater than 20. In some embodiments, the number of layers is from 10 to 50, for instance, from 20 to 30. The number of layers may, for instance be about 20 or about 28. In other embodiments, the number of layers of said droplets is equal to or greater than 50, for instance, equal to or greater than 100. The number of layers of said droplets may be equal to or greater than 500, for instance equal to or greater than 1,000. For instance, the number of layers of said droplets may be equal to or greater than 2,000, for instance equal to or greater than 4,000.

The apparatus of the invention may be used to form a first droplet assembly and a second droplet assembly. A third droplet assembly may be produced, which third droplet assembly comprises the first droplet assembly and the second droplet assembly. The first droplet assembly and the second droplet assembly may, for instance, be joined together by bilayers formed between at least one droplet of the first droplet assembly and at least one droplet of the second droplet assembly. It is not necessary for each droplet in the first droplet assembly to form a bilayer with each droplet of the second droplet assembly.

In some embodiments, the control unit is adapted to coordinate (a) the movement of the container relative to the or each droplet generator and (b) the dispensing of the droplets, to create a said droplet assembly which comprises a plurality of droplets, wherein each of said droplets comprises (i) an aqueous medium, and (ii) an outer layer of amphipathic molecules around the surface of the aqueous medium, and wherein each of said droplets contacts another of said droplets to form a bilayer of said amphipathic molecules as an interface between the contacting droplets, wherein the plurality of droplets comprises a first region of said droplets and a second region of said droplets, wherein each droplet in the first region contacts at least one other droplet in the first region to form a bilayer of said amphipathic molecules as an interface between the contacting droplets, and each droplet in the second region contacts at least one other droplet in the second region to form a bilayer of said amphipathic molecules as an interface between the contacting droplets, wherein the aqueous medium of the droplets in the first region is different from the aqueous medium of the droplets in the second region, and/or wherein the composition of the bilayers between droplets in the first region is different from the composition of the bilayers between droplets in the second region.

At least one droplet in the first region may, for instance, contact at least one droplet in the second region to form a bilayer of said amphipathic molecules as an interface between the contacting droplets. Typically, two or more interfaces between a droplet in the first region and a droplet in the second region are formed. There may be at least one droplet in the first region that does not form a bilayer with a droplet in the second region and/or at least one droplet in the second region that does not form a bilayer with a droplet in the first region.

In one embodiment, the aqueous medium of the droplets in the first region comprises a membrane protein and the aqueous medium of the droplets in the second region may not comprise said membrane protein; the aqueous media of the droplets in the first and second regions may have different concentrations of a membrane protein; the bilayers between droplets in the first region may further comprise a membrane protein, and the bilayers between droplets in the second region either may not comprise said membrane protein or may have a lower concentration of said membrane protein than the bilayers between droplets in the first region; the aqueous media of the droplets in the first and second regions may have different osmolarities; or the aqueous media of the droplets in the first and second regions may have different concentrations of a salt or buffer.

In one embodiment, the aqueous medium of the droplets in the first region comprises a first membrane protein and the aqueous medium of the droplets in the second region comprises a second membrane protein, where the first and second membrane proteins are different. The first and second membrane proteins may be membrane proteins as defined herein.

Typically, the droplet assembly produced by the apparatus of the invention comprises at least 100 of said droplets, each of which comprises (i) an aqueous medium and (ii) an outer layer of amphipathic molecules around the surface of the aqueous medium. More typically, the droplet assembly produced by the apparatus of the invention comprises at least 1,000 of said droplets, each of which comprises (i) an aqueous medium and (ii) an outer layer of amphipathic molecules around the surface of the aqueous medium. Even more typically, the droplet assembly produced by the apparatus of the invention comprises at least 10,000 of said droplets (for instance, 25,000), each of which comprises (i) an aqueous medium and (ii) an outer layer of amphipathic molecules around the surface of the aqueous medium.

In some embodiments, the number of droplets in the droplet assembly produced by the apparatus of the invention may be very large, for instance, at least 100,000. The number of droplets in the droplet assembly produced by the apparatus of the invention may be at least 1,000,000, for instance, at least 10,000,000. For instance, the number of droplets in the droplet assembly produced by the apparatus of the invention may be at least 1,000,000,000. In some embodiments, the number of droplets in the droplet assembly produced by the apparatus of the invention may be at least 10,000,000,000, for instance at least 50,000,000,000. If, for instance the droplet assembly is a cube comprising at least 4000 layers, the number of droplets in the droplet assembly produced by the apparatus of the invention may be at least 64 billion droplets.

The apparatus of the invention can therefore be adapted to produce a three-dimension droplet assembly with mm-scale geometries. The droplet assembly may, for instance, comprise at least 10,000 of said droplets, wherein each droplet has a diameter of from 10 μm to 1 mm, for instance, from 10 μm to 200 μm. Typically, each droplet has a diameter of from 30 μm to 60 μm, for instance, each droplet has a diameter of about 50 μm. The droplet assembly may be functionalised, for instance, through the use of membrane proteins in a selected region(s) of the assembly. Additionally or alternatively, the droplet assembly can be made to fold using osmosis.

The apparatus of the invention may be adapted to produce a three-dimension droplet assembly with cm-scale geometries, or larger.

Three-dimensional droplet assemblies may be gelled together to form a new droplet assembly. In this way, individual droplet assemblies may be used as building bricks, for instance, to form complex structures.

In some embodiments, the control unit is adapted to coordinate (a) the movement of the container relative to the or each droplet generator and (b) the dispensing of the droplets, to produce a droplet assembly by a process as defined below for the process of the invention.

In other embodiments, the control unit is adapted to coordinate (a) the movement of the container relative to the or each droplet generator and (b) the dispensing of the droplets, to produce a droplet assembly as defined below for the product aspect of the invention.

In some embodiments of the apparatus of the invention, when the container contains a hydrophobic medium, said hydrophobic medium is a drop of a hydrophobic medium within a second bulk medium which is an aqueous medium, and said container contains said second bulk medium which is an aqueous medium and the drop of the hydrophobic medium. The second bulk medium which is an aqueous medium may be the same or different from the aqueous media defined previously.

Usually, the drop of the hydrophobic medium further comprises a peripheral layer of amphipathic molecules around the surface of the drop, as an interface between the drop and the second bulk medium which is an aqueous medium. The amphipathic molecules may be the same amphipathic molecules as the amphipathic molecules in the outer layer of amphipathic molecules around the surface of the aqueous medium or they may be different amphipathic molecules. Typically, a bilayer of amphipathic molecules is formed at the surface of the drop. There may therefore be (i) droplet interface bilayers between droplets and (ii) bilayers between droplets and the surface of the drop. These bilayers allow communication (i) between droplets within the droplet assembly and (ii) between a droplet within the droplet assembly and the external environment.

The apparatus of the invention may be used in the process of the invention.

The invention also relates to a process for producing a droplet assembly using an apparatus for producing the droplet assembly, which droplet assembly comprises: a plurality of droplets, wherein each of said droplets comprises: (i) a droplet medium, and (ii) an outer layer of amphipathic molecules around the surface of the droplet medium, wherein the droplet medium is an aqueous medium or a hydrophobic medium, and wherein at least one of said droplets contacts another of said droplets to form a layer of said amphipathic molecules as an interface between the contacting droplets; which apparatus comprises: at least one droplet generator; a container which is moveable relative to the at least one droplet generator; and a control unit, which control unit is adapted to control the dispensing of droplets from the at least one droplet generator and the movement of the container relative to the at least one droplet generator; wherein said container of the apparatus contains a bulk medium, wherein: when the droplet medium is an aqueous medium the bulk medium is a hydrophobic medium, and when the droplet medium is a hydrophobic medium the bulk medium is an aqueous medium; which process comprises: (a) a plurality of dispensing steps, wherein each dispensing step comprises dispensing a droplet of the droplet medium from a said droplet generator into the bulk medium, in the presence of amphipathic molecules, and thereby forming in the bulk medium a droplet which comprises (i) said droplet medium and (ii) an outer layer of amphipathic molecules around the surface of the droplet medium; and (b) moving the container relative to the at least one droplet generator, to control the relative positioning of the droplets in the bulk medium.

The layer of said amphipathic molecules which is an interface between contacting droplets may, for instance, be a bilayer of said amphipathic molecules or a layer of a block copolymer. The layer of a block copolymer may, for example, be a layer of a triblock copolymer. When the droplet medium is an aqueous medium the layer of said amphipathic molecules which is an interface between contacting droplets may, for instance, be a bilayer of said amphipathic molecules or a layer of a block copolymer. When the droplet medium is a hydrophobic medium the layer of said amphipathic molecules which is an interface between contacting droplets may, for instance, be a bilayer of said amphipathic molecules or a layer of a block copolymer.

Typically, the layer of said amphipathic molecules which is an interface between contacting droplets is a bilayer of said amphipathic molecules.

The droplet medium is typically an aqueous medium and the bulk medium is typically a hydrophobic medium. Another embodiment is envisaged however in which the droplet medium is a hydrophobic medium and the bulk medium is an aqueous medium.

Usually, however, the droplet medium is an aqueous medium and the bulk medium is a hydrophobic medium, and the invention will generally be described hereinbelow in these terms. However, as the skilled person will appreciate, any of the embodiments of the invention described herein in those terms may also be performed "in reverse", using a hydrophobic medium as the droplet medium instead of an aqueous medium, and using an aqueous medium as the bulk medium instead of a hydrophobic medium.

The aqueous medium is typically an aqueous medium as further defined hereinbefore for the apparatus of the invention.

Typically, each of the plurality of droplets has a diameter of equal to or less than 1 mm, for instance, from 10 µm to 1 mm. Usually, each of the plurality of droplets has a diameter of from 10 µm to 200 µm, for instance, of from 30 µm to 60 µm. More typically, each of the plurality of droplets has a diameter of about 50 µm.

The amphipathic molecules may be any suitable amphipathic molecules. They may, for instance, be amphipathic molecules as defined hereinabove for the apparatus of the invention.

The amphipathic molecules may, for instance, be disposed in the aqueous medium or in the hydrophobic medium. Typically, the amphipathic molecules are disposed in the hydrophobic medium.

When the aqueous medium is dispensed into the hydrophobic medium in the presence of amphipathic molecules, an aqueous droplet forms, which droplet comprises (i) an aqueous medium and (ii) an outer layer of amphipathic molecules around the surface of the aqueous medium.

A droplet may, in some embodiments, comprise other materials, compounds or substances. For instance, a droplet may comprise a small molecule, such as a dye, or a magnet. Suitable dyes include, but are not limited to, xylene cyanol FF, orange G, pyranine, fluorescein and 5-cTAMRA (5-carboxytetramethylrhodamine). Alternatively, a droplet may comprise any suitable sensor molecule, for instance a sensor molecule that is sensitive to a particular chemical or is a light-sensitive molecule, or it may be sensitive to changes in pH or temperature. In some embodiments, the sensor molecule may be sensitive to the presence (or absence) of a particular biochemical or enzyme. As a further alternative, a droplet may comprise a therapeutic agent, such as a prodrug, or a diagnostic agent, such as a contrast agent. A droplet may comprise an enzyme.

A droplet may comprise a living cell (or living cells), for example for use in tissue engineering. For instance, the cells may be allowed to grow inside the droplet after printing and/or to break down the bilayers between droplets after printing.

A droplet assembly, once printed, may be used as a template for the patterning of a solid material. The solid material may, for instance, be used in electronics, optics, photonics, or other material science applications. A droplet, or droplets, may, for instance, comprise inorganic materials that could diffuse between specific droplets. The inorganic materials may then react to form inorganic solids such as cadmium sulphide.

The process may, for instance, comprise moving the container, to control the relative positioning of the droplets in the hydrophobic medium and/or moving the at least one droplet generator, to control the relative positioning of the droplets in the hydrophobic medium.

Usually, the container is a container as defined hereinabove for the apparatus of the invention.

The or each droplet generator may, for instance, be a droplet generator as defined hereinabove for the apparatus of the invention.

Typically, the control unit is a control unit as defined hereinabove for the apparatus of the invention. Usually, the control unit controls the dispensing steps, and the movement of the container relative to the at least one droplet generator.

Usually, the control unit coordinates the dispensing steps, and the movement of the container relative to the at least one droplet generator, to produce the droplet assembly.

Typically, moving the container relative to the at least one droplet generator comprises: moving the container relative to the at least one droplet generator to position at least one of said droplets adjacent to another of said droplets so that at least one of said droplets contacts another of said droplets to form a layer of said amphipathic molecules as an interface between the contacting droplets.

The layer of said amphipathic molecules which is an interface between contacting droplets may, for instance, be a bilayer of said amphipathic molecules or a layer of a block copolymer. The layer of a block copolymer may, for example, be a layer of a triblock copolymer. When the droplet medium is an aqueous medium the layer of said amphipathic molecules which is an interface between contacting droplets may, for instance, be a bilayer of said amphipathic molecules or a layer of a block copolymer. When the droplet medium is a hydrophobic medium the layer of said amphipathic molecules which is an interface between contacting droplets may, for instance, be a bilayer of said amphipathic molecules or a layer of a block copolymer.

Typically, the layer of said amphipathic molecules which is an interface between contacting droplets is a bilayer of said amphipathic molecules.

Moving the container relative to the at least one droplet generator typically comprises: moving the container relative to the at least one droplet generator to position each droplet adjacent to at least one other droplet.

Usually, the droplet assembly comprises said plurality of droplets and each of said droplets contacts another of said droplets to form a bilayer of said amphipathic molecules as an interface between the contacting droplets.

Moving the container relative to the at least one droplet generator may, for instance, comprise: moving the container relative to the at least one droplet generator to position each droplet adjacent to at least one other droplet, so that each of said droplets contacts another of said droplets to form a layer of said amphipathic molecules as an interface between contacting droplets.

The layer of said amphipathic molecules which is an interface between contacting droplets may, for instance, be a bilayer of said amphipathic molecules or a layer of a block copolymer. The layer of a block copolymer may, for example, be a layer of a triblock copolymer. When the droplet medium is an aqueous medium the layer of said amphipathic molecules which is an interface between contacting droplets may, for instance, be a bilayer of said amphipathic molecules or a layer of a block copolymer. When the droplet medium is a hydrophobic medium the layer of said amphipathic molecules which is an interface between contacting droplets may, for instance, be a bilayer of said amphipathic molecules or a layer of a block copolymer.

Typically, the layer of said amphipathic molecules which is an interface between contacting droplets is a bilayer of said amphipathic molecules.

Usually, moving the container relative to the at least one droplet generator comprises: moving the container relative to the at least one droplet generator between dispensing steps.

For instance, the process usually comprises (b) moving the container relative to the at least one droplet generator between at least two of the dispensing steps. In some embodiments, the process comprises (b) moving the container relative to the at least one droplet generator between at least 50% of the dispensing steps, for instance between at least 80%. The process may, for instance, comprises (b) moving the container relative to the at least one droplet generator between substantially all of the dispensing steps. For instance, the process may comprise comprises (b) moving the container relative to the at least one droplet generator between all of the dispensing steps.

Although it may necessary to move the container relative to the at least one droplet generator between dispensing steps, it is not always necessary to move the container relative to the at least one droplet generator between dispensing steps. For instance, when the same droplet generator dispenses two droplets, one directly after the other, where one droplet is to be dispensed directly on top of the other droplet, the container does not need to be moved relative to the droplet generator in order that the droplets be dispensed at the correct location. Similarly, two droplets may be dispensed one after the other from two different droplet generators and the positioning of the two droplet generators may be such that the container does not need to be moved relative to the two droplet generators in order that the droplets be dispensed at the correct location.

In some embodiments, moving the container relative to the at least one droplet generator comprises: moving the container relative to the at least one droplet generator between dispensing steps and during dispensing steps.

For instance, the process may comprise (b) moving the container relative to the at least one droplet generator between and during at least two of the dispensing steps. The process may, for instance, comprise (b) moving the container relative to the at least one droplet generator between and during at least 50% of the dispensing steps, for instance between and during at least 80%. In some embodiments, the process comprises (b) moving the container relative to the at least one droplet generator between and during substantially all of the dispensing steps, for instance between and during all of the dispensing steps.

Typically, the droplet medium is an aqueous medium and the bulk medium is a hydrophobic medium. Thus, usually, the process of the invention is a process for producing a droplet assembly using an apparatus for producing the droplet assembly, which droplet assembly comprises: a plurality of droplets, wherein each of said droplets comprises: (i) an aqueous medium, and (ii) an outer layer of amphipathic molecules around the surface of the aqueous medium, and wherein at least one of said droplets contacts another of said droplets to form a bilayer of said amphipathic molecules as an interface between the contacting droplets; which apparatus comprises: at least one droplet generator; a container which is moveable relative to the at least one droplet generator; and a control unit, which control unit is adapted to control the dispensing of droplets from the at least one droplet generator and the movement of the container relative to the at least one droplet generator; wherein said container of the apparatus contains a hydrophobic medium; which process comprises: (a) a plurality of dispensing steps, wherein each dispensing step comprises dispensing a droplet of an aqueous medium from a said droplet generator into the hydrophobic medium, in the presence of amphipathic molecules, and thereby forming in the hydrophobic medium a droplet which comprises (i) said aqueous medium and (ii) an outer layer of amphipathic molecules around the surface of the aqueous medium; and (b) moving the container relative to the at least one droplet generator, to control the relative positioning of the droplets in the hydrophobic medium.

Typically, the process of the invention comprises: (a) a first dispensing step, comprising dispensing a droplet of an aqueous medium from a said droplet generator into the hydrophobic medium, in the presence of amphipathic molecules, and thereby forming in the hydrophobic medium a first droplet, which first droplet comprises (i) said aqueous medium and (ii) an outer layer of amphipathic molecules around the surface of the aqueous medium; (b) moving the container relative to the at least one droplet generator, to control the positioning of a second droplet in the hydrophobic medium relative to the first droplet in the hydrophobic medium; and (c) a second dispensing step, comprising dispensing a droplet of an aqueous medium from a said droplet generator into the hydrophobic medium, in the presence of amphipathic molecules, and thereby forming in the hydrophobic medium a second droplet, which second droplet comprises (i) said aqueous medium and (ii) an outer layer of amphipathic molecules around the surface of the aqueous medium.

The droplet generator of the first dispensing step may be the same droplet generator as the droplet generator of the second dispensing step or it may be a different droplet generator.

As mentioned above, for the apparatus of the invention, the size of the droplet may be controlled by, for example, the droplet generator from which it is dispensed. When the droplet generator of the first dispensing step is different from the droplet generator of the second dispensing step, the first droplet may have the same diameter as the second droplet or it may have a different diameter.

Typically, the diameter of the first droplet will be equal to or less than 1 mm, for instance, from 10 μm to 1 mm. Usually, the diameter of the first droplet will be from 10 μm to 200 μm, for instance, of from 30 μm to 60 μm. More typically, the diameter of the first droplet will be about 50 μm.

Usually, the diameter of the second droplet will be equal to or less than 1 mm, for instance, from 10 μm to 1 mm. Typically, the diameter of the second droplet will be from 10 μm to 200 μm, for instance, of from 30 μm to 60 μm. In some embodiments, the diameter of the second droplet is about 50 μm.

The aqueous medium of the first droplet may be the same as the aqueous medium of the second droplet or it may be different. When the droplet generator of the first dispensing step is the same as the droplet generator of the second dispensing step, the aqueous medium of the first droplet is typically the same as the aqueous medium of the second droplet. When the droplet generator of the first dispensing step is different from the droplet generator of the second dispensing step, the aqueous medium of the first droplet may, for instance, be different to the aqueous medium of the second droplet.

The amphipathic molecules of the first droplet may be the same as the amphipathic molecules of the second droplet or they may be different. Typically, the amphipathic molecules are amphipathic molecules as defined herein for the apparatus of the invention.

In some embodiments, said (b) moving the container relative to the at least one droplet generator comprises: moving the container relative to the at least one droplet generator so that the second droplet is positioned adjacent to the first droplet, so that the first and second droplets contact one another to form a bilayer of said amphipathic molecules as an interface between the contacting droplets.

Typically, the process further comprises: (d) moving the container relative to the at least one droplet generator, to control the positioning of a further droplet in the hydrophobic medium relative to the other droplets in the hydrophobic medium; and (e) a further dispensing step, comprising dispensing a droplet of an aqueous medium from a said droplet generator into the hydrophobic medium, in the presence of amphipathic molecules, and thereby forming in the hydrophobic medium a further droplet, which further droplet comprises (i) said aqueous medium and (ii) an outer layer of amphipathic molecules around the surface of the aqueous medium.

The aqueous medium of the further droplet is usually an aqueous medium as further defined herein.

Typically, the amphipathic molecules are amphipathic molecules as defined herein for the apparatus of the invention.

Usually, said (d) moving the container relative to the at least one droplet generator, comprises: moving the container relative to the at least one droplet generator so that the further droplet is positioned adjacent to at least one other droplet in the hydrophobic medium, so that the further droplet contacts at least one other droplet in the hydrophobic medium to form a bilayer of said amphipathic molecules as an interface between the contacting droplets.

In some embodiments, the process of the invention comprises at least 500 of said further dispensing steps (e). Typically, the process comprises 1,000 of said further dispensing steps (e), for instance, 5,000 of said further dispensing steps (e). For instance, the process may comprise at least 10,000 of said further dispensing steps (e). In some embodiments, the process comprises at least 25,000 of said further dispensing steps (e).

Usually, the process comprises at least 500 of said steps of (d) moving the container relative to the at least one droplet generator, and at least 500 of said further dispensing steps (e). For instance, the process may comprise at least 1,000 of said steps of (d) moving the container relative to the at least one droplet generator, and at least 1,000 of said further dispensing steps (e). In some embodiments, the process may, for instance, comprise at least 5,000 of said steps of (d) moving the container relative to the at least one droplet generator, and at least 5,000 of said further dispensing steps (e).

Typically, the process comprises at least 10,000 of said steps of (d) moving the container relative to the at least one droplet generator, and at least 10,000 of said further dispensing steps (e). In some embodiments, the process comprises at least 25,000 of said steps of (d) moving the container relative to the at least one droplet generator, and at least 25,000 of said further dispensing steps (e).

The process may comprise at least 1,000,000 of said steps of (d) moving the container relative to the at least one droplet generator, and at least 1,000,000 of said further dispensing steps (e). For instance, the process may comprise at least 1,000,000,000 of said steps of (d) moving the container relative to the at least one droplet generator, and at least 1,000,000,000 of said further dispensing steps (e).

Usually, the plurality of dispensing steps comprises dispensing steps which together produce a row of said droplets in the hydrophobic medium, wherein each droplet in the row contacts another droplet in the row to form a bilayer of said amphipathic molecules as an interface between contacting droplets.

Typically, the number of droplets in the row is at least 5, for instance, at least 10. More typically, the number of droplets in the row is at least 20, for instance, at least 50. Usually, the number of droplets in the row is from 5 to 500, for instance, from 10 to 250. In some embodiments, the number of droplets in the row is from 20 to 100. For instance, the number of droplets in the row may be from 20 to 35.

In some embodiments, the number of droplets in the row is at least 500, for instance, at least 1,000. The number of droplets in the row may, for instance, be at least 2,000, for instance, at least 4,000. The number of droplets in the row may, for instance, be from 5 to 5,000.

A plurality of rows of droplets may be disposed adjacent to one another to form a layer. In a layer, the plurality of rows are typically in contact with one another, so that droplets in one row contact droplets in an adjacent row or rows to form bilayers of said amphipathic molecules as interfaces between contacting droplets in adjacent rows. A layer may for instance comprise at least 10 such rows disposed adjacent to one another, or for instance at least 20 such rows disposed adjacent to one another. In some embodiments, a layer comprises at least 50 such rows disposed adjacent to one another, or for instance at least 100 such rows disposed adjacent to one another. The number of droplets in the row may be as defined above. A rectangular layer may for instance be a layer of at least 20 droplets by at least 20 droplets (i.e. a layer of at least 20×20 droplets). However, each row need not be the same length, and so a variety of different layer shapes can be formed by disposing rows of different lengths adjacent to one another. Self-folding droplet assemblies, for instance, may comprise rows of different lengths, as discussed in the Examples section.

In some embodiments, the plurality of dispensing steps comprises: a first set of dispensing steps which together produce a first row of said droplets in the hydrophobic medium, wherein each droplet in the first row contacts another droplet in the first row to form a bilayer of said amphipathic molecules as an interface between contacting droplets; and a second set of dispensing steps which together produce a second row of said droplets in the hydrophobic medium, wherein each droplet in the second row contacts another droplet in the second row to form a bilayer of said amphipathic molecules as an interface between contacting droplets.

Typically, droplets in the second row are disposed adjacent to droplets in the first row, so that droplets in the first row contact droplets in the second row to form bilayers of said amphipathic molecules as interfaces between the contacting droplets.

Usually, the plurality of dispensing steps comprises dispensing steps which together produce a plurality of rows of said droplets in the hydrophobic medium, wherein each droplet in a row contacts at least one other droplet in the row to form a bilayer of said amphipathic molecules as an interface between contacting droplets, and wherein each row is disposed adjacent to another row, so that droplets in a row contact droplets in an adjacent row to form bilayers of amphipathic molecules as interfaces between the contacting droplets.

The number of rows disposed adjacent to one another may be as defined above.

In some embodiments, the plurality of dispensing steps comprises dispensing steps which together produce a layer of said droplets in the hydrophobic medium, wherein each droplet in the layer contacts at least one other droplet in the layer to form a bilayer of said amphipathic molecules as an interface between contacting droplets.

A layer generally comprises a plurality of rows of droplets disposed adjacent to one another, and in contact with one another, so that droplets in a row contact droplets in an adjacent row or rows to form bilayers of said amphipathic molecules as interfaces between contacting droplets. A layer may for instance comprise at least 20 such rows disposed adjacent to one another. The number of droplets in the row may be as defined above. Different rows in the layer may have different numbers of droplets and so the layer need not be rectangular, but may be any shape. For instance, a layer can be rectangular, circular, oval, diamond shaped, or any other two-dimensional shape. Also, a layer may have one or more gaps (i.e. places where no droplet is present) at a certain position or positions. Thus, a layer may for instance be ring-shaped, or frame-shaped. A layer which is rectangular may for instance be a layer of at least 20 droplets by at least 20 droplets (i.e. a 20×20 droplet layer). Typically, one layer is above or below another layer. Usually, the droplet assembly is built upwards in horizontal layers.

By disposing layers of droplets on top of one another, droplet assemblies having a wide variety of three-dimensional (3D) shapes can be constructed. One of the simplest 3D droplet assemblies has a cuboid shape. However, by disposing layers of different shapes on top of one another, a wide variety of other three-dimensional droplet assembly structures can be formed, such as, for instance, a droplet assembly having a pyramidal shape or for instance having the shape of a prism.

Typically, the plurality of dispensing steps comprises: a first set of dispensing steps which together produce a first layer of said droplets in the hydrophobic medium, wherein each droplet in the first layer contacts at least one other droplet in the first layer to form a bilayer of said amphipathic molecules as an interface between contacting droplets; and a second set of dispensing steps which together produce a second layer of said droplets in the hydrophobic medium, wherein each droplet in the second layer contacts at least one other droplet in the second layer to form a bilayer of said amphipathic molecules as an interface between contacting droplets.

Usually, droplets in the second layer are disposed adjacent to droplets in the first layer, so that droplets in the first layer contact droplets in the second layer to form bilayers of said amphipathic molecules as interfaces between the contacting droplets.

More typically, droplets in the second layer are disposed on droplets in the first layer, so that droplets in the first layer contact droplets in the second layer to form bilayers of said amphipathic molecules as interfaces between the contacting droplets.

Generally, the plurality of dispensing steps comprises dispensing steps which together produce a plurality of layers of said droplets in the hydrophobic medium, wherein each droplet in a layer contacts at least one other droplet in the layer to form a bilayer of said amphipathic molecules as an interface between contacting droplets, and wherein each layer is disposed adjacent to another layer, so that droplets in a layer contact droplets in an adjacent layer to form bilayers of amphipathic molecules as interfaces between the contacting droplets.

Usually, each layer is disposed adjacent to another layer, so that droplets in a layer contact droplets in another layer to form bilayers of amphipathic molecules as interfaces between the contacting droplets.

More typically, each layer is disposed on another layer, so that droplets in a layer contact droplets in another layer to form bilayers of amphipathic molecules as interfaces between the contacting droplets.

In some embodiments, droplets in a first layer contact droplets in second layer to form bilayers of amphipathic molecules as interfaces between the contacting droplets, but droplets within the second layer are not in contact with each other. This may occur if, for instance, the droplet in the second layer have a smaller diameter than droplet in the first layer. It may also occur if, for instance, gaps (i.e. spaces without droplets) are specifically left in the second layer.

The layer may, for instance, be on one layer and below another layer.

The number of layers of said droplets may, for instance, be equal to or greater than 5. Typically, the number of layers of said droplets is equal to or greater than 10, for instance, equal to or greater than 15. More typically, the number of layers of said droplets is equal to or greater than 20, for instance, equal to or greater than 25. In some embodiments, the number of layers of said droplets is equal to or greater than 50, for instance, equal to or greater than 100. In other embodiments, the number of layers is from 10 to 50, for instance, from 20 to 30.

In some embodiments, the number of layers is at least 500, for instance, at least 1,000. The number of layers may, for instance, be at least 2,000, for instance, at least 4,000. The number of layers may, for instance, be from 5 to 5,000.

The process of the invention therefore provides an effective process for producing droplet assemblies comprising a large number of droplets, that have, for instance, mm-scale geometries.

The process of the invention may be used to produce a three-dimension droplet assembly with cm-scale geometries, or larger.

As discussed in the Examples, under Supplementary Methods, the printing pattern used to produce the droplet assembly can be controlled to control the accuracy of the assemblies that are printed. For instance, when the container is moved relative to the at least one droplet generator, the motion can cause displacement of droplets that have been recently dispensed. When, for instance, the tip of the droplet generator is immersed in a hydrophobic medium, the movement of the tip relative the hydrophobic medium creates a drag force. It may, for example, be advantageous to allow recently-dispensed droplets enough time to come into contact with another droplet before the container is moved relative to the at least one droplet generator. However, if too many pauses are built into the process, a large assembly comprising thousands of droplets may take a very long time to produce. The inventors have found that, in some embodiments, a pause after the printing of each row can allow a significant reduction in printing time without a significant cost to print quality (see Supplementary Discussion).

There are several ways in which the overall printing rate may be controlled. The overall printing rate may, for example, be controlled by dispensing droplets from two or more droplet generators simultaneously.

An individual droplet may be displaced by movement of the droplet generator relative to the container. It may therefore be desirable to allow each droplet, or at least each row of droplets, to reach its intended position in the network before the droplet generator is moved relative to the container. The printing rate could be changed by making droplets sink more quickly, which could be achieved by: (i) decreasing the viscosity of the hydrophobic medium; (ii) decreasing the density of the hydrophobic medium; (iii) increasing the density of the aqueous medium; or (iv) increasing the diameter of the droplets dispensed from the or each droplet generator. For example, lowering the viscosity of the hydrophobic medium would decrease the displacement of the droplet caused by the relative motion of the droplet generator to the container and increase the sink rate. Typically, this will mean the droplet generator can be moved to the next position more quickly.

Alternatively, the printing rate may be changed by increasing or decreasing the distance between the tip of the or each droplet generator and the position at which the droplet is to come to rest.

In one embodiment, each droplet is dispensed at least 100 μm, for instance, at least 150 μm, above the position at which it is to come to rest. Typically, each droplet is dispensed at least 200 μm above the position at which it is to come to rest. The inventors have found that when droplet production is attempted at smaller distances that these, droplet formation may be hindered. However, the smaller distances may be suitable if, for example, the viscosity or density of the hydrophobic medium is changed, or the density of the aqueous medium is changed.

The outer layer of amphipathic molecules to needs form before the dispensed droplet comes into contact with another droplet. This can be controlled by, for example: (a) increasing the concentration of amphipathic molecules in the hydrophobic medium or the aqueous medium; (b) decreasing the diameter of the droplet; or (c) using a hydrophobic medium that encourages rapid monolayer formation. The inventors have found that rapid monolayer formation may be encouraged when the hydrophobic medium comprises a silicon oil and/or a hydrocarbon such as hexadecane. The monolayer may, for instance, form within about 1 s of droplet formation.

Typically, the process of the invention further comprises a delay, between a dispensing step and a step of moving the container relative to the at least one droplet generator, for reducing droplet slippage.

Usually, the delay is equal to or greater than 1 ms, for instance, equal to or greater than 10 ms. Typically, the delay is equal to or greater than 25 ms, for instance, equal to or greater than 50 ms. For instance, the delay may be about 50 ms.

In some embodiments, the delay is after a row has been produced. The process may, for example, comprise: a first set of dispensing steps which together produce a first row of said droplets in the hydrophobic medium, wherein each droplet in the first row contacts another droplet in the first row to form a bilayer of said amphipathic molecules as an interface between contacting droplets; a second set of dispensing steps which together produce a second row of said droplets in the hydrophobic medium, wherein each droplet in the second row contacts another droplet in the second row to form a bilayer of said amphipathic molecules as an interface between contacting droplets; and a delay between the first set of dispensing steps and the second set of dispensing steps. Usually, the delay is equal to or greater than 1 second. For instance, the delay may be about 2 seconds.

In some embodiments, the plurality of dispensing steps may comprise at least one set of dispensing steps which together produce a row of said droplets in the hydrophobic medium, wherein each droplet in the row contacts another droplet in the row to form a bilayer of said amphipathic molecules as an interface between contacting droplets, and wherein the process further comprises a said delay between (i) the last dispensing step in the set of dispensing steps which together produce the row of said droplets, and (ii) a subsequent step of moving the container relative to the at least one droplet generator. Usually, the process further comprises said delay between the last dispensing step in each set of dispensing steps which together produce a row of said droplets, and a subsequent step of moving the container relative to the at least one droplet generator.

Typically, the hydrophobic medium, or the aqueous medium, or both, further comprise the amphipathic molecules. The amphipathic molecules are usually as defined herein for the apparatus of the invention.

In some embodiments, one or more additional droplets are dispensed at the end of a row. The one or more additional droplets may, for instance, prevent internal droplets in the droplet assembly from rolling out of their intended boundary.

Usually, the at least one droplet generator is a piezoelectric droplet generator which comprises a piezoelectric transducer for dispensing droplets, and wherein each dispensing step comprises the application of a voltage pulse to the piezoelectric component. The control unit typically controls the application of the voltage pulses to the piezoelectric component.

Typically, the voltage pulse has a peak-to-peak amplitude of from 5 V to 100 V, for instance, of from 20 V to 60 V.

Usually, each pulse has a duration of from 10 to 1,500 µs, for instance, of from 100 to 800 µs.

Typically, the voltage pulse is a square voltage pulse.

As shown in FIG. 10, the diameter of the droplet may be tuned by varying the amplitude and duration of the voltage pulses.

The process of the invention may further comprise applying small voltage pulses (e.g. from 6V to 18V voltage pulses, more typically approximately 12 V voltage pulses) periodically, e.g. approximately every ~10-30 s. Such pulses can advantageously ensure that the droplet medium (e.g. aqueous medium) does not gradually bud out of the tip of the printing nozzle and leak into the oil (since the aqueous chamber is typically placed higher than the oil container and can therefore exert greater hydrostatic pressure than the oil at the nozzle tip). It has been found that applying these low-voltage pulses can return the aqueous-oil interface at the nozzle tip to a planar geometry, without causing a droplet to be ejected.

Usually, the droplets are dispensed at a rate of from 0.01 to 100 $s^{-1}$, for instance, at a rate of from 0.01 to 50 $s^{-1}$. Typically, the droplets are dispensed at a rate of from 0.01 to 10 $s^{-1}$, for instance, of from 0.5 to 5 $s^{-1}$. In some embodiments, the droplets are dispensed at a rate of about 1 $s^{-1}$.

Typically, in the process of the invention, the apparatus comprises two or more of said droplet generators. As mentioned above, different droplet generators may dispense droplets having different diameters or droplets comprising different aqueous media.

In some embodiments, the droplet medium is an aqueous medium and the bulk medium is a hydrophobic medium, and the plurality of dispensing steps comprises: a first set of dispensing steps, which together produce a first region of said droplets in the hydrophobic medium, wherein each droplet in the first region contacts at least one other droplet in the first region to form a bilayer of said amphipathic molecules as an interface between contacting droplets; and a second set of dispensing steps, which together produce a second region of said droplets in the hydrophobic medium, wherein each droplet in the second region contacts at least one other droplet in the second region to form a bilayer of said amphipathic molecules as an interface between contacting droplets.

As the skilled person will appreciate, entire regions are not usually printed sequentially. Indeed, for a given layer, the droplets of the first region for that particular layer are often printed together, followed by all the droplets of the second region in that particular layer. Printing of another layer may then commence, which may involve printing of further droplets for the first region and further droplets for the second region (not necessarily in that order). Thus, the dispensing steps of the first set do not necessarily all take place sequentially, and likewise the dispensing steps of the second set do not necessarily all take place sequentially. Also, the dispensing steps of the second set do not necessarily all take place after the dispensing steps in the first set, and vice versa.

The first and second regions can be virtually any two- or three-dimensional structure that can be made from droplets using the process of the invention.

Usually, the first region and/or the second region comprises at least 100 droplets, for instance at least 500 droplets. In some embodiments, the first region and/or the second region comprises at least 1,000 droplets, for instance at least 5,000 droplets.

The number of droplets in each of the first and second regions may be very large, for instance, at least 100,000. The number of droplets in each of the first and second regions may be at least 1,000,000, for instance, at least 10,000,000. For instance, the number of droplets in each of the first and second regions may be at least 1,000,000,000. In some embodiments, the number of droplets in each of the first and second regions may be at least 10,000,000,000, for instance at least 50,000,000,000.

Typically, in the process of the invention, the apparatus comprises a first droplet generator and a second droplet generator, wherein the droplets dispensed in said first set of dispensing steps are dispensed from the first droplet generator into the hydrophobic medium, and the droplets dispensed in said second set of dispensing steps are dispensed from the second droplet generator into the hydrophobic medium. As mentioned above, different droplet generators may dispense droplets having different diameters and/or droplets comprising different aqueous media.

Also, as mentioned above, entire regions are not always printed sequentially. Thus, for a given layer, the droplets of the first region for that particular layer are often printed together, followed by all the droplets of the second region in that particular layer. Printing of another layer may then commence, which may involve printing of further droplets for the first region and further droplets for the second region (not necessarily in that order). Thus, in the embodiment of the invention defined above, the dispensing steps of the first set do not necessarily all take place sequentially, and likewise the dispensing steps of the second set do not necessarily all take place sequentially. Also, the dispensing steps of the second set do not necessarily all take place after the dispensing steps in the first set, and vice versa.

Usually, droplets in the second region are disposed adjacent to droplets in the first region, so that droplets in the first region contact droplets in the second region to form bilayers of said amphipathic molecules as interfaces between the contacting droplets.

Typically some, but not all, of the droplets in the second region are disposed adjacent to droplets in the first region. Thus, typically only some of the droplets in the first region contact droplets in the second region to form bilayers. This will often be the case if the first and/or second region is a three-dimensional structure made up of a plurality of layers of droplets. In such cases, only droplets on the surface of the first region will be able to contact droplets in the second region.

Usually, the first region of droplets comprises a row of droplets, part of a row of droplets, a plurality of rows of droplets, part of a plurality of rows of droplets, a layer of droplets, part of a layer of droplets, a plurality of layers of droplets, or part of a plurality of layers of droplets; and the second region of droplets comprises a row of droplets, part of a row of droplets, a plurality of rows of droplets, part of a plurality of rows of droplets, a layer of droplets, part of a layer of droplets, a plurality of layers of droplets, or part of a plurality of layers of droplets.

The first and second regions may be first and second rows as defined hereinabove. Additionally or alternatively, the first and second regions may be first and second layers as defined hereinabove.

In some embodiments, the first region of droplets forms a pathway of droplets through the second region of droplets. This is illustrated in FIG. 12.

In some embodiments, the aqueous medium of the droplets dispensed into the hydrophobic medium in said first set of dispensing steps further comprises a membrane protein, and wherein the aqueous medium of the droplets dispensed into the hydrophobic medium in said second set of dispensing steps does not comprise said membrane protein.

The membrane protein may be of any type. The membrane protein may for instance be a membrane pump, channel and/or pore, to allow for precise control over the exchange of material, and electrical communication, between (i) individual droplets within the assembly and (ii) the droplet assembly and an external solution. The membrane protein could for instance be an αHL pore. However, any suitable membrane protein can be used including one from the two major classes, that is, β-barrels or α-helical bundles. Besides a protein pore or channel, further possible membrane proteins include, but not exclusively, a receptor, a transporter or a protein which effects cell recognition or a cell-to-cell interaction. The channel can be a voltage-gated ion channel, a light-sensitive channel such as bacteriorhodopsin, a ligand-gated channel or a mechano-sensitive channel. Typically, the membrane protein is an α-hemolysin (αHL) pore.

Other suitable membrane protein include, but are not limited to, bacterial peptides and ionophores. The membrane protein may, alternatively, be an engineered membrane protein or synthetic membrane protein. The engineered membrane protein may, for instance, be a genetically engineered protein, or a covalent or non-covalent chemically engineering protein. The synthetic membrane protein may, for instance, be a peptide or an organic molecule.

Usually, the bilayers of amphipathic molecules formed between the contacting droplets in the first region further comprise said membrane protein.

In some embodiments, the bilayers of amphipathic molecules formed between contacting droplets in the second region do not comprise said membrane protein.

In other embodiments, the aqueous medium of the droplets dispensed into the hydrophobic medium in said first set of dispensing steps comprises a higher concentration of a membrane protein than the aqueous medium of the droplets dispensed into the hydrophobic medium in said second set of dispensing steps. The bilayers of amphipathic molecules formed between the contacting droplets in the first region may, for instance, comprise said membrane protein. Further, the bilayers of amphipathic molecules formed between the contacting droplets in the second region may not comprise said membrane protein or may comprise a lower concentration of said membrane protein than the bilayers of amphipathic molecules formed between the contacting droplets in the first region.

The membrane protein may be of any type. The membrane protein may for instance be a membrane pump, channel and/or pore, to allow for precise control over the exchange of material, and electrical communication, between (i) individual droplets within the assembly and (ii) the droplet assembly and an external solution. The membrane protein could for instance be an αHL pore. However, any suitable membrane protein can be used including one from the two major classes, that is, β-barrels or α-helical bundles. Besides a protein pore or channel, further possible membrane proteins include, but not exclusively, a receptor, a transporter or a protein which effects cell recognition or a cell-to-cell interaction. The channel can be a voltage-gated ion channel, a light-sensitive channel such as bacteriorhodopsin, a ligand-gated channel or a mechano-sensitive channel.

Other suitable membrane protein include, but are not limited to, bacterial peptides and ionophores. The membrane protein may, alternatively, be an engineered membrane protein or synthetic membrane protein. The engineered membrane protein may, for instance, be a genetically engineered protein, or a covalent or non-covalent chemically engineering protein. The synthetic membrane protein may, for instance, be a peptide or an organic molecule.

Typically, the membrane protein is an α-hemolysin (αHL) pore.

As discussed above, a droplet assembly can be made to fold as a consequence of osmosis. The folding process may bring droplets previously not in contact with each other into contact with each other. The folding process may, for instance, result in the formation of new bilayers of amphipathic molecules.

In some embodiments, in the process of the invention, the aqueous medium of the droplets dispensed into the hydrophobic medium in said first set of dispensing steps has a first osmolarity, and the aqueous medium of the droplets dispensed into the hydrophobic medium in said second set of dispensing steps has a second osmolarity, wherein the first osmolarity is greater than the second osmolarity; and droplets in the second region are disposed adjacent to droplets in the first region, so that droplets in the first region contact droplets in the second region to form bilayers of said amphipathic molecules as interfaces between the contacting droplets.

Typically, the aqueous medium of the droplets dispensed into the hydrophobic medium in said first set of dispensing steps is an aqueous solution of a salt, which aqueous solution has said first osmolarity, and the aqueous medium of the droplets dispensed into the hydrophobic medium in said second set of dispensing steps is an aqueous solution of a salt, which aqueous solution has said second osmolarity. In some embodiments, the aqueous medium of the droplets dispensed into the hydrophobic medium in said first set of dispensing steps is an aqueous solution of a first salt, which aqueous solution has said first osmolarity, and the aqueous medium of the droplets dispensed into the hydrophobic medium in said second set of dispensing steps is an aqueous solution of a second salt, which aqueous solution has said second osmolarity. The first and second salt may, for instance, be different salts or the same salts. The first salt may, for instance, be a chloride, such as potassium chloride, and the second salt may be a carbonate, such as potassium carbonate.

The ratio of the osmolarity of the first aqueous medium to the osmolarity of the second aqueous medium may be from 2:1 to 50:1, and is preferably from 5:1 to 20:1. In some embodiments, the ratio of the osmolarity of the first aqueous medium to the osmolarity of the second aqueous medium is from 5:1 to 15:1.

The extent to which a droplet assembly folds is typically determined by the osmolarity ratio and the geometry of the droplet network: for a given geometry. For instance, a network with a higher osmolarity ratio between the two droplet types may fold more rapidly than a network with a lower osmolarity ratio between the two droplet types.

The rate at which a droplet assembly folds it usually determined by the difference in osmolarities. Typically, the folding rate is proportional to the difference in osmolarities of the two droplets. For example, for a given ratio of osmolarities such as 10:1, a network in which the osmolyte concentrations are 1 M and 100 mM will fold approximately ten times more quickly than one in which the concentrations are 100 mM and 10 mM.

The rate of folding of the droplet assembly and the extend of folding may therefore be tuned.

The ability to tune the rate at which the droplet networks fold is important for the printing process. If the time taken to print a network is comparable to the time over which it folds, then parts of the network will move during printing and the object will therefore be printed incorrectly. In some embodiments, a large concentration ratio (to achieve large deformations) but a small concentration difference are used. This makes the folding time significantly slower than the printing time.

The rate of folding is also determined by the size of the droplets: for a given geometry, a network composed of larger droplets will usually fold more slowly. The folding rate is typically inversely proportional to the droplet diameter.

In some embodiments, the aqueous medium of the droplets dispensed into the hydrophobic medium in said first set of dispensing steps is an aqueous solution of a salt, which salt has a first concentration in the aqueous solution, and the aqueous medium of the droplets dispensed into the hydrophobic medium in said second set of dispensing steps is an aqueous solution of the same salt, which salt has a second concentration in the aqueous solution, wherein the first concentration is greater than the second concentration.

The ratio of the concentration of the salt or buffer in the first aqueous medium to the concentration of the salt or buffer in the second aqueous medium may be from 2:1 to 50:1, and is preferably from 5:1 to 20:1.

Typically, the concentration of the salt or buffer in the first aqueous medium is from 100 mM to 1,000 mM and the concentration of the salt or buffer in the second aqueous medium is from 0.1 mM to 100 mM. Typically, the concentration of the salt or buffer in the first aqueous medium is from 150 mM to 750 mM and the concentration of the salt or buffer in the second aqueous medium is from 0.5 mM to 75 mM. More typically, the concentration of the salt or buffer in the first aqueous medium is from 150 mM to 500 mM and the concentration of the salt or buffer in the second aqueous medium is from 5 mM to 25 mM. For instance, the concentration of the salt or buffer in the first aqueous medium may be about 250 mM and the concentration of the salt or buffer in the second aqueous medium may be about 25 mM.

Usually, the concentration of the salt or buffer in the first aqueous medium and the concentration of the salt or buffer in the second aqueous medium is a concentration of an alkali metal halide salt, such as potassium chloride. For instance, the buffer solution may for instance comprise Tris-HCl and/or KCl.

The process may, for instance, further comprises allowing water to transfer from the second region to the first region, to cause deformation of the droplet assembly. Typically, the transfer causes the first and second regions to curve or fold.

The deformation may, for instance, result in droplets previously not in contact with each other into, coming into contact with each other. The deformation may, for instance, result in the formation of new bilayers of amphipathic molecules.

The transfer typically occurs from one droplet to another, for instance, through the bilayer between contacting droplets. The transfer may, for instance, occur from at least one droplet in the second region to at least one droplet in the first region.

Typically, the first and second regions of droplets respectively comprise first and second layers of droplets are defined hereinabove, wherein the first and second layers are substantially rectangular and the transfer causes the first and second layers to fold into a substantially ring-shaped structure; the first layer is substantially rectangular and the second layer comprises parallel strips of droplets, and the transfer causes the first and second layers to fold into a substantially cylindrical structure; or the first and second layers comprise petal-shaped regions, and said transfer causes said petal-shaped regions to fold inwards and join to form a hollow droplet assembly.

More typically, the first and second regions of droplets respectively comprise first and second layers of droplets as defined hereinabove, wherein the first and second layers are substantially rectangular and the transfer causes the first and second layers to fold into a substantially ring-shaped structure; or the first and second layers comprise petal-shaped regions, and said transfer causes said petal-shaped regions to fold inwards and join to form a hollow droplet assembly.

When the first layer is substantially rectangular and the second layer comprises parallel strips of droplets, the formerly straight parallel strips typically form a ring (or rings) inside of the cylinder.

In some embodiments, the first and second regions of droplets respectively comprise first and second layers of droplets as defined hereinabove wherein the first and second layers comprise planar flower-shaped regions, and said transfer causes said planar flower-shaped regions to fold inwards and join to form a hollow droplet assembly. Typically, the hollow droplet assembly formed is spheroidal.

Usually, the first region comprises the first layer of droplets as defined hereinabove and at least one other layer of droplets.

Typically, the second region comprises the first layer of droplets as defined hereinabove and at least one other layer of droplets.

The term hollow refers to a volume within the droplet assembly that does not comprise a droplet. That volume may comprise a material or substance, for instance a therapeutic agent, such as a prodrug, or a diagnostic agent, such as a contrast agent, or an enzyme. In some embodiments, the volume comprises a living cell (or living cells), for example for use in tissue engineering. The volume may comprise an inorganic compound or material.

The hollow droplet assembly may, for instance, be substantially spherical.

The droplet assembly produced may, for instance, comprise a volume within the assembly that does not comprise any droplets.

In some embodiments, in the process of the invention, the droplet medium is an aqueous medium and the bulk medium is a hydrophobic medium and the apparatus comprises a first droplet generator and a second droplet generator, and the plurality of dispensing steps comprises: at least one dispensing step which comprises dispensing a droplet of a first aqueous medium from the first droplet generator into the hydrophobic medium, in the presence of amphipathic molecules, and thereby forming in the hydrophobic medium a said droplet which comprises (i) said first aqueous medium and (ii) an outer layer of amphipathic molecules around the surface of the aqueous medium; and at least one dispensing step which comprises dispensing a droplet of a second aqueous medium from the second droplet generator into the hydrophobic medium, in the presence of amphipathic molecules, and thereby forming in the hydrophobic medium a said droplet which comprises (i) said second aqueous medium and (ii) an outer layer of amphipathic molecules around the surface of the aqueous medium, wherein the first aqueous medium and the second aqueous medium are the same or different.

For instance, the aqueous medium may be pure water, or an aqueous buffer solution, or an aqueous solution of one or more salts, or an aqueous solution comprising agarose and water. Usually, the buffer solution comprises Tris-HCl and/or KCl. Alternatively, the aqueous medium may comprise a hydrogel.

Typically, the plurality of dispensing steps comprises a first plurality of said dispensing steps which comprise dispensing a droplet of a first aqueous medium from the first droplet generator into the hydrophobic medium, and a second plurality of said dispensing steps which comprise dispensing a droplet of a second aqueous medium from the second droplet generator into the hydrophobic medium.

Usually, the first aqueous medium is different from the second aqueous medium.

Typically, the first and second aqueous media have different osmolarities, or the first and second aqueous media comprise different concentrations of a salt or buffer.

For instance, the ratio of the concentration of the salt or buffer in the first aqueous medium to the concentration of the salt or buffer in the second aqueous medium may be from 2:1 to 50:1, and is preferably from 5:1 to 20:1.

Typically, the concentration of the salt or buffer in the first aqueous medium is from 100 mM to 1,000 mM and the concentration of the salt or buffer in the second aqueous medium is from 0.1 mM to 100 mM. Typically, the concentration of the salt or buffer in the first aqueous medium is from 150 mM to 750 mM and the concentration of the salt or buffer in the second aqueous medium is from 0.5 mM to 75 mM. More typically, the concentration of the salt or buffer in the first aqueous medium is from 150 mM to 500 mM and the concentration of the salt or buffer in the second aqueous medium is from 5 mM to 25 mM. For instance, the concentration of the salt or buffer in the first aqueous medium may be about 250 mM and the concentration of the salt or buffer in the second aqueous medium be about 25 mM.

Usually, the concentration of the salt or buffer in the first aqueous medium and the concentration of the salt or buffer in the second aqueous medium is a concentration of an alkali metal halide salt, such as potassium chloride. For instance, the buffer solution may comprise Tris-HCl and/or KCl.

In some embodiments, the first aqueous medium comprises a membrane protein and the second aqueous medium does not comprise said membrane protein. Alternatively, the first and second aqueous media may have different concentrations of a membrane protein.

In some embodiments the droplet or droplets of the first aqueous medium, which are dispensed by the first droplet generator, have a different size from the droplet or droplets of the second aqueous medium, which are dispensed by the second droplet generator. In other embodiments, the droplet or droplets of the first aqueous medium, which are dispensed by the first droplet generator, have the same size as the droplet or droplets of the second aqueous medium, which are dispensed by the second droplet generator.

As the skilled person will appreciate, when the droplet assembly produced by the process of the invention is a self-folding droplet assembly, the speed at which the assembly folds before the droplets of the assembly have all been dispensed, may affect the positioning of individual droplets. The folding of the assembly during the printing process should typically be minimised. Folding times may be lengthened, for instance, by reducing the difference in the concentration of the salt or buffer in different droplets or by increasing the size of the droplets. This is discussed further in the Examples, under Supplementary Discussion.

As mentioned for the apparatus of the invention, and as shown in FIG. 10, the diameter of the droplet may be tuned by varying the amplitude and duration of the voltage pulses. By varying these parameters, the droplet diameter can be tuned to a suitable diameter. The diameter may, for instance, be tuned between about 10 and 200 µm.

When, for instance, the aqueous medium is dispensed from the or each droplet generator by the application of a voltage pulse to the piezoelectric component, the voltage pulse may have a peak-to-peak amplitude of from 5 V to 100 V, for instance, of from 10 V to 80 V. The peak-to-peak amplitude may, for instance, be of from 20 V to 60 V. Typically, each pulse has a duration of from 10 to 1,500 µs, for instance, of from 50 to 1,000 µs. More typically, each pulse has a duration of from 100 to 800 µs. Usually, the voltage pulse is a square voltage pulse.

The droplet generator may also be adapted to control the droplet size. The or each droplet generator is typically a droplet generator as defined above for the apparatus of the invention. Typically, the outlet of the or each droplet generator has a diameter of less than 500 µm, for instance, of less than 250 µm. More typically, the outlet of the or each droplet generator has a diameter of less than 200 µm, for instance, of less than 150 µm. For instance, the outlet of the or each droplet generator typically has a diameter of from 20 µm to 200 µm, for instance from 60 µm to 120 µm. The outlet of the or each droplet generator may, for instance, have a diameter of about 100 µm.

Usually, the or each droplet generator further comprises a capillary attached to the chamber, wherein the tip of the capillary is said outlet. The tip of the capillary typically has a diameter of less than 150 µm. For instance the tip of the capillary may have a diameter of from 20 µm to 200 µm, for instance from 60 µm to 120 µm. The tip of the capillary may, for instance, have a diameter of about 100 µm.

As mentioned above, in the process of the invention, the droplet medium is usually an aqueous medium and the bulk medium is usually a hydrophobic medium. In some such embodiments, said hydrophobic medium is a drop of a hydrophobic medium.

The drop of the hydrophobic medium may, for instance, be within a second bulk medium which is an aqueous medium, wherein the container of the apparatus contains said second bulk medium which is an aqueous medium and the drop of hydrophobic medium.

Usually, the drop of the hydrophobic medium further comprises a peripheral layer of amphipathic molecules around the surface of the drop, as an interface between the drop and the second bulk medium which is an aqueous medium. The amphipathic molecules may be the same amphipathic molecules as the amphipathic molecules in the outer layer of amphipathic molecules around the surface of the aqueous droplet medium or they may be different amphipathic molecules. Typically, a bilayer of amphipathic molecules is formed at the surface of the drop. There may therefore be (i) droplet interface bilayers between droplets and (ii) bilayers between droplets and the surface of the drop. These bilayers allow communication (i) between droplets within the droplet assembly and (ii) between a droplet within the droplet assembly and the external environment.

Typically at least one droplet in the drop of the hydrophobic medium is in contact with the surface of the drop of the hydrophobic medium. A bilayer is typically formed at the point of contact. This separates the droplet from the second bulk medium which is an aqueous medium.

In some embodiments, the droplet assembly is produced within the drop of the hydrophobic medium, to produce a droplet encapsulate, which droplet encapsulate comprises: said drop of the hydrophobic medium; said peripheral layer of amphipathic molecules around the surface of the drop; and said droplet assembly within the peripheral layer.

The drop may, for instance, be suspended in a second bulk medium which is an aqueous medium. For instance, the drop may be suspended on a frame, such as a wire frame. Usually, the wire frame is coated with a hydrophobic coating.

Typically, the wire frame comprises a metal such as silver.

The hydrophobic coating on the wire frame usually comprises a polymer such as poly(methyl methacrylate). The coating may cover all of the wire frame or it may cover part of the wire frame. The coating may, for instance, cover the part of the wire frame that contacts the drop of a hydrophobic medium.

The wire frame may be any shape. For instance, the wire frame may comprise a circular loop.

The droplet encapsulate may, for instance, be stable for at least a week, for instance, at least two weeks. The stability of the droplet encapsulate means that they can functionalised and used for purposes such as communication with its surroundings through membrane pores, and for pH- or temperature-triggered release of contents.

Usually, when said hydrophobic medium is a drop of a hydrophobic medium, the process further comprises removing excess hydrophobic medium once the droplet assembly has been produced. Typically, the excess hydrophobic medium is removed using the or each droplet generator. More typically, the excess hydrophobic medium is removed by suction through the or each droplet generator. The removal of excess hydrophobic medium typically removes at least half of the hydrophobic medium, for instance at least 75% of the hydrophobic medium.

In some embodiments, the excess hydrophobic medium may be removed by allowing a portion of it to dissolve into the bulk hydrophilic phase. For instance, a volatile solvent, such as a short chain hydrocarbon may be added to the hydrophobic medium.

An encapsulate may comprise a droplet assembly comprising two or more compartments (i.e. a multi-compartment droplet assembly). The droplet assembly may, for instance, comprise a first compartment and a second compartment. The first compartment within the droplet assembly may communicate with the second compartment via membrane proteins. The first and/or second compartment may communicate with the external environment via membrane proteins. In principle, a droplet assembly may comprise a large number of different compartments and architecturally defined structures may thus be produced.

An encapsulate may comprise two or more droplet assemblies. Each droplet assembly may, for instance, be as defined herein.

In some embodiment individual droplet assemblies (such as three-dimensional droplet assemblies) may be gelled together to form a new droplet assembly. In this way, individual droplet assemblies may be used as building bricks, for instance, to form complex structures. The new droplet assembly formed may, for instance, be part of an encapsulate.

The process of the invention may further comprise recovering said droplet assembly from the bulk medium. When the bulk medium is a hydrophobic medium, the process of the invention may further comprise recovering said droplet assembly from the hydrophobic medium.

In the embodiments of the process of the invention in which a droplet assembly is produced within a drop of the hydrophobic medium, to produce a droplet encapsulate, the process of the invention may further comprise recovering said droplet encapsulate from the second bulk medium which is an aqueous medium.

Typically, in the process of the invention, the apparatus is as defined hereinabove for the apparatus of the invention.

The invention also relates to a droplet assembly which is obtainable by a process as defined hereinabove.

Further provided by the invention is a droplet assembly which comprises a plurality of droplets, wherein each of said droplets comprises (i) an aqueous medium, and (ii) an outer layer of amphipathic molecules around the surface of the aqueous medium, and wherein each of said droplets contacts another of said droplets to form a bilayer of said amphipathic molecules as an interface between the contacting droplets, wherein the plurality of droplets comprises a first region of said droplets and a second region of said droplets, wherein each droplet in the first region contacts at least one other droplet in the first region to form a bilayer of said amphipathic molecules as an interface between the contacting droplets, and each droplet in the second region contacts at least one other droplet in the second region to form a bilayer of said amphipathic molecules as an interface between the contacting droplets, wherein the aqueous medium of the droplets in the first region has a first osmolarity and the aqueous medium of the droplets in the second region has a second osmolarity, wherein the first osmolarity is different from the second osmolarity.

As mentioned above, the difference in osmolarity between the first osmolarity and the second osmolarity can cause a transfer of water between droplets of different osmolarity and result in the droplet assembly self-folding. The droplet assembly may, for instance, be designed to fold in a predictable way. Such self-folding droplet assemblies may find application in areas such as tissue engineering. By building artificial tissues, many of the disadvantages of using living cells are removed, for example, there would be no uncontrolled replication or migration of cells and limited rejection of the material in the body.

The aqueous medium may be any suitable aqueous medium. For instance, the aqueous medium may be pure water, or an aqueous buffer solution, or an aqueous solution of one or more salts. Alternatively, the aqueous medium may comprise a hydrogel. When the aqueous medium may comprise a hydrogel, the aqueous medium may, for instance, comprise agarose and water. The concentration of the agarose in water is typically less than or equal to 10% w/v agarose. For instance, the concentration of the agarose in said water may be from 0.25 to 5% w/v agarose. Hydrogels other than agarose may also be used. For instance the aqueous medium may comprise methylcellulose, polyethylene glycol diacrylate, polyacrylamide, matrigel, hyaluronan, polyethylene oxide, polyAMPS (poly(2-acrylamido-2-methyl-1-propanesulfonic acid)), polyvinylpyrrolidone, polyvinyl alcohol, sodium polyacrylate, acrylate polymers or poly(N-isopropylacrylamide). Alternatively, the aqueous medium body may comprise a silicone hydrogel or LB (Luria broth) agar.

One important property of the aqueous medium is pH and this can be varied over a wide range. In some embodiments, for instance, the pH of the aqueous medium within the aqueous droplet or droplets may be in the range of from 5 to 9 (or for instance in the range of from 6 to 8) although higher and lower pH values are also possible. The aqueous medium may therefore be an aqueous buffer solution. Any suitable buffer can be employed, depending on the desired pH. The buffer solution may for instance comprise Tris-HCl and/or KCl. In some embodiments the pH of the aqueous buffer solution is from 5 to 9, or for instance from 6 to 8. The nature and concentration of the solutes can be varied to vary the properties of the solution.

The aqueous medium of each droplet in the droplet assembly may be the same or different.

The amphipathic molecules may be any suitable amphipathic molecules. Typically, the amphipathic molecules are amphipathic molecules as defined above for the apparatus of the invention.

The droplet assembly may, for instance, be disposed in a hydrophobic medium. The hydrophobic medium may, for instance, be a hydrophobic medium as defined herein for the apparatus of the invention.

Typically, the droplet assembly comprises at least 100 of said droplets, each of which comprises (i) an aqueous medium and (ii) an outer layer of amphipathic molecules around the surface of the aqueous medium. More typically, the droplet assembly comprises at least 1,000 of said droplets, each of which comprises (i) an aqueous medium and (ii) an outer layer of amphipathic molecules around the surface of the aqueous medium. Even more typically, the droplet assembly comprises at least 10,000 of said droplets, each of which comprises (i) an aqueous medium and (ii) an outer layer of amphipathic molecules around the surface of the aqueous medium.

Usually, the first region and/or the second region comprises at least 100 droplets, for instance at least 500 droplets. In some embodiments, the first region and/or the second region comprises at least 1,000 droplets, for instance at least 50,00 droplets.

The number of droplets in each of the first and second regions may be very large, for instance, at least 100,000. The number of droplets in each of the first and second regions may be at least 1,000,000, for instance, at least 10,000,000. For instance, the number of droplets in each of the first and second regions may be at least 1,000,000,000. In some embodiments, the number of droplets in each of the first and second regions may be at least 10,000,000,000, for instance at least 50,000,000,000.

Usually, droplets in the second region are disposed adjacent to droplets in the first region, so that droplets in the first region contact droplets in the second region to form bilayers of said amphipathic molecules as interfaces between the contacting droplets.

Typically some, but not all, of the droplets in the second region are disposed adjacent to droplets in the first region. Thus, typically only some of the droplets in the first region contact droplets in the second region to form bilayers. This will often be the case if the first and/or second region is a three-dimensional structure made up of a plurality of layers of droplets. In such cases, only droplets on the surface of the first region will be able to contact droplets in the second region.

Usually, the ratio of the first osmolarity to the second osmolarity is from 2:1 to 50:1, preferably from 5:1 to 20:1.

In some embodiments, the aqueous medium of the droplets in the first region is an aqueous solution of a salt, which salt has a first concentration in the aqueous solution, and the aqueous medium of the droplets in the second region is an aqueous solution of the same salt, which salt has a second concentration in the aqueous solution, wherein the first concentration is different from the second concentration. Any suitable salt may be used, for instance an alkali metal halide, such as potassium chloride. In other embodiments, the aqueous medium of the droplets in the first region is an aqueous solution of a first salt, which salt has a first concentration in the aqueous solution, and the aqueous medium of the droplets in the second region is an aqueous solution of a second salt, which salt has a second concentration in the aqueous solution, wherein the first concentration is different from the second concentration. The first and second salt may be different salts. The first salt may, for instance, be a chloride, such as potassium chloride, and the second salt may be a carbonate, such as potassium carbonate.

Typically, the ratio of the first concentration to the second concentration is from 2:1 to 50:1, preferably from 5:1 to 20:1.

In some embodiments, the concentration of the salt or buffer in the first aqueous medium is from 100 mM to 1,000 mM and the concentration of the salt or buffer in the second aqueous medium is from 0.1 mM to 100 mM. Typically, the concentration of the salt or buffer in the first aqueous medium is from 150 mM to 750 mM and the concentration of the salt or buffer in the second aqueous medium is from 0.5 mM to 75 mM. More typically, the concentration of the salt or buffer in the first aqueous medium is from 150 mM to 500 mM and the concentration of the salt or buffer in the second aqueous medium is from 5 mM to 25 mM. For instance, the concentration of the salt or buffer in the first aqueous medium may be about 250 mM and the concentration of the salt or buffer in the second aqueous medium may be about 25 mM.

Usually, the concentration of the salt or buffer in the first aqueous medium and the concentration of the salt or buffer in the second aqueous medium is a concentration of an alkali metal halide salt, such as potassium chloride. For instance, the buffer solution may comprise Tris-HCl and/or KCl.

In the droplet assembly of the invention, typically, the droplets in the first region are arranged in a row, a plurality of rows, a layer or a plurality of layers, and the droplets in the second region are arranged in a row, a plurality of rows, a layer or a plurality of layers.

The first and second regions may be first and second rows as defined above for the process of the invention. Alternatively, the first and second regions may be first and second layers as defined above for the process of the invention.

For instance, the first region of droplets may comprise a row of droplets, part of a row of droplets, a plurality of rows of droplets, part of a plurality of rows of droplets, a layer of droplets, part of a layer of droplets, a plurality of layers of droplets, or part of a plurality of layers of droplets; and/or the second region of droplets may comprise a row of droplets, part of a row of droplets, a plurality of rows of droplets, part of a plurality of rows of droplets, a layer of droplets, part of a layer of droplets, a plurality of layers of droplets, or part of a plurality of layers of droplets.

In some embodiments, the first region of droplets forms a pathway of droplets through the second region of droplets. This is illustrated in FIG. 12.

In some embodiments, the bilayers of amphipathic molecules formed between the contacting droplets in the first region further comprise said membrane protein.

In some embodiments, the bilayers of amphipathic molecules formed between contacting droplets in the second region do not comprise said membrane protein.

In other embodiments, the aqueous medium of the droplets dispensed into the hydrophobic medium in said first set of dispensing steps comprises a higher concentration of a membrane protein than the aqueous medium of the droplets dispensed into the hydrophobic medium in said second set of dispensing steps. The bilayers of amphipathic molecules formed between the contacting droplets in the first region may, for instance, comprise said membrane protein. Further, the bilayers of amphipathic molecules formed between the contacting droplets in the second region may not comprise said membrane protein or may comprise a lower concentration of said membrane protein than the bilayers of amphipathic molecules formed between the contacting droplets in the first region.

The membrane protein may for instance be a membrane pump, channel and/or pore, to allow for precise control over the exchange of material, and electrical communication, between (i) individual droplets within the assembly and (ii) the droplet assembly and an external solution. The membrane protein could for instance be an $\alpha$HL pore. However, any suitable membrane protein can be used including one from the two major classes, that is, $\beta$-barrels or $\alpha$-helical bundles. Besides a protein pore or channel, further possible membrane proteins include, but not exclusively, a receptor, a transporter or a protein which effects cell recognition or a cell-to-cell interaction. The channel can be a voltage-gated ion channel, a light-sensitive channel such as bacteriorhodopsin, a ligand-gated channel or a mechano-sensitive channel.

Other suitable membrane protein include, but are not limited to, bacterial peptides and ionophores. The membrane protein may, alternatively, be an engineered membrane protein or synthetic membrane protein. The engineered membrane protein may, for instance, be a genetically engineered protein, or a covalent or non-covalent chemically engineering protein. The synthetic membrane protein may, for instance, be a peptide or an organic molecule.

Typically, the membrane protein is an $\alpha$-hemolysin ($\alpha$HL) pore.

As discussed above, a droplet assembly may fold as a consequence of osmosis.

In some embodiments, the droplets in the first region are arranged in a layer or a plurality of layers, and the droplets in the second region are arranged in a layer or a plurality of layers, wherein droplets in the second layer or plurality of layers are disposed adjacent to droplets in the first layer or plurality of layers, so that droplets in the first layer contact droplets in the second layer to form bilayers of said amphipathic molecules as interfaces between the contacting droplets.

In some embodiments, for instance, the droplets in the first region are arranged in a layer or a plurality of layers, and the droplets in the second region are arranged in a layer or a plurality of layers, wherein droplets in the second layer or plurality of layers are disposed on droplets in the first layer or plurality of layers, so that droplets in the first layer contact droplets in the second layer to form bilayers of said amphipathic molecules as interfaces between the contacting droplets.

The first and second layers or pluralities of layers may, for instance, comprise petal-shaped regions.

Usually, the petal-shaped regions are capable of folding inwards and joining to form a hollow droplet assembly. The hollow droplet assembly may be spheroidal.

In one embodiment, the first and second layers or pluralities of layers comprise flower-shaped regions. The flower-shaped regions may, for instance, be capable of folding inwards and joining to form a hollow droplet assembly. The hollow droplet assembly may be spheroidal.

The hollow droplet assembly may be substantially spherical.

As mentioned above, the term hollow refers to a volume within the droplet assembly that does not comprise a droplet. That volume may comprise a material or substance, for instance a therapeutic agent, such as a prodrug, or a diagnostic agent, such as a contrast agent, or an enzyme. The volume may comprise a living cell, or living cells. The volume may comprise an inorganic compound or material.

The hollow droplet assembly may, for instance, be substantially spherical.

The droplet assembly produced may, for instance, comprise a volume within the assembly that does not comprise any droplets.

The invention also relates to a droplet assembly which comprises a plurality of droplets, wherein each of said droplets comprises (i) an aqueous medium, and (ii) an outer layer of amphipathic molecules around the surface of the aqueous medium, and wherein each of said droplets contacts another of said droplets to form a bilayer of said amphipathic molecules as an interface between the contacting droplets, wherein the plurality of droplets defines a shell around a volume within the droplet assembly that does not comprise said droplets.

The aqueous medium may be any suitable aqueous medium. For instance, the aqueous medium may be pure water, or an aqueous buffer solution, or an aqueous solution of one or more salts. Alternatively, the aqueous medium may comprise a hydrogel. When the aqueous medium may comprise a hydrogel, the aqueous medium may, for instance, comprise agarose and water. The concentration of the agarose in water is typically less than or equal to 10% w/v agarose. For instance, the concentration of the agarose in said water may be from 0.25 to 5% w/v agarose. Hydrogels other than agarose may also be used. For instance the aqueous medium may comprise methylcellulose, polyethylene glycol diacrylate, polyacrylamide, matrigel, hyaluronan, polyethylene oxide, polyAMPS (poly(2-acrylamido-2-methyl-1-propanesulfonic acid)), polyvinylpyrrolidone, polyvinyl alcohol, sodium polyacrylate, acrylate polymers or poly(N-isopropylacrylamide). Alternatively, the aqueous medium body may comprise a silicone hydrogel or LB (Luria broth) agar.

One important property of the aqueous medium is pH and this can be varied over a wide range. In some embodiments, for instance, the pH of the aqueous medium within the aqueous droplet or droplets may be in the range of from 5 to 9 (or for instance in the range of from 6 to 8) although higher and lower pH values are also possible. The aqueous medium may therefore be an aqueous buffer solution. Any suitable buffer can be employed, depending on the desired pH. The buffer solution may for instance comprise Tris-HCl and/or KCl. In some embodiments the pH of the aqueous buffer solution is from 5 to 9, or for instance from 6 to 8. The nature and concentration of the solutes can be varied to vary the properties of the solution.

The aqueous medium of each droplet in the droplet assembly may be the same or different.

The amphipathic molecules may be any suitable amphipathic molecules. Typically, the amphipathic molecules are amphipathic molecules as defined above for the apparatus of the invention.

The droplet assembly may, for instance, be disposed in a hydrophobic medium. The hydrophobic medium may, for instance, be a hydrophobic medium as defined herein for the apparatus of the invention.

Typically, the droplet assembly comprises at least 100 of said droplets, each of which comprises (i) an aqueous medium and (ii) an outer layer of amphipathic molecules around the surface of the aqueous medium. More typically, the droplet assembly comprises at least 1,000 of said droplets, each of which comprises (i) an aqueous medium and (ii) an outer layer of amphipathic molecules around the surface of the aqueous medium. Even more typically, the droplet assembly comprises at least 10,000 of said droplets, each of which comprises (i) an aqueous medium and (ii) an outer layer of amphipathic molecules around the surface of the aqueous medium.

The volume that does not comprise any droplets may be completely enclosed by the shell, or it may be partially exposed.

The volume within the droplet assembly may comprise a bioactive agent. For instance it may comprise a therapeutic, such as a prodrug, and/or a diagnostic agent, such as a contrast agent, or an enzyme. The volume may comprise a living cell, or living cells.

Typically, the shell defined by said droplets is a curved structure.

Usually, the shell defined by said droplets is substantially cylindrical, substantially ring-shaped, substantially spherical, or substantially hemispherical.

In some embodiments, the shell defined by said droplets encloses said volume within the droplet assembly.

The shell defined by said droplets may, for instance, be substantially spherical.

Typically, in the droplet assembly of the invention, the number of said droplets in the plurality of droplets is at least 100, for instance, at least 500. In some embodiments, the number of said droplets in the plurality of droplets is at least 1000, for instance, at least 5000. For instance, number of said droplets in the plurality of droplets may be at least 10000 or at least 30000. For instance, the number of said droplets in the plurality of droplets may be about 35000.

The number of droplets in the plurality of droplets can in principle be very high, for instance of the order of millions. Such networks, which can in principle comprise millions of droplets, may, for instance, be useful for preparing protottissue (i.e. an aggregate of protocells). In some embodiments, therefore, the integer n may be as high as several million, for instance up to about 10,000,000, or for instance up to about 5,000,000.

The invention also relates to the use of a droplet assembly as defined herein in synthetic biology. For instance, use in preparing a protocell or an aggregate of protocells.

The invention also relates to the use of a droplet assembly as defined herein in tissue engineering. The droplet assembly may, for instance, be used to augment or replace failing tissues or organs. A droplet, or droplets, of the droplet assembly may comprise living cells. For instance, the cells may be allowed to grow inside the droplet after printing and/or to break down the bilayers between droplets after printing.

Also provided by the invention is the use of a droplet assembly as defined herein for the droplet assembly of the invention as a drug-delivery vehicle.

The invention also provides the use of a droplet assembly as defined herein for the droplet assembly of the invention in material science and engineering.

Further provided by the invention is the use of a droplet assembly as defined herein for the droplet assembly of the invention as a template for the patterning of a solid material. The solid material may, for instance, be used in electronics, optics, photonics, or other material science applications. A droplet, or droplets, may, for instance, comprise inorganic materials that could diffuse between specific droplets. The inorganic materials may then react to form inorganic solids such as cadmium sulphide.

The present invention is further illustrated in the Examples which follow:

EXAMPLES

General Methods

The lipid in all the Examples discussed below was 1,2-diphytanoyl-sn-glycero-3-phosphocholine (Avanti Polar Lipids) at 0.2-0.5 mg ml$^{-1}$. The oil was a 1:1 (v/v) mixture of hexadecane and silicone oil AR 20 (both from Sigma Aldrich). The buffer in all experiments was 25 mM Tris-HCl, 1 M KCl, 100 µM EDTA, pH 8.0, except in the folding experiments where this solution was diluted to obtain the salt concentrations given in the brief description of the figures section for to FIG. 15. The dyes used were xylene cyanol FF, orange G and pyranine (all from Sigma-Aldrich), at the concentrations given below, under Supplementary Methods.

Each droplet generator consisted of a piezoelectric transducer (7BB-20-6L0, Murata) affixed with epoxy adhesive onto a micromachined poly(methyl methacrylate) (PMMA) chamber (FIG. 3 and Supplementary Methods). The nozzle was formed from a glass capillary (Supplementary Methods) and fitted onto the chamber using a silicone rubber adapter (Drummond). The containers used for printing in bulk oil and bulk aqueous solution are described below, under Supplementary Methods.

The micromanipulator (PatchStar, Scientifica) was controlled by a computer. The same computer controlled the two droplet generators through a single Arduino Uno microcontroller board (SmartProjects), which through a digital-to-analog converter (AD5504, Analog Devices) and operational amplifier (OPA551, Texas Instruments) created an output voltage in the range −30 V to +30 V. The output voltage was applied through a relay (NRP-04, NCR) to one of the two transducers at a time (see also Supplementary Methods). Voltage pulses typically had a duration of 100-800 µs and a peak-to-peak amplitude of 20-60 V. The computer programs used to print networks in bulk oil and bulk aqueous solution are described below, under Supplementary Methods.

Heptameric αHL used in the electrical pathway experiments was prepared as described (Maglia, G. et al., Nano Lett. 9, 3831-3836 (2009)), and added to aqueous droplets at 100-fold dilution. The Ag/AgCl electrodes were prepared by treating 100-μm diameter silver wire (Sigma Aldrich) with 25% sodium hypochlorite solution for ≥1 h. Currents were measured with the electrodes by using a patch-clamp amplifier (Axopatch 200B, Axon Instruments) and a 16-bit digitizer (1322A, Molecular Devices). Signals were processed with a 5 kHz low-pass Bessel filter and acquired at 20 kHz. Results

Example 1

Droplet Generator

The automated production of droplet networks requires a reliable source of droplets of controlled size. The inventors built a piezoelectric droplet generator that employs a tapered glass capillary as a nozzle (see General Methods below). The device was filled with aqueous buffer and the nozzle tip immersed in a solution of lipids in oil. The diameter of droplets ejected into the oil by applying a voltage to the piezoelectric element (Supplementary Methods) could be tuned to between ~10 μm and 200 μm by varying the amplitude and duration of the voltage pulse (FIG. 10, Supplementary Discussion).

Example 2

Printing of a Network of Droplets Using Two Droplet Generators

Networks of heterologous droplets were printed by using two droplet generators.

Figure 2A:
FIG. 2a shows a schematic of a setup of the apparatus. Two droplet generators eject droplets of different aqueous solutions into a well filled with a solution of lipids in oil. The well is mounted on a motorized micromanipulator. The droplet generators and the manipulator are controlled by a personal computer (PC).
Figure 2B:
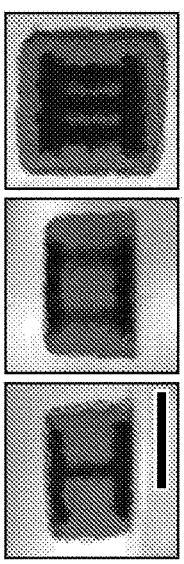
FIG. 2b provides a schematic of a droplet network being printed. Aqueous droplets ejected into the oil acquire a lipid monolayer, and form bilayers with droplets in the growing network.

The two nozzles were placed close together, and immersed in a bath of lipid-containing oil mounted on a motorized micromanipulator (FIG. 2a). The droplet generators and manipulator were controlled by a computer. A program was written that allowed designed three-dimensional networks to be printed automatically (Supplementary Methods). A network is defined by the user as a series of images that represent horizontal cross-sections one droplet thick. Based on these images, the program synchronizes the motion of the oil bath with the ejection of droplets from the two nozzles to build the network up in horizontal layers (FIG. 2b, Supplementary Methods).

Example 3

Printing of Millimetre-Sized Networks

In printing droplet networks, the inventors encountered challenges that do not arise in most two- and three-dimensional printing technologies (see also Supplementary Discussion). These are due to the relatively long time required for droplets to acquire a lipid monolayer, sink to their intended position, and form bilayers with other droplets. The time required for each of these processes is on the order of one second. Droplets that have not adhered to the printing substrate or formed bilayers with the growing network may be displaced from their intended positions, both by the ejection of further droplets and by viscous drag produced by the motion of the nozzles in the oil. Through the appropriate choice of fluids, nozzle geometry, droplet size and printing algorithm (Supplementary Discussion, Supplementary Methods), the inventors have printed precisely defined networks several millimetres in size, comprised of up to ~35,000 heterologous droplets of diameter ~50 μm ejected at a rate of ~1 $s^{-1}$ (FIGS. 2c-f).

Printed droplet networks are self-supporting (see for example FIG. 2f), and a thermodynamic analysis of the system indicates that stable networks can be printed with at least several thousand layers. The lattice of lipid bilayers also allows droplet networks to retain their shape under gentle perturbations; each bilayer lends an effective spring constant of ~4 mN/m to connected droplets, with a tensile strength of ~25 Pa. The inventors estimate that the Young modulus of the material is of the order of ~100-200 Pa for the conditions of the experiments. This range of stiffness overlaps with the elastic moduli of brain, fat and other soft tissues (Levental, I., Georges, P. C. and Janmey, P. A. Soft Matter 3, 299-306 (2007)).

Example 4

Printing Inside an Oil Droplet

The inventors have shown previously (Villar, G., et al, Nature Nanotech. 6, 803-808 (2011)) that droplet networks can be stabilized in bulk aqueous solution by encapsulation within small drops of oil, for prospective applications in synthetic biology and medicine. Whereas previously the encapsulated networks were created manually and therefore were limited in complexity, here the inventors demonstrate the printing of complex encapsulated networks. This was achieved by printing inside an oil drop suspended in aqueous solution (FIG. 11a) (Supplementary Methods, Supplementary Discussion). Once printing is complete, excess oil can be removed by suction through one of the printing nozzles. Encapsulated printed networks (FIGS. 11b-d) were stable for at least several weeks, and will therefore serve to expand the functions previously demonstrated with simple encapsulated networks, including communication with the aqueous surroundings through membrane pores, and pH- or temperature-triggered release of contents (Villar, G., et al., Nature Nanotech. 6, 803-808 (2011)).

Example 5

Droplet Assembly Comprising a Communication Pathway

Having demonstrated that droplet networks can be stabilized in bulk aqueous solution, the inventors aimed to further develop droplet networks as minimal analogues of functional tissue by printing networks with membrane proteins in specific interface bilayers. To this end, they printed a network in which only the droplets along a defined pathway contained staphylococcal α-hemolysin (αHL) (FIGS. 12a, b). The inventors determined whether protein pores inserted into bilayers along the pathway by electrical recording. To probe the network electrically in a non-destructive way, a drop of buffer of diameter ~500 μm containing αHL was manually pipetted onto each of two Ag/AgCl electrodes. The drops were then brought into contact with different parts of the network, so that they formed bilayers with the droplets on the network surface (FIG. 12a).

When the two large drops were placed on either end of the αHL-containing pathway (FIG. 12b), the inventors measured a stepwise increase in ionic current under an applied potential (FIG. 12c), caused by the insertion of αHL pores into the new bilayers. After one of the drops was separated and brought back into contact with the network away from the αHL-containing pathway (FIG. 12d), only transient currents were observed (FIG. 12e). When this drop was separated from the network again and replaced in its original position, a stepwise increase in current was again observed (data not shown). Droplet networks in which no droplets contained αHL showed negligible current flow, whereas the current measured across droplet networks in which every droplet contained αHL was similar to that shown in FIG. 12c (FIG. 13).

To facilitate the interpretation of these results, a formalism for the computational simulation of the electrical behaviour of complex droplet networks was developed (see Supplementary Methods below). The electrical model was found to be consistent with the measured currents exemplified in FIGS. 12c,e if most of the bilayers along the pathway contained several αHL pores, and the other bilayers in the network contained none (Supplementary Discussion), so that the pathway presented negligible electrical resistance compared to the rest of the network. The stepwise increase in current in FIG. 12c was therefore most likely caused by pore insertions in the bilayers between the pathway droplets and the large drops (Supplementary Discussion). The current spikes in FIG. 12e correspond to pore insertions in the bilayers between the drop placed away from the pathway and insulating droplets in the network (Supplementary Discussion). Each pore insertion in one of these bilayers reduces the resistance of that bilayer, which in turn increases the flow of ionic current through that bilayer. However, because each insulating droplet does not provide a route for ionic flow through its other bilayers, a net ionic charge accumulates in the droplet. This capacitive charging of the insulating layer of droplets produces a voltage that acts to eliminate the flow of ionic current. The current is therefore measured as a transient spike Based on these findings, the inventors have shown that droplet networks can be printed with protein pores in specific bilayers, and so allow the flow of ionic current along a defined pathway under an applied potential. In enabling rapid electrical communication along a path between two sites, the network presented here mimics the essential function of a nerve, but not its mechanism of signal propagation. More sophisticated networks with functional membrane channels or pores could exhibit more complex behaviour (Maglia, G. et al., Nature Nanotech. 4, 437-440 (2009)). For instance, a network might employ voltage-gated ion channels to generate and transmit an action potential along its length, or light-sensitive channels such as bacteriorhodopsin to mimic the function of the retina (Holden, M. A., et al., J. Am. Chem. Soc. 129, 8650-8655 (2007)).

Example 6

Folding Networks

A means to fold printed droplet networks into 3D forms that are not readily obtained by printing alone was also investigated. Water permeates readily through droplet interface bilayers even in the absence of protein channels or pores, with a permeability coefficient of $27\pm5$ μm s$^{-1}$ (mean±s.d., n=6) under the conditions of this study (FIG. 16, Supplementary Methods), consistent with other permeability measurements of droplet interface bilayers (Dixit, S. S., et al., Langmuir 28, 7442-7451 (2012) and Xu, J., et al., Adv. Mater. 22, 120-127 (2010)) and other lipid bilayer systems (Boroske, E., et al., Biophys. J. 34, 95-109 (1981)). Consequently, two droplets of higher and lower osmolarity joined by a DIB will respectively swell and shrink until their osmolarities are equal (FIG. 15a). By extension, water transfer between droplets in a network composed of droplets of different osmolarities will cause spontaneous deformation of the network as long as adhesion between droplets is maintained (FIG. 15b). Several prerequisites were found for droplet networks to fold in a predictable way (see also Supplementary Discussion). First, to prevent droplets from being printed onto incorrect positions in the network, the network must fold slowly compared to the printing time. Second, the swelling and shrinking of the two droplet types can produce a length mismatch between regions of connected droplets, and the induced stress can cause the network to buckle in an uncontrolled manner. This is analogous to the buckling instability in tissues that grow at inhomogeneous rates, such as certain leaves (Nath, U., et al., Science 299, 1404-1407 (2003) and Sharon, E., et al., Phys. Rev. E 75 (2007)) and flower petals (Liang, H. Y. & Mahadevan, L., Proc. Natl. Acad. Sci. USA 108, 5516-5521 (2011)), as well as in some synthetic systems (Klein, Y., et al., Science 315, 1116-1120 (2007) and Sharon, E., et al., Nature 419, 579-579 (2002)). In certain cases, the stress may instead cause connected droplets to separate and thereby prevent further folding of the network around the fracture zone.

These various problems can be solved through judicious choices of printing rate, salt concentrations and droplet size, and adjustments to the network geometry (see Supplementary Discussion). The final geometry of the network is then determined in a controlled way by its initial geometry, the distribution of the two types of droplets, and the ratio of their osmolarities. The inventors formulated a simple model that allows them to qualitatively predict the folding behaviour of a given droplet network (see Supplementary Methods below), and this model was used to design droplet networks that folded successfully.

In one experiment, the inventors printed a network that comprised two strips of droplets of different salt concentrations, connected along their lengths (FIG. 15c). The network folded spontaneously in the horizontal plane over ~3 h, until droplets in opposing ends of the network formed bilayers in a closed ring. They also programmed a network to fold spontaneously out of the horizontal plane to attain a geometry that would be difficult to print directly. A flower-shaped network with four petals was printed, in which the lower layers had higher osmolarity than the upper layers. The permeation of water from the upper into the lower layers induced a curvature that raised the petals and folded them inwards, in a manner that resembles the nastic movements exhibited by certain plants (Forterre, Y., et al., Nature 433, 421-425 (2005) and Skotheim, J. M. & Mahadevan, L., Science 308, 1308-1310 (2005)). The folded network had a near-spherical geometry, with the originally upper layer contained within a shell formed by the originally lower layer (FIGS. 15d,e). The evolution of the geometry of the network is in good qualitative agreement with that of a simulated folding network with similar initial conditions (FIG. 15f).

Other materials exist that deform through non-uniform volume changes. For instance, the function of the bimetallic strip relies on an inhomogeneous thermal expansion coefficient. Also, hydrogel systems have been spatially patterned to suffer inhomogeneous changes in volume as a function of solvent concentration or temperature (Kim, J., et al., Science 335, 1201-1205 (2012) and Hu, Z. B., et al., Science 269, 525-527 (1995)). Whereas these systems are driven by an external stimulus, droplet networks fold as a result of water transfer entirely within the network, and therefore do not require an external driving force.

Supplementary Methods

1 Dye Concentrations

This section details the dye concentrations for each network shown in FIGS. 2, 11, 12 and 15.

Figure 2C:
FIG. 2c shows images that define the desired horizontal cross-sections of a three-dimensional droplet network. The design comprises 20 layers of 50×35 droplets each; only alternate cross-sections are shown.
Figure 2D:
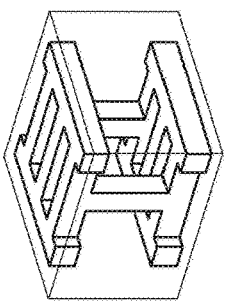
In FIG. 2d, a network printed according to the design in FIG. 2c is shown. The scale bar represents 5 mm.
Figure 2E:
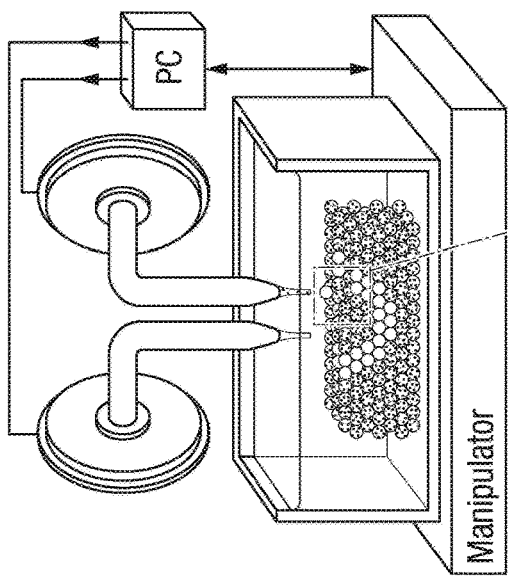
FIG. 2e is a schematic of another three-dimensional design, which consists of 28 layers of 24×24 droplets each.

FIG. 2d: Dark grey droplets contain 1 mM xylene cyanol FF.

Figure 2F:
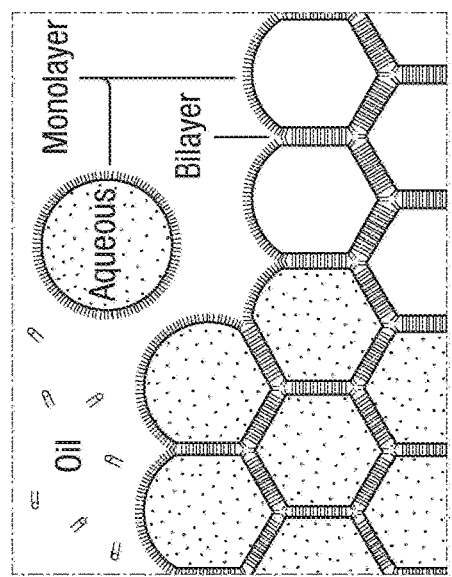
FIG. 2f shows three orthogonal views of a single network printed according to the design in FIG. 2e. The scale bar represents 1 mm.

FIG. 2f: Dark grey droplets contain 1 mM xylene cyanol FF, and light grey droplets contain 10 mM orange G.

FIG. 11b: Light grey droplets contain 900 µM xylene cyanol FF and 100 µM pyranine, and dark grey droplets contain 10 mM orange G.

FIGS. 12b-e: Light grey droplets and large dark grey drops contain 10 mM pyranine, and other droplets contain 50 µM xylene cyanol FF.

FIG. 15c: Dark grey droplets contain 320 µM xylene cyanol FF, and light grey droplets contain 2.5 mM orange G.

FIG. 15d: Dark grey droplets contain 160 µM xylene cyanol FF, and light grey droplets contain 800 µM orange G.

2 Containers

Networks Printed in Bulk Oil

The container for networks printed in bulk oil was a well micromachined from poly(methyl methacrylate) with a glass observation window on one side. The oil-filled volume was ~15×10 mm horizontally and ~5 mm deep. Spontaneously folding networks were printed directly on the bottom surface of the well, while all other networks in bulk oil were printed on a piece of glass coverslip placed in the well.

Networks Printed in Bulk Aqueous Solution

The container for networks printed in bulk aqueous solution was a polystyrene cuvette, with a glass coverslip bottom in the case of the network imaged by confocal microscopy.

Printing in bulk aqueous solution took place inside a drop of oil that was suspended on a wire frame, which was made as follows. Poly(methyl methacrylate) shavings were dissolved in chloroform at 100 mg ml$^{-1}$. One end of a 100-µm diameter silver wire (Sigma-Aldrich) was dipped in this solution up to five times, so that it acquired a thin hydrophobic coating. The coated end of the wire was then shaped into a loop using tweezers, such that the loop was the only length of the wire coated with polymer. The uncoated end was attached to the polystyrene container using epoxy adhesive.

To insert the printing nozzles into the oil drop, the nozzles first had to pass through the bulk aqueous phase. To prevent leakage of the nozzle contents into the bulk aqueous solution, a plug of the same oil mixture used for the oil drop was sucked into the tip of each nozzle, by applying suction at the inlet of each droplet generator with a micropipette. Once the nozzle tips had been placed inside the oil drop in aqueous solution, the oil plugs were expelled by applying positive pressure at each inlet using a micropipette.

3 Droplet Generator

Nozzle

The printing nozzle for each droplet generator was formed from a glass capillary (Drummond) with external and internal diameters of 1.4 mm and 1.0 mm, respectively. The capillary was pulled (PC-10, Narishige), and its pulled end trimmed by gently passing another pulled capillary tip against it (Oesterle, A. P-1000 & P-97 Pipette Cookbook (rev. G). Sutter Instrument Co., Novato (2011)) to give a flat-ended tip of diameter between ~60 µm and 120 µm. The capillary was then bent by 90° over a flame, ~15 mm from the pulled end. Finally, the capillary was trimmed ~35 mm from the pulled end (FIG. 3).

Filling

The chamber was filled with ~400 µl of aqueous solution through the inlet on the top of the device by using a micropipette with a gel-loading tip. The nozzle spontaneously filled with this solution through capillary action.

The volume of aqueous solution required for printing could be reduced to ~5 which minimized the wastage of solution in the experiments that employed αHL. To do this, the droplet generator was first filled with water. The nozzle of the generator was then immersed in a well filled with hexadecane, and suction was applied at the inlet of the generator by using a micropipette so that ~5 µl of hexadecane was drawn into the nozzle. The nozzle was then immersed into another well that contained the aqueous sample, and suction applied to load a similar volume of the aqueous solution. The hexadecane formed a plug within the nozzle that prevented the aqueous sample in the nozzle tip from mixing with the larger volume of water. For significantly smaller loadings of the aqueous sample, the size of ejected droplets was found to vary with the volume of aqueous sample remaining in the nozzle.

4 Driving Electronics for Droplet Generators

The electronic circuit built to drive the droplet generators is shown schematically in FIG. 4. The circuit interprets instructions from a computer to produce a square voltage pulse of specified duration and amplitude, and applies this voltage to the piezoelectric transducer, or piezo, in either of two droplet generators. This section describes how the circuit generates the voltage pulse.

Piezo Selection

First, the computer sends a serial message that represents the desired piezo to an Arduino microcontroller board. The microcontroller interprets this message, and activates a relay through a transistor such that the desired piezo will receive the voltage output of the circuit. Once a piezo is selected in this way, it is held at the maximum negative voltage of −30 V. The piezo terminal that is connected to the voltage output was chosen such that a negative voltage produces compression of the piezo.

Voltage Output

The computer then sends a serial message to the microcontroller that represents the instruction to generate a voltage pulse. The duration and amplitude of the pulse can be either specified in the serial message or previously programmed into the microcontroller. The microcontroller interprets this message, and writes a value encoding the amplitude of the voltage pulse to the digital-to-analog converter (DAC) through a serial peripheral interface (SPI) bus. The DAC outputs a corresponding voltage between 0 V and +30 V with 12-bit resolution. The DAC output enters an operational amplifier circuit that acts as a current buffer, and also offsets and increases the output voltage range to −30 V to +30 V. The output of this circuit is applied to the piezo previously selected by the relay. After the specified duration of the voltage pulse, the microcontroller again sets the piezo to the maximum negative voltage.

5 Graphical User Interface

Figure 5:
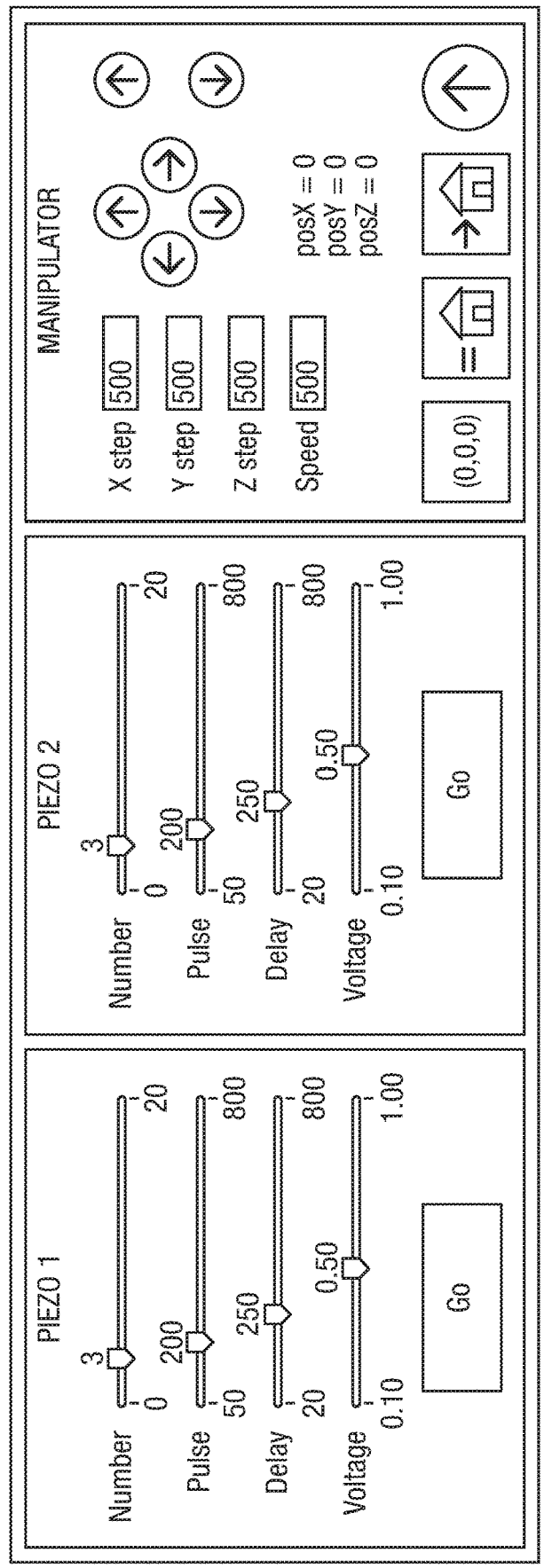
FIG. 5 shows a graphical user interface. The left and centre panels allow, for each of the two generators, variation of the duration (in μs) and amplitude (as a proportion of 60 V) of the voltage pulse, the triggering of droplet ejection, variation of the number of droplets to be ejected per trigger, and variation of the delay (in ms) between multiple droplets made per trigger. The right panel allows interactive control of the manipulator, and variation of the manipulator step size and speed.

A graphical user interface that enables real-time control of the droplet printer was written in the PRO-CESSING programming language (FIG. 5). The interface affords precise control of the amplitude and duration of the voltage pulse applied to each droplet generator. Droplet ejection can be triggered on demand, with a user-defined number of droplets and time delay between multiple droplets. These features allow the user to determine quickly, for each generator, the conditions required for the production of droplets of a specific size. The interface also gives the user direct control of the motorized micromanipulator, which was used to determine the correct spacing between droplets of a given size, as well as the relative displacement of the two nozzles. The latter was compensated for in the printing software to prevent a systematic displacement between the two types of droplets. The interface can be controlled through the computer keyboard or mouse.

6 Printing Algorithm

Droplet networks were printed according to an algorithm written in the PROCESSING programming language, and executed by the computer that controlled the two droplet generators and the motorized micromanipulator. Described first is the general pattern in which networks are printed, followed by a description of the printing algorithm.

6.1 Printing Pattern

Layers

The algorithm builds droplet networks by printing one horizontal layer at a time. The network to be printed is defined by a series of images, or maps, each of which represents one or more of the layers in the network (FIG. 2c). The number of layers represented by each map is specified by the user. Each pixel in a map may have one of three colours. Depending on its colour, each pixel represents a droplet from one the two droplet generators, or the absence of a droplet; these are respectively referred to here as A, B, and empty pixels.

Passes

Each layer is printed in two passes: in the first pass only the A droplets of the layer are printed, and in the second pass only the B droplets. Each pass is printed one row at a time, with each row parallel to the horizontal dimension x.

Goals

Figure 6A:
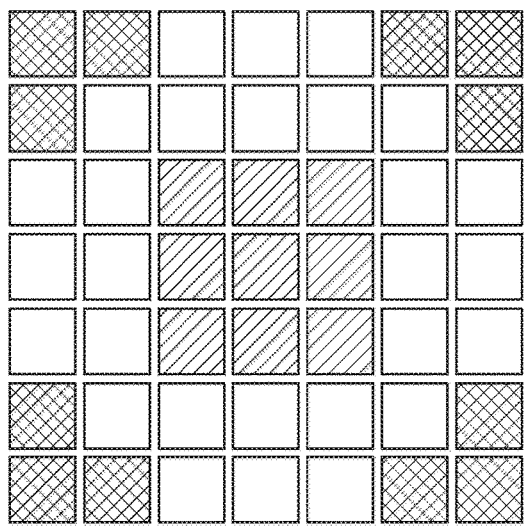
FIG. 6a provides an example of a map of 49 pixels, including A (light grey), B (dark grey, in the centre of the diagram) and empty (black)

The path that the printing nozzles are instructed to follow in a given pass is defined by an ordered set of coordinates, or goals, each of which represents a location at which a droplet is to be ejected. For each layer, a goal is set for each pixel in the corresponding map. The goal order begins at the minimum x and y, increases left to right along x in even-numbered rows, increases along y, and increases right to left in odd-numbered rows (FIG. 6).

Margin

Figure 6B:
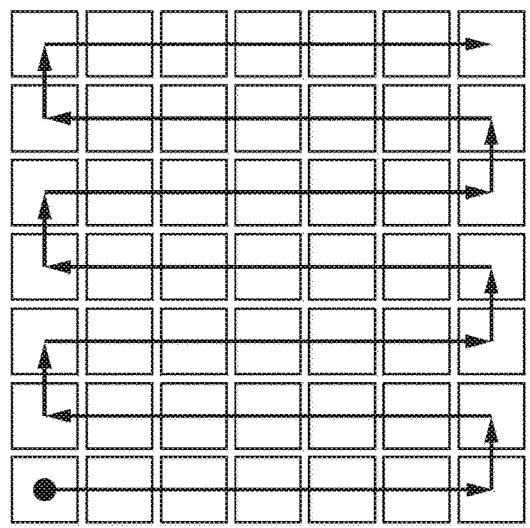
FIG. 6b shows the path taken by the printing nozzles across the map in each of the two passes, in the simplest variation of the printing algorithm.
Figure 7A:
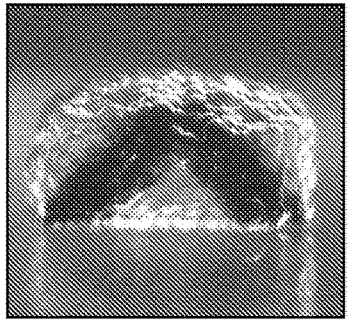
FIG. 7a shows a horizontal view of a network designed to be cuboidal, but resulting in a convex top face.
Figure 7B:
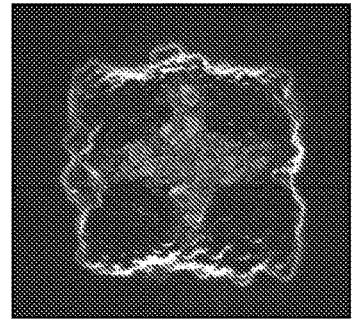
FIG. 7b shows a view from above of a network designed to be cuboidal, but resulting with inwardly sloped walls.

When the rectangular pattern in FIG. 6b was used to print networks designed to be cuboidal, the resulting networks often had sloped walls and a convex upper surface (FIGS. 7a,b). Observation of the printing process revealed that these deformations arose as a consequence of the finite time required for two droplets to form a bilayer after coming into contact (Supplementary Discussion). Droplets ejected at the outermost edges of the network therefore tended to roll down the outer walls for some distance before incorporating into the network. Although droplets in the first few layers sometimes rolled towards the centre of the network instead of away from it, this increased the probability that droplets subsequently printed at the same position would roll outwards.

Figure 7C:
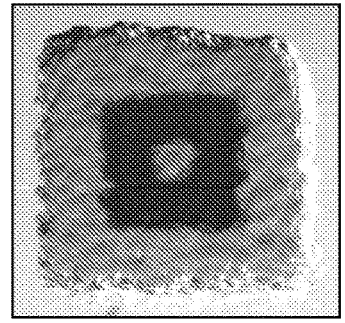
FIG. 7c shows a view from above of a network designed to be cuboidal and faithfully printed by the simple printing pattern.

The tendency of droplets to roll down the outer walls caused a depletion of droplets in the outermost parts of upper layers of the network, and an excess around the outermost parts of lower layers. In a few cases, however, networks printed in the same way did not exhibit the same distortion (FIG. 7c). In these cases, the motion of the nozzles through the oil dragged droplets towards the centre of the network before the droplets rolled down the sides.

It was found that the printing pattern could be modified slightly to considerably and reliably improve the accuracy with which networks were printed. The modification consisted of (i) the addition of an outer margin of one or two pixels to the network maps, and (ii) the modification of the printing algorithm so that in addition to the normal ejection of the droplets in each row, a droplet was ejected an additional n times at each of the marginal goals, where n~2 or 3 depending on the network printed. Although the first marginal droplets in each layer typically rolled down the outer walls of the network for a few layers, the following marginal droplets in that layer tended to incorporate into the network on top of these. In this way, the printing algorithm forms a barrier of marginal droplets that grows at the pace of the network, and prevents the internal droplets from rolling out of their intended boundary.

6.2 Algorithm: Initialization

The printing algorithm (FIG. 8) begins with an initialization phase that is executed once, followed by a direction phase that persists until printing has completed. In the initialization stage, the user first inputs the parameters shown in Table 1. Two of the parameters, the goal skipping threshold and the interface reset period, are explained in detail below. The program then loads into memory all the maps that define the network to be printed. A path for the printing nozzles, encoded as a series of goals according to the pattern detailed above, is established for the first pass of the first layer. Finally, the manipulator is instructed to move to the first goal. Once that goal is reached, the program sets a lower speed for the subsequent motion of the manipulator.

Goal Skipping Threshold

In a given pass, in general not all goals represent droplets of the colour corresponding to that pass; for example, in a layer that contains both A and B droplets, the A pass would include goals for B droplets. This can cause the manipulator to spend a significant time in travelling to goals at which no droplets are produced. This could be solved by simply skipping (that is, omitting from the printing path) all the goals that do not require droplets in the current pass. However, the motion of the nozzles through the oil can cause the displacement of droplets that have been recently produced (Supplementary Discussion). Therefore, skipping every goal that does not correspond to the current pass would cause some droplets in the network to be displaced differently to others, depending on their positions along the printing path.

The algorithm prevents this problem by allowing the manipulator to skip to the next goal that requires a droplet in the current pass only if no droplets have been ejected at any of the previous n goals, where n is the goal skipping threshold. The goal skipping threshold is chosen to allow recently-ejected droplets enough time to incorporate into the network, and so be unaffected by the motion of the printing nozzles.

Interface Reset Period

If the droplet generator chamber was too high above the level of oil solution in the well, the hydrostatic pressure from the aqueous solution caused the printing nozzle to spontaneously leak its contents into the oil. With the chamber ~1 cm above the oil and a typical nozzle with tip diameter ~80 µm, this leakage took place in two stages: an initial phase in which the aqueous volume gradually grew out of the nozzle to form an approximately hemispherical protrusion over several minutes, followed by a rapid phase in which the contents of the aqueous chamber emptied into the oil over a few seconds.

During the slower initial phase of leakage, the ejection of a droplet returned the aqueous-oil interface at the nozzle to its original planar geometry. The droplet generator that was used in given pass was therefore prevented from leaking its contents, because it ejected droplets at the relatively high rate of ~1 s$^{-1}$. However, because each pass took up to several minutes, the generator not used in a given pass could reach the rapid phase of leakage and empty its contents.

It was found that the application of certain voltage waveforms to a droplet generator would return the aqueous-oil interface at its nozzle to a planar geometry without causing the ejection of a droplet. The voltage waveform used to reset the interface typically consisted of three square pulses, each of duration 40 μs and amplitude ~12 V, with a 20 ms interval between them. In each pass, this waveform was applied every n goals to the droplet generator not used in that pass, where n is the interface reset period.

TABLE 1

Printing parameters.

| Parameter | Typical value |
|---|---|
| Spacing between droplets in x and y | 50 μm |
| x-offset for alternate rows | 25 μm |
| x- and y-offsets for alternate layers | 25 μm |
| Manipulator speed during printing | 200 μm s$^{-1}$ |
| Delay after ejecting each droplet | 200 ms |
| Delay after printing each row | 2 s |
| Goal skipping threshold | 4 |
| Interface reset period | 10 | x and y are the two horizontal dimensions, and rows of droplets are printed along x. In each layer, droplets in alternate rows can be printed with a displacement along x to promote the formation of a regular close-packed arrangement. Similarly, displacements in x and y can be set for droplets in alternate layers. The parameters goal skipping threshold and interface reset period are explained in the text.

6.3 Algorithm: Direction

In the direction stage, the computer synchronizes the motion of the oil bath with the ejection of droplets from the two generators according to the algorithm in FIG. 8. If the manipulator has reached its current goal, a droplet is ejected if the goal colour matches that in the current pass. If the goal was the last in the current pass, the pass number and layer number are updated. If the goal was the last in the entire network, the nozzles are raised out of the oil to prevent their leakage. Otherwise, the manipulator is instructed to travel to the next goal.

7 Electrical Simulation of Complex Droplet Networks 7.1 Statement of the Problem The inventors consider a set of N droplets, some of which are joined pairwise by bilayers in a given configuration. The bilayers may have different areas and contain any number of protein pores, and the bilayer areas and numbers of pores may vary with time. It was assumed that two of the N droplets, labelled a and b, are impaled by electrodes and poised at known voltages $u_a$ and $u_b$, respectively. The system is modelled as in FIG. 9, with each bilayer and any pores it contains represented by a capacitor and resistor in parallel. Given a droplet network of known connectivity, and bilayers of known conductance and capacitance, the inventors wish to calculate the current measured by the electrodes in droplets a and b.

7.2 Mathematical Formulation

The current flowing from droplet j, at electrical potential $V_j$, into droplet i, at electrical potential $V_i$, is given by $I_{ij} = I_{ij}^r + I_{ij}^c$, where $$I_{ij}^r = g_{ij}(V_i - V_j),$$

$$I_{ij}^c = c_{ij}(\dot{V}_i - \dot{V}_j), \quad (1)$$

and $g_{ij} = 1/r_{ij}$ is the conductance between droplets i and j, and $c_{ij}$ is the capacitance between droplets i and j. The net current into the ith droplet is given by the sum of the contributions from all droplets in the network:

$$I_i = \Sigma_{j \neq i} I_{ij}, \quad (2)$$

where the sum extends over the entire network and the inventors define $g_{ij}=0$ and $c_{ij}=0$ if droplets i and j are not joined by a bilayer. Substituting Eqs. (1) into Eq. (2) gives $$I_i = \Sigma_{j \neq i}(g_{ij}(V_i - V_j) + c_{ij}(\dot{V}_i - \dot{V}_j)),$$

which can be rearranged as $$I_i = V_i \sum_{j \neq i} g_{ij} - \sum_{j \neq i} g_{ij} V_j + \dot{V}_i \sum_{j \neq i} c_{ij} - \sum_{j \neq i} c_{ij} \dot{V}_j \quad (3)$$

At this point it is convenient to define the matrices G and C as follows:

$$G_{ij} = \begin{cases} -g_{ij}, & i \neq j, \\ \sum_{k \neq i} g_{ik}, & i = j. \end{cases}$$

$$C_{ij} = \begin{cases} -c_{ij}, & i \neq j, \\ \sum_{k \neq i} g_{ik}, & i = j. \end{cases}$$

With these matrices, Eq. (3) may be written succinctly as $$\vec{I} = G\vec{V} + C\dot{\vec{V}}, \quad (4)$$

where $\vec{I}$ and $\vec{V}$ are N-dimensional vectors that respectively represent the current owing into, and the voltage at, each droplet.

Finally, it was assumed that the droplets cannot act as sources or sinks of charge. The current flowing into each droplet is therefore zero, with the exception of the two droplets that are impaled by electrodes, which must source and sink the same current I:

$$|I_i| = \begin{cases} I, & i \in \{a, b\}, \\ 0, & \text{otherwise.} \end{cases} \quad (5)$$

7.3 Initial Conditions

It was assumed that the system begins in a steady state. Then $\dot{\vec{V}} = \vec{0}$, so from Eq. (4) the inventors have:

$$G\vec{V} = \vec{I}. \quad (6)$$

To solve for $\vec{V}$, it is recalled that the two terminal droplets are voltage-clamped. It is therefore possible to eliminate the two equations corresponding to droplets a and b, and use Eq. (5) to obtain:

$$\tilde{G}\vec{V} = \vec{0}, \quad (7)$$

Where $\tilde{G}$ represents the matrix G without the two rows corresponding to droplets a and b.

Eq. (7) represents N−2 equations in N variables. The two additional equations required to solve this system express the known voltages of the terminal droplets: $V_a = u_a$ and $V_b = u_b$. The inventors include these equations by constructing a further matrix $\tilde{G}'$, defined by replacing the rows in G that were removed to form $\tilde{G}$ with the row vectors $\vec{x}$ and $\vec{y}$, respectively, defined by $x_i = \delta_{ia}$ and $y_i = \delta_{ib}$, where $\delta_{ij}$ is the Kronecker delta. $\tilde{G}'$ is therefore defined as:

$$\tilde{G}'_{ij} = \begin{cases} \delta_{ai}\delta_{aj} + \delta_{bi}\delta_{bj}, & i \in \{a, b\} \\ -g_{ij}, & i \notin \{a, b\} \text{ and } i \neq j, \\ \sum_{k \neq i} g_{ik}, & i \notin \{a, b\} \text{ and } i = j. \end{cases}$$

Multiplying $\tilde{G}'$ by $\vec{V}$ then gives $$\tilde{G}'\vec{V} = \vec{v},$$

where $v_i = u_a \delta_{ia} + u_b \delta_{ib}$. This system of N equations in N variables is easily solved computationally, and yields the initial voltage of each droplet. The initial current is then found straightforwardly from Eq. (6).

7.4 Time Evolution

The time evolution of the system can be calculated in a manner similar to the initial conditions. The inventors again begin with Eq. (4), and remove the two rows of G and C that correspond to droplets a and b to create $\tilde{G}$ and $\tilde{C}$, where $\tilde{C}$ is defined analogously to $\tilde{G}$. Eq. (4) then becomes:

$$\tilde{G}\vec{V} + \tilde{C}\dot{\vec{V}} = \vec{0}.$$

The two rows removed from $\tilde{G}$ and $\tilde{C}$ were replaced with $\vec{x}$ and $\vec{y}$ to create $\tilde{G}'$ and $\tilde{C}'$, where:

$$\tilde{C}'_{ij} = \begin{cases} \delta_{ai}\delta_{aj} + \delta_{bi}\delta_{bj}, & i \in \{a, b\} \\ -c_{ij}, & i \notin \{a, b\} \text{ and } i \neq j, \\ \sum_{k \neq i} c_{ik}, & i \notin \{a, b\} \text{ and } i = j. \end{cases}$$

Recalling that the voltages $V_a = u_a$ and $V_b = u_b$ are constant, the following is obtained:

$$\tilde{G}'\vec{V} + \tilde{C}'\dot{\vec{V}} = \vec{v}. \quad (8)$$

The evolution of $\vec{V}$ through time was calculated as follows using MATLAB's ode45 ordinary differential equation solver:

1. At each time point t, G(t) is updated to reflect any changes in conductance that took place since the last time point to simulate pore insertions. It was assumed that there are no changes in bilayer sizes and that no new bilayers are formed, although these could be easily simulated by also updating C(t) at this step.

2. $\vec{V}(t)$ and the updated G(t) and C(t) are used in Eq. (8) to calculate $\dot{\vec{V}}(t)$.

3. $\vec{V}(t)$ and $\dot{\vec{V}}(t)$ are used to calculate the voltages at the next time point, $\vec{V}(t+\delta t)$. The interval $\delta t$ is determined by the ode45 solver.

Once $\vec{V}(t)$ has been calculated for the time period of interest, the current I(t) can be found straightforwardly from Eq. (4).

8 Water Permeability of Droplet Interface Bilayers

A pair of droplets labelled 1 and 2, joined by a bilayer of area A, were considered. Let the initial volumes of the droplets be $V_1$ and $V_2$, and their salt concentrations at time t be $C_1(t)$ and $C_2(t)$. The volume of water that flows per unit time from droplet 1 to droplet 2 across the bilayer can be expressed as (Dixit, S. S., et al., Langmuir 28, 7442-7451 (2012) and Cass, A. & Finkelstein, A. J. Gen. Physiol. 50, 1765{1784 (1967))

$$-\frac{dV_1}{dt} = iPA\overline{V}\phi(C_2(t) - C_1(t)), \quad (9)$$

where P is the permeability coefficient (with dimensions of length per unit time), $\overline{V}$ is the molar volume of water, $\phi$ is the osmotic coefficient, and i is the van't Hoff factor of the salt. Eq. (9) suggests a simple way to estimate the permeability P from experimental measurements:

$$P = [iA\overline{V}\phi(C_1(0) - C_2(0))]^{-1} \frac{dV_1}{dt}\bigg)_{t=0}, \quad (10)$$

where $C_1(0)$ and $C_2(0)$ are the initial values of $C_1$ and $C_2$, respectively. Because the volume of water is conserved, it may be equivalently written:

$$P = [iA\overline{V}\phi(C_2(0) - C_1(0))]^{-1} \frac{dV_2}{dt}\bigg)_{t=0}. \quad (11)$$

Figure 16A:
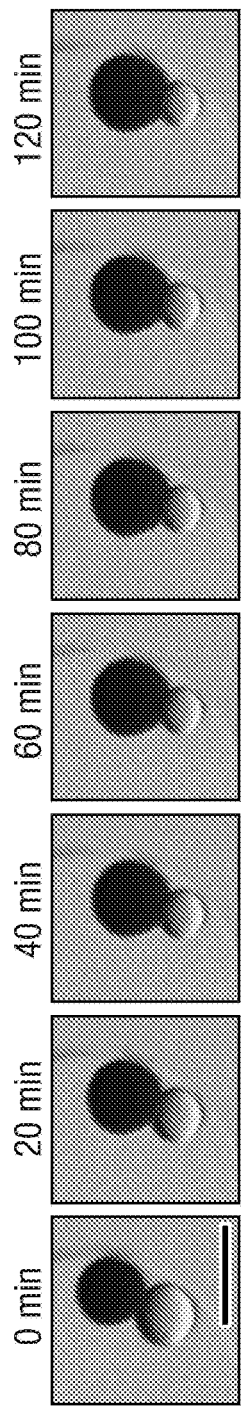
FIG. 16a provides photographs of a single pair of droplets with different salt concentrations, taken every 20 min after the droplets were joined by a bilayer. The dark grey droplet contained 25 mM Tris-HCl, 1 M KCl, 100 µM EDTA, pH 8.0. The lighter grey droplet contained the same solution, diluted to obtain a salt concentration of 250 mM KCl. The dark grey droplet additionally contained 1 mM xylene cyanol FF, and the lighter grey (smaller) droplet additionally contained 2.5 mM orange G. The scale bar represents 1 mm.
Figure 16B:
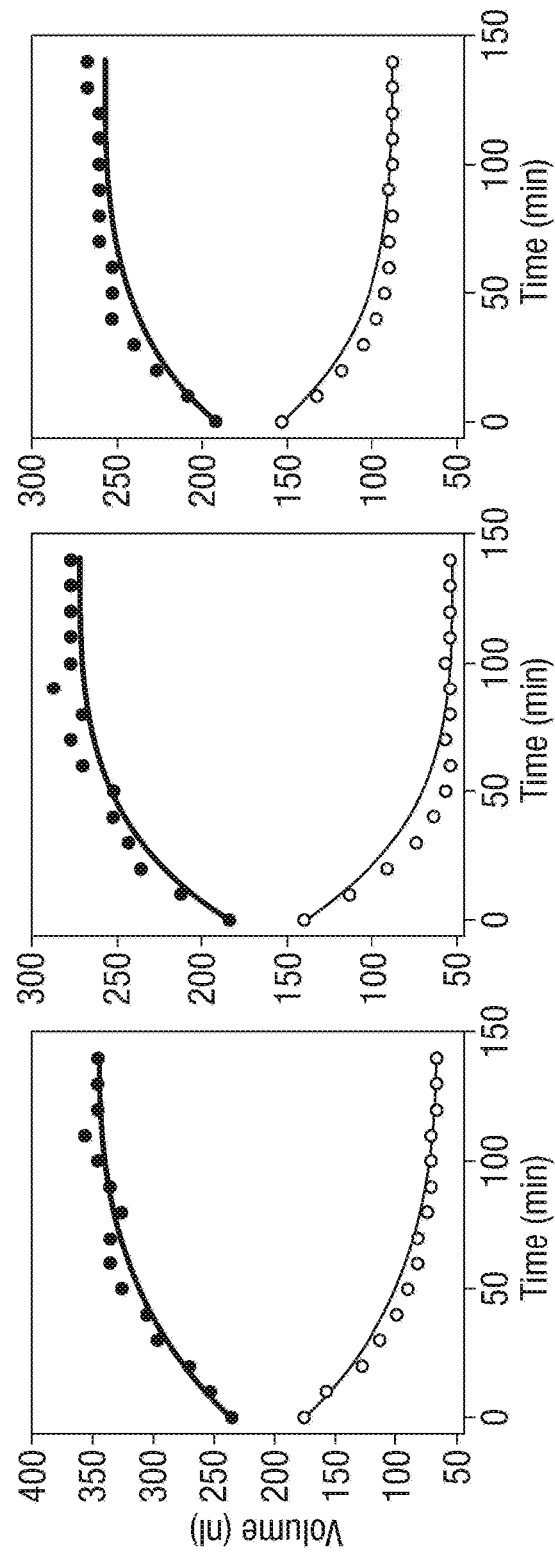
FIG. 16b demonstrates the volumes of three pairs of droplets as exemplified in FIG. 16a. The droplet and bilayer diameters were measured from photographs, and the droplet volumes calculated with the assumption of spherical cap geometries. The dark grey and light grey circles show the measured volumes of the dark grey and light grey droplets, respectively. These data were used to calculate the permeability coefficient P as described in the Examples, under Supplementary Methods. The dark grey and light grey lines show the droplet volumes calculated using Eq. (9) in the Examples, under Supplementary Methods, with the average measured value of $P=27$ µm s$^{-1}$. The calculated curves demonstrate that the data are well explained by the model with the average value of P.

Single droplets containing 1 M KCl were made to form bilayers pairwise with droplets containing 250 mM KCl, and three such pairs were photographed through a microscope at intervals of 2 min over a period of >2 h (FIG. 16). The droplet and bilayer diameters were measured using the ImageJ software package, and the volumes of the droplets calculated from these diameters by assuming that each droplet had the geometry of a spherical cap. The initial rates of change of $V_1$ and $V_2$ for each pair were calculated independently from the first two volume measurements. The permeability was then calculated according to Eq. (10) or Eq. (11), assuming $\overline{V}=18.0$ ml mol$^{-1}$, i=2 for KCl, and $\phi=0.90$ from the literature (Hamer, W. J. et al., J. Phys. Chem. Ref. Data 1, 1047-1100 (1972)).

9 Model of Folding Networks

9.1 Formulation of the Model

The qualitative behaviour of spontaneously folding networks can be reproduced by a simple model that consists of two coupled components: a mechanical part, which models the motion of droplets in a network, and an osmotic part, which models the transfer of water between droplets.

Mechanical Component

Droplets are treated as point masses with an associated radius. If a pair of droplets of radii $R_i$ and $R_j$ approach each other within a distance $R_i + R_j$, they become connected by a Hookean spring of natural length $L(R_i + R_j)$. The spring represents the bilayer formed between the two droplets, and the parameter L<1 approximates the deformation of the droplets caused by their adhesion.

Given that the characteristic timescale of folding in the experiments was on the order of minutes to hours, it was estimated that the Reynolds number during folding was on the order of $10^{-5}$. Droplets may therefore be expected to obey Stokes' law, and a drag force is imposed on each droplet that is proportional to its velocity. The net force on each droplet i is therefore given by $$\vec{F}_i = \sum_{j \in C_i} k(r_{ij} - L)\hat{r}_{ij} - \gamma\vec{v}_i, \quad (12)$$

where $C_i$ is defined as the set of droplets connected to the ith droplet, $\vec{r}_{ij}$ is the vector from droplet i to droplet j with magnitude $r_{ij}$, k is the spring constant, γ is a damping coefficient, and $v_i$ is the velocity of the ith droplet. The position of each droplet i through time, $\vec{r}_i(t)$, is then calculated using $$\vec{F}_i = m\frac{d^2\vec{r}_i}{dt^2}, \quad (13)$$

where m is the mass of the droplet. For reasons discussed below, the inventors assume that the mass, spring constant and damping coefficients are constant and identical for all droplets.

Osmotic Component

The osmotic component simulates the exchange of water between droplets of different osmolarities according to Fick's first law. The volume of water transferred per unit time from a droplet i with osmolarity $C_i$ to a droplet j with osmolarity $C_j$ was calculated as $$J_{ij} = A_{ij}(C_j - C_i), \quad (14)$$

where $A_{ij}$ is the area of the bilayer between the two droplets, and the parameter D represents a permeability coefficient that was assumed to be constant and identical for all bilayers.

9.2 Parameter Values

Table 2 lists the dimensionless values of the parameters used in the model. The values of D, m and k were chosen to make the timescale of water transfer slow compared to the timescale of mechanical relaxation, because the experimentally observed timescales for these processes were, respectively, tens of minutes and a few seconds. The value of γ was chosen to prevent oscillations of the springs while maintaining a relatively short mechanical relaxation time, because droplets are not experimentally observed to oscillate upon adhesion. $C_{low}$ and $C_{high}$ represent the lower and higher osmolarities of the droplets in the network. The ratio $C_{high}/C_{low}$ was chosen to approximate the experimental ratio of osmolarities. The remaining variables were chosen to reduce the computation time while maintaining numerical stability. Because the timescales of mechanical relaxation and water transfer were chosen so that folding takes place in a mechanical quasi-equilibrium, the simplifying assumption of identical and constant values of m and γ for all droplets, and of k for all bilayers, is not expected to have a significant effect on the simulations.

TABLE 2

Parameters used in folding model.

| Parameter | Symbol | Value |
| --- | --- | --- |
| Rate of water transfer | D | $2 \times 10^{-3}$ |
| Lower osmolarity | $C_{low}$ | 1 |
| Higher osmolarity | $C_{high}$ | 10 |
| Initial droplet volume | $V_0$ | 10 |
| Droplet mass | m | 0.2 |
| Spring constant | k | $10^3$ |
| Time step | Δt | $10^{-2}$ |
| Damping | γ | 1.1 |

The parameters D, m and k were chosen to make water transfer take place on a much longer timescale than mechanical equilibration of the network. The value of γ was chosen to prevent oscillations of the springs. $C_{high}/C_{low}$ was chosen to reflect the experimental ratio of osmolarities between the two types of droplets. $C_{high} - C_{low}$, Δt and $V_0$ were chosen to reduce the computation time while maintaining numerical stability.

9.3 Solving the Equations

A computer program was written to simulate the behaviour of the system as follows. The program reads a series of images that define the network to be simulated, similarly to the printing program. The droplets are initially positioned according to the images in a hexagonal close-packed arrangement, which approximates the observed packing of droplets in printed networks. The droplets are then allowed to equilibrate mechanically without exchanging water, to ensure that any motion subsequently simulated is not due to mechanical equilibration of the droplets from their initial arrangement. Once this equilibration is complete, the osmotic component of the model is activated. At each time point t, the program performs the following calculations:

1. Any two droplets i and j that have come within a distance $R_i + R_j$ are connected by a spring of natural length $L(R_i + R_j)$.

2. If the osmotic component is active, the volume of water transferred between each pair of droplets joined by a bilayer is calculated according to Eq. (14), and the size of each droplet is updated accordingly.

3. The position of each droplet at time t+Δt is calculated according to Eqs. (12) and (13) using a fourth-order Runge-Kutta scheme.

4. The position of each droplet is updated according to the results of the calculations in step 3.

9.4 Visualization

At each time point during the simulation, the program wrote the position of every droplet to a text file, formatted such that it could be read by the Visual Molecular Dynamics software package (Humphrey, W., et al., J. Molec. Graphics 14, 33-38 (1996)) to visualize the time evolution of the network. In addition to showing the position and size of each droplet, the visualization colour-coded each droplet according to its osmolarity. The colour scale interpolates from blue to white to red, where blue and red respectively correspond to the lowest and highest osmolarities at the beginning of the simulation, and white corresponds to the average of the two.

Supplementary Discussion

1 Droplet Production

A number of factors other than the amplitude and duration of the voltage pulse were found to significantly affect droplet production by the droplet generators.

Fluid Levels

Droplet ejection depended strongly on the height difference h between the level of the aqueous phase in the chamber of the droplet generator and the level of oil solution in the well (FIG. 1), which produced a net force on the aqueous-oil interface in the nozzle. In general, a greater height h yielded larger droplets. Evaporation of the aqueous solution from the chamber gradually changed the aqueous level, so that the size of ejected droplets remained consistent for only ~6 h. Evaporation might be prevented by adding a thin layer of oil on top of the aqueous phase in the chamber.

Aqueous Volume

Droplet ejection also depended on the volume of aqueous solution V in the droplet generator chamber, independently of its height above the oil level (FIG. 1). In general, the size of ejected droplets was more readily controlled when the aqueous chamber was completely full than when it was filled incompletely. This is likely because upon the application of a voltage pulse to the piezoelectric transducer, a less-filled chamber couples less of the vibration from the transducer to the fluid in the nozzle, which limits the size of the ejected droplets.

Lipid Concentration

The amplitude of the voltage pulse required to eject droplets of a given size was lower for higher concentrations of lipid in the oil. This is to be expected: the adsorption of lipids at the aqueous-oil interface in the nozzle decreases the tension of that interface, thereby lowering the energy required to deform the interface to the extent required for droplet formation.

Nozzle Geometry

Droplets could not be produced reliably in the available range of voltages if the nozzle length L was too great, its internal diameter D was too small, or its tip diameter d was too great or too small (FIG. 1). The dimensions given in FIG. 3 allowed reliable droplet production within the available voltage range. Because the nozzles were produced manually from glass capillaries, under otherwise almost identical conditions the two generators generally produced droplets of different sizes. However, the two generators could be made to eject identical droplets by using different voltage pulses for each.

2 Printing Networks

The dynamic viscosity of the oil mixture used was ~10 times greater than that of water. This posed several challenges for the printing of droplet networks that do not arise in most other two- and three-dimensional printing technologies, which operate in air or aqueous solution:

1. Following the application of a voltage pulse of the piezoelectric transducer, the pulse of pressure produced at the nozzle creates a short-lived protrusion of the aqueous phase into the oil phase ~50-150 μm long, which breaks up within tens of ms to create a single droplet. When the nozzle was placed ≤150 μm from an obstacle, the obstacle deformed the aqueous protrusion, causing the ejected droplet to be displaced. Placing the nozzle ≤100 μm from an obstacle precluded droplet formation entirely. Each droplet was therefore ejected ≥200 μm above its final position. However, droplets then required ~1-5 s to sink from their point of ejection into their intended position in the network.

2. Droplets did not adhere and form a bilayer immediately upon coming into contact with the network. This is likely to be due to the finite time required for the oil layer between two droplets to thin under the weight of the falling droplet. Droplets typically formed bilayers with the network ~1-3 s after first coming into contact with the network.

3. Droplets not yet incorporated into the network were displaced by viscous shear produced by the motion of the nozzles through the oil.

4. Droplets not yet incorporated into the network were displaced by subsequent nearby ejections.

In order to print droplets at accurate locations at a rate of $\sim 1$ $s^{-1}$, the inventors addressed these problems in a series of optimizations.

Nozzle Geometry

The displacement of droplets caused by motion of the nozzle was minimized by using nozzles with a relatively small outer diameter of ~100 μm. The nozzles were formed from tapered glass capillaries as described in the Supplementary Methods. When using capillaries that had been shaped to have a similar inner diameter but an outer diameter of 1.5 mm, the motion of the nozzle displaced the droplets by a significantly greater distance.

Row Delay

The use of a delay after printing each row of droplets, instead of after ejecting each droplet, allowed a significant reduction in printing time without a significant cost to print quality. Although the droplets in each row were then displaced by motion of the nozzle and subsequent ejections in that row, every droplet suffered approximately the same displacement, so that droplets were placed in the correct relative positions within their row. Depending on the orientation of the nozzles, the alternating direction of the printing path for alternating rows could result in a misalignment of alternate rows. However, the misalignment was easily corrected with a programmed offset for alternate rows (Supplementary Methods).

Sinking Rate

To reduce the row delay necessary to prevent droplet displacement, the inventors increased the rate at which droplets sank through the oil in two ways. First, the inventors used a salt concentration of 1 M KCl in the aqueous phase, which increased the density of the droplets relative to the oil solution. Second, they used droplets ≥30 μm in diameter, because larger droplets suffer proportionately less viscous drag for their weight.

Lipid Concentration

For a given concentration of lipid in the oil, smaller droplets require less time to acquire a lipid monolayer (Kankare, J. et al., Langmuir 15, 5591-5599 (1999)). This is because the adsorption of lipid onto the droplet surface creates a lipid-depleted region around the droplet, and for smaller droplets this depleted volume is more accessible to replenishment by transfer from the lipid bath. The droplet diameter is therefore a compromise between a high sinking rate (which occurs with larger droplets) and a short incubation time (which requires smaller droplets). In the experiments it was found that droplet diameters in the range ~30-60 μm were a good compromise.

3 Printing in Bulk Aqueous Solution

Printing Process

In contrast to the networks printed in bulk oil, the networks in bulk aqueous solution were printed by controlling the droplet generators and manipulator during printing using a custom-written graphical user interface (Supplementary Methods). Because the recipient oil drop used to print in bulk aqueous solution had a curved lower surface, droplets ejected inside the oil drop rolled down the surface to minimize their gravitational energy. Therefore the accurate printing of defined networks in bulk aqueous solution requires knowledge of the geometry of the surface of the oil drop. Further, the droplet network design and printing path should be compatible with that geometry. For instance, for oil drops with the geometries used in these Examples, the aqueous droplets could be prevented from rolling away from their intended positions by printing each layer in an outwardly growing spiral pattern centred about the minimum point.

Geometry of Wire Frames and Networks

The geometry of the oil drop is partially determined by the wire frame used to suspend the drop in bulk aqueous solution. However, the geometry of the drop changes as aqueous droplets are ejected into it, while the volume of oil remains constant. A network printed in an oil drop may therefore have a different geometry to the initial geometry of the oil drop, and may have a volume greater than that of the oil drop.

Further, unlike the oil drop, the geometry of a printed network need not have the minimal bounding surface area, as is evident from the third micrograph in FIG. 11d. This is possible firstly because the rearrangement of the network into a configuration with the minimal bounding area would involve the separation of bilayers into monolayers, which is energetically unfavourable (Villar, G., et al., Nature Nanotech. 6, 803-808 (2011)) and therefore presents a kinetic barrier. Secondly, the interfacial tension of the bilayer between two encapsulated droplets is identical or approximately equal to that of the bilayer between an encapsulated droplet and the bulk aqueous solution ((Villar, G., et al., Nature Nanotech. 6, 803-808 (2011)), so the thermodynamic stability that would be gained by minimizing the external area of the network is likely to be negligible. The geometry of networks printed in bulk aqueous solution is therefore not fully determined by the frame. It should also be possible to print networks using frames in a variety of geometries other than simple circular loops, which further widens the possible geometries of networks printed in aqueous solution.

Upper Limits on Oil Volume

The volume of oil that could be stably suspended on a given loop depended on the diameter of the loop. When a loop was loaded with an oil volume ≥50% of the volume of a sphere bounded by the loop, the oil drop deformed over a few minutes until it broke up to form a drop that floated upwards in the aqueous phase, while the residual oil remained attached to the loop. The slow change in geometry of the oil drop was presumably due to a gradual decrease in surface tension caused by the adsorption of lipid at its surface.

The maximum suspended volume of oil also depended on the geometry of the nozzles. When the two nozzles were inserted into the oil drop approximately parallel to each other and separated by ≤200 μm, most of the oil rose spontaneously in the space between the nozzles. Larger frames may therefore be best designed as fine meshes to prevent the oil drop from breakup instability and from rising between the nozzles by capillary action.

4 Electrical Recording

It is not possible to determine directly from electrical recordings, such as that in FIG. 12c, whether the measured current steps corresponded to insertions of αHL into bilayers (i) between droplets in the network, or (ii) between the network and the large drops impaled by electrodes. However, the latter is more likely for two reasons, as follows.

Rate of αHL Insertion

The rate of αHL insertions into droplet interface bilayers decreased with time. In droplets that contained αHL in the concentration used in the electrical recording experiments, the rate of pore insertion decreased from ~0.5 $s^{-1}$ a few minutes after the droplets were formed to a negligible rate after a few hours. The attrition of the rate of pore insertion is likely to have two contributions. First, droplets were made by diluting a concentrated stock solution of αHL heptamers solubilized with sodium dodecyl sulphate (SDS). The dilution is likely to encourage the dissociation of SDS from the protein, which would destabilize the heptamers. Further, whereas the stock and diluted solutions of αHL were refrigerated at −80° C. and 0° C., respectively, the experimental system was at room temperature, which would also increase the rate of heptamer degradation.

The droplets on the conductive pathway were formed from a freshly diluted solution that was at room temperature during printing for ~2 h before electrical recording, whereas the large drops impaled on electrodes were formed only ~15 min before electrical recording. Any pores that inserted in bilayers during electrical recording are therefore more likely to have been in the large drops than in the droplets in the pathway.

Consistency of Measured Currents with Electrical Model

The likely configurations of αHL pores in the network was deduced by comparing the experimentally measured currents with simulations of the electrical behaviour of droplet networks (FIG. 14) (Supplementary Methods). Only part of the network in FIG. 12 was simulated to decrease the computation time; the simulation results are not expected to change significantly with the inclusion of the rest of the network. The measured currents such as in FIG. 12c were consistent with the simulations only if three conditions were met:

1. Most of the bilayers in the conductive pathway contained at least several αHL pores, so that the pathway had negligible resistance compared to that of a single pore. This is reasonable, given the relatively high concentration of αHL used and the relatively long time available for pores to insert into bilayers in the pathway.

2. Many of the bilayers between the pathway and one of the electrode-impaled drops (drop a in FIG. 14a) contained at least one αHL pore, while no pores were present in any of the bilayers that joined the pathway to the other electrode-impaled drop (drop b in FIG. 14a). This is plausible, given that one of the large drops was placed onto the network approximately tens of seconds before the other.

3. The bilayers formed by the second electrode-impaled drop to be connected to the pathway (drop b in FIG. 14a) initially contained no αHL pores, and the first current step corresponded to the insertion of a pore in any bilayer between that drop and the pathway. Each subsequent step was due to the insertion of additional pores in these bilayers. This condition is reasonable, because the experimental electrical recording began immediately after the second electrode-impaled drop was joined to the pathway.

Figure 14B:
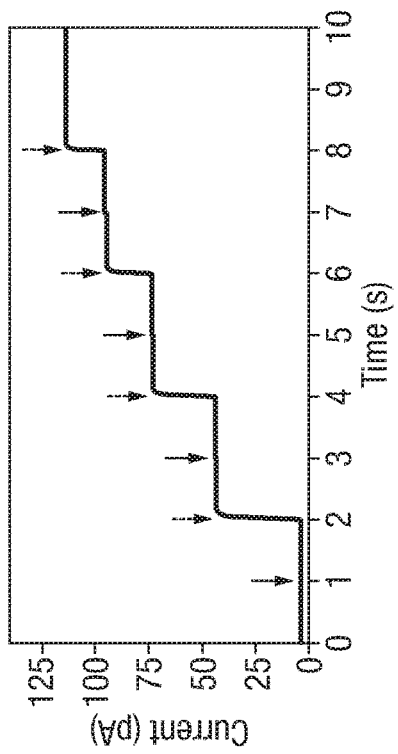
FIG. 14b shows a simulated current between the electrodes in the system depicted in FIG. 14a. The simulation used the following parameter values, as an approximation of the conditions of the experiments described in the Examples: an applied potential of 50 mV, bilayer diameters of 45 μm, a bilayer specific capacitance of 650 nF cm$^{-2}$ (Holden, M. A., et al., J. Am. Chem. Soc. 129, 8650-8655 (2007)), a bilayer conductance of 1 pS, and a pore conductance of 1 nS (Holden, M. A., et al., J. Am. Chem. Soc. 129, 8650-8655 (2007)). Five αHL pores are assumed to be initially present in each bilayer within the network. Each of the bilayers between the network and drop a is assumed to initially contain one pore, while those between the network and drop b are assumed to contain no pores. The insertion of a single αHL pore into a bilayer between the network and drop a is simulated to occur at 1 s, 3 s, 5 s and 7 s (dark grey arrows), and into a bilayer between the network and drop b at 2 s, 4 s, 6 s and 8 s (light grey arrows). Each pore inserts into a different bilayer. Note that to decrease the computation time, the time interval of the simulation was made shorter than that in FIG. 12c.
Figure 14D:
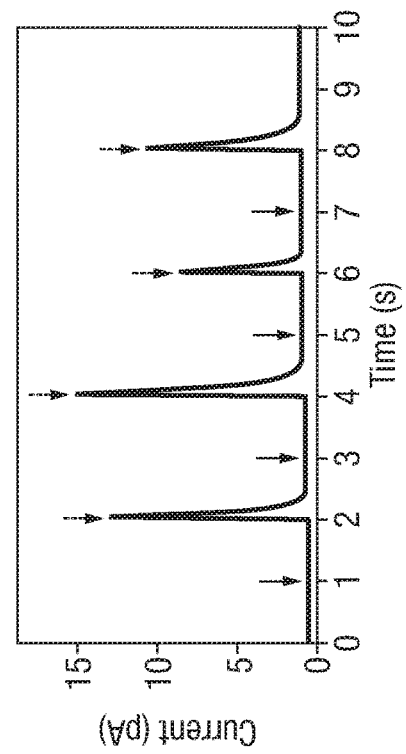
FIG. 14d shows a simulated current between the electrodes in FIG. 14c. The simulation was performed with the same conditions as described in FIG. 14b, except that no pores were initially present in any of the bilayers formed by the rightmost column of droplets in the network. The arrows signify pore insertions as described in FIG. 14b.
Figure 14A:
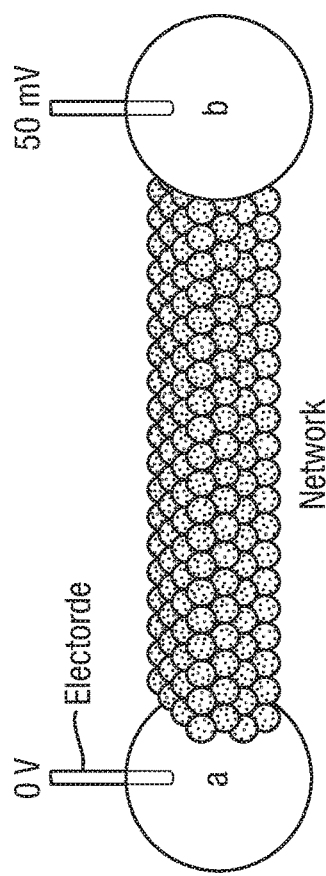
FIG. 14a provides a schematic of the system simulated as a model of the electrical recording conditions in FIG. 12b. The network consists of 4 rows, 20 columns and 4 layers of droplets in a face-centred cubic arrangement, and represents only the conductive pathway part of the network in FIG. 12. Two large drops are positioned at either end of the network, and form bilayers with the network droplets at the end of each row.
Figure 14C:
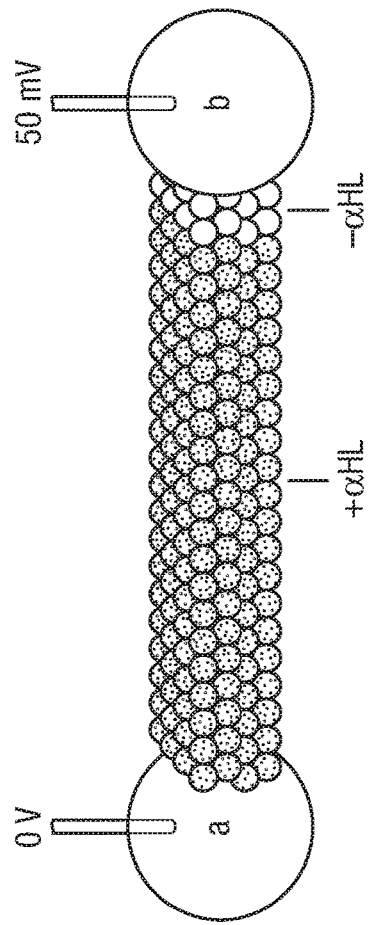
FIG. 14c shows a schematic of the system simulated as a model of the electrical recording conditions in FIG. 12d. The network is identical to that in FIG. 14a, except for the addition of two columns of droplets that do not contain αHL.

Under these conditions, the simulated current steps closely matched the measured currents in both the step amplitudes and relaxation timescale (FIG. 14b).

Similarly, the transient current peaks measured with one drop on the pathway and one off the pathway (FIG. 12d) were consistent with the simulations if, in addition to the above conditions, a thin layer of droplets was added that did not allow the flow of current between one electrode-impaled drop and the rest of the network. These insulating droplets represent the droplets in the network in FIG. 12d that did not contain αHL. The large drop chosen to be adjacent to this insulating layer was drop b in FIG. 14c, which represents the drop that was removed from the network and replaced away from the pathway in FIG. 12d. Under these conditions, both the amplitudes and relaxation time-dependence of the current peaks in the simulation (FIG. 14d) were consistent with the transient currents measured experimentally (FIG. 12e).

5 Self-Folding Networks

This section details the conditions that were found to allow success folding of droplet networks.

Printing Substrate

Static networks in bulk oil were printed on glass, which was adhesive to the aqueous droplets, to prevent any unwanted displacement of the network during printing. Conversely, for droplet networks to deform freely it was found necessary to print on a surface of poly(methyl methacrylate), which was not adhesive to droplets. When printing networks on this surface, it was necessary to ensure that the printing surface was close to horizontal, to prevent the growing network from drifting along the surface during printing. The nozzles were also positioned ~150 μm higher from the printing substrate to prevent the ejection of droplets from displacing the network.

Timescales of Printing and Folding

If the network folds significantly before printing has completed, the later droplets may incorporate into the network at incorrect positions. The extent to which the network folds during printing can be minimized by decreasing the printing time, and increasing the folding timescale. As discussed in an earlier section, the printing time can be shortened by including a delay after each row rather than after each droplet, and by using larger droplets.

The folding timescale can be increased in two ways:

1. The rate of water transfer between two droplets is proportional to the difference in their salt concentrations; the ratio of salt concentrations partially determines the total volume of water transferred, and therefore the equilibrium geometry of the folded network. The inventors therefore slowed the folding process by reducing the initial difference in salt concentrations between the two droplet types, while maintaining a high ratio of initial salt concentrations.

2. The folding timescale was increased further by printing with larger droplets. Consider a pair of droplets joined by a bilayer, both with initial volume V but each with a different initial osmolarity. The initial rate of water transfer is proportional to the bilayer area, A. Because $A \propto V^{2/3}$, water is transported more rapidly between larger droplets. However, the rate of water transfer as a proportion of the droplet volume is $\propto A/V \propto V^{-1/3}$. Therefore relative to their initial volume, larger droplets change in volume more slowly, and by extension a network composed of larger droplets will fold more slowly.

Buckling

As the droplets of higher osmolarity swell and those of lower osmolarity shrink in a spontaneously folding network, a length mismatch can develop between connected regions of the network with different osmolarities. Networks that are thin in one dimension can resolve this mismatch without a significant energetic cost by buckling into that dimension. It was found that networks designed to fold in the horizontal plane were less prone to buckle out of that plane if printed with additional vertical layers. This is presumably because bending the thick network out of the plane would involve the unfavourable exposure of more monolayer area or total surface area.

Fracture

Figure 17A:
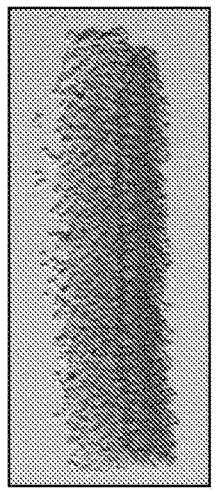
FIG. 17a shows a network composed of two strips of droplets similar to that in FIG. 15c, except that the strip of droplets of lower osmolarity in this network was thinner horizontally.
Figure 17B:
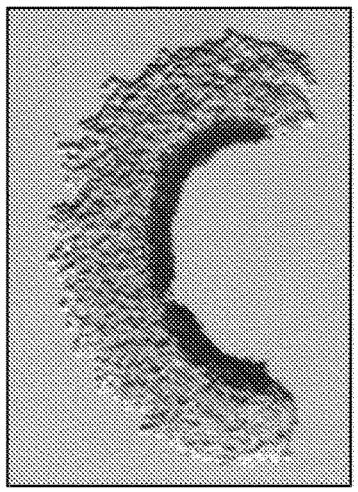
In FIG. 17b the same network as in FIG. 17a is depicted, after the completion of folding. The point of fracture in the region of dark grey droplets is evident.
Figure 17C:
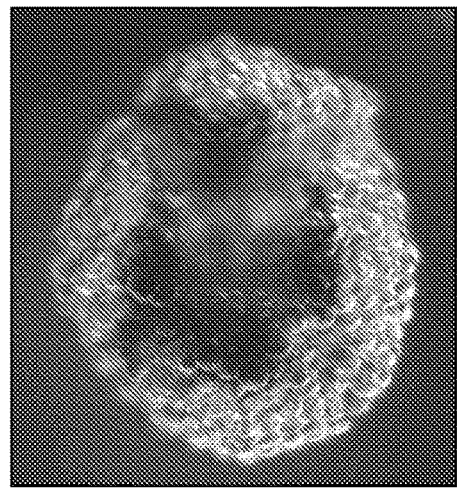
FIG. 17c shows an originally cross-shaped network similar to the petal-shaped network in FIGS. 15d and 15e. The layer of lower osmolarity fractured near the base of the upper arm, as evidenced by the absence of dark grey droplets in that region. Note that the fractured arm folded to a lesser extent than the others.

In networks that are thick along the axis about which folding takes place (for example, the axis perpendicular to the page in FIG. 15c), the length mismatch between connected regions discussed above can produce stresses that detach neighbouring shrinking droplets from each other (FIG. 17). The deformation of a spontaneously folding network requires that the swelling and shrinking portions of the network be connected both to each other and within themselves, so the fracture of the network at some point can preclude further deformation around that point. It was found that this type of fracture did not occur if the shrinking region of the network was made thicker along the axis perpendicular to the interface between the swelling and shrinking regions (for example, the vertical axis in FIG. 15d, and the horizontal axis on the page in FIGS. 17a,b). This extra thickness presumably distributes the stresses induced by folding among a greater number of bilayers, so that the forces on each connected pair of shrinking droplets are no longer sufficient to separate the droplets.

CONCLUSIONS

The inventors have shown that the apparatus of the invention can be used to produce a droplet assembly. The results and methods discussed above show how the apparatus can be adapted to produce the required droplet assembly. Further, the results show that the process of the invention produces droplet assemblies with precision and control. The results demonstrate that millimetre-sized networks can be printed. Larger networks may also be produced. Further, the assemblies can functionalised. The inventors have also demonstrates that networks can be printed to self-fold in predictable ways.

The use of membrane proteins such as aquaporins or ion channels could be used in droplet assemblies to afford greater control over the flow of water within droplet networks. Further, the osmotic shape change may be made reversible, for instance by using osmolytes that are responsive to heating or illumination. Such droplet networks could be developed as a hydraulic mimic of muscle tissue, and may allow the construction of droplet networks capable of locomotion.

Because neighbouring cells in a living tissue are separated by two membranes, they must communicate through specialized membrane proteins such as gap junctions (Nakagawa, S., et al., Curr. Opin. Struc. Biol. 20, 423-430 (2010)) to cooperate, and so produce the emergent properties that distinguish a tissue from a collection of independently functioning cells. The system of the present invention, in which a single layer (such as a single lipid bilayer) separates adjacent aqueous compartments, allows these collective properties to emerge in a simpler environment. The automated printing process presented here will allow the construction of networks that use other membrane proteins and osmolytes to reproduce more sophisticated behaviours. Such droplet networks might function autonomously within living organisms or be interfaced with tissues, for example as platforms for drug delivery, or to augment or replace failing tissues or organs.

The invention claimed is:

1. A process for producing a droplet assembly using an apparatus for producing the droplet assembly, which droplet assembly comprises: a plurality of droplets, wherein each of said droplets comprises: (i) a droplet medium, and (ii) an outer layer of amphipathic molecules around the surface of the droplet medium, wherein the droplet medium is an aqueous medium or a hydrophobic medium, and wherein each of said droplets contacts another of said droplets to form a bilayer of said amphipathic molecules as an interface between the contacting droplets wherein the droplet assembly comprises at least n of said droplets, and at least n−1 of said interfaces between contacting droplets, wherein n is equal to or greater than 4;

which apparatus comprises: at least one droplet generator; a container which is moveable relative to the at least one droplet generator; and a control unit, which control unit is adapted to control the dispensing of droplets from the at least one droplet generator and the movement of the container relative to the at least one droplet generator;

wherein said container of the apparatus contains a bulk medium, wherein:

when the droplet medium is an aqueous medium the bulk medium is a hydrophobic medium, and when the droplet medium is a hydrophobic medium the bulk medium is an aqueous medium;

which process comprises:

(a) at least n dispensing steps, wherein each dispensing step comprises dispensing a droplet of the droplet medium from a said droplet generator into the bulk medium, in the presence of amphipathic molecules, and thereby forming in the bulk medium a droplet which comprises (i) said droplet medium and (ii) an outer layer of amphipathic molecules around the surface of the droplet medium; and (b) between the dispensing steps, or between and during the dispensing steps, moving the container relative to the at least one droplet generator, to control the relative positioning of the droplets in the bulk medium and to position each droplet adjacent to at least one other droplet, so that each of said droplets contacts another of said droplets to form a bilayer of said amphipathic molecules as an interface between contacting droplets, wherein the control unit coordinates the dispensing steps, and the movement of the container relative to the at least one droplet generator, to produce the droplet assembly, and the droplets are dispensed at a rate of at least $0.5\ s^{-1}$.

2. A process according to claim 1 wherein the droplet medium is an aqueous medium and the bulk medium is a hydrophobic medium.

3. A process according to claim 2 wherein n is equal to or greater than 500 and the process comprises:
(a) a first dispensing step, comprising dispensing a droplet of the aqueous medium from a said droplet generator into the hydrophobic medium, in the presence of the amphipathic molecules, and thereby forming in the hydrophobic medium a first droplet which comprises (i) said aqueous medium and (ii) an outer layer of the amphipathic molecules around the surface of the aqueous medium;
(b) moving the container relative to the at least one droplet generator, to control the positioning of a second droplet in the hydrophobic medium relative to the first droplet in the hydrophobic medium so that the second droplet is positioned adjacent to the first droplet, so that the first and second droplets contact one another to form a bilayer of said amphipathic molecules as an interface between the contacting droplets;
(c) a second dispensing step, comprising dispensing a droplet of the aqueous medium from a said droplet generator into the hydrophobic medium, in the presence of the amphipathic molecules, and thereby forming in the hydrophobic medium the second droplet, which second droplet comprises (i) said aqueous medium and (ii) an outer layer of the amphipathic molecules around the surface of the aqueous medium;
(d) moving the container relative to the at least one droplet generator, to control the positioning of a further droplet in the hydrophobic medium relative to the other droplets in the hydrophobic medium, so that the further droplet is positioned adjacent to at least one other droplet in the hydrophobic medium, so that the further droplet contacts at least one other droplet in the hydrophobic medium to form a bilayer of said amphipathic molecules as an interface between the contacting droplets; and
(e) a further dispensing step, comprising dispensing a droplet of the aqueous medium from a said droplet generator into the hydrophobic medium, in the presence of the amphipathic molecules, and thereby forming in the hydrophobic medium the further droplet, which further droplet comprises (i) said aqueous medium and (ii) an outer layer of the amphipathic molecules around the surface of the aqueous medium, wherein the process comprises at least 500 of said further dispensing steps (e).

4. A process according to claim 2 wherein the plurality of dispensing steps comprises dispensing steps which together produce a row or layer of said droplets in the hydrophobic medium, wherein each droplet in the row or layer contacts another droplet in the row or layer to form a bilayer of said amphipathic molecules as an interface between contacting droplets.

5. A process according to claim 1 wherein the droplet medium is an aqueous medium and the bulk medium is a hydrophobic medium and wherein the plurality of dispensing steps comprises:
a first set of dispensing steps, which together produce a first region of said droplets in the hydrophobic medium, wherein each droplet in the first region contacts at least one other droplet in the first region to form a bilayer of said amphipathic molecules as an interface between contacting droplets; and
a second set of dispensing steps, which together produce a second region of said droplets in the hydrophobic medium, wherein each droplet in the second region contacts at least one other droplet in the second region to form a bilayer of said amphipathic molecules as an interface between contacting droplets.

6. A process according to claim 5 wherein the aqueous medium of the droplets dispensed into the hydrophobic medium in said first set of dispensing steps further comprises a membrane protein, and wherein the aqueous medium of the droplets dispensed into the hydrophobic medium in said second set of dispensing steps does not comprise said membrane protein, or wherein the aqueous medium of the droplets dispensed into the hydrophobic medium in said first set of dispensing steps comprises a higher concentration of a membrane protein than the aqueous medium of the droplets dispensed into the hydrophobic medium in said second set of dispensing steps.

7. A process according to claim 6 wherein the bilayers of amphipathic molecules formed between the contacting droplets in the first region comprise said membrane protein, and the bilayers of amphipathic molecules formed between the contacting droplets in the second region do not comprise said membrane protein or comprise a lower concentration of said membrane protein than the bilayers of amphipathic molecules formed between the contacting droplets in the first region.

8. A process according to claim 6 wherein the membrane protein is a pump, channel or a pore, a receptor protein, a transporter protein, or a protein which effects cell recognition or a cell-to-cell interaction.

9. A process according to claim 5 wherein:
the aqueous medium of the droplets dispensed into the hydrophobic medium in said first set of dispensing steps has a first osmolarity, and the aqueous medium of the droplets dispensed into the hydrophobic medium in said second set of dispensing steps has a second osmolarity, wherein the first osmolarity is greater than the second osmolarity; and
droplets in the second region are disposed adjacent to droplets in the first region, so that droplets in the first region contact droplets in the second region to form bilayers of said amphipathic molecules as interfaces between the contacting droplets.

10. A process according to claim 9 which further comprises allowing water to transfer from the second region to the first region, to cause deformation of the droplet assembly.

11. A process according to claim 10 wherein the transfer causes the first and second regions to curve or fold.

12. A process for producing a droplet assembly according to claim 1 wherein the droplet medium is an aqueous medium and the bulk medium is a hydrophobic medium and wherein the apparatus comprises a first droplet generator and a second droplet generator, and the plurality of dispensing steps comprises:
- at least one dispensing step which comprises dispensing a droplet of a first aqueous medium from the first droplet generator into the hydrophobic medium, in the presence of amphipathic molecules, and thereby forming in the hydrophobic medium a droplet which comprises (i) said first aqueous medium and (ii) an outer layer of amphipathic molecules around the surface of the aqueous medium; and
- at least one dispensing step which comprises dispensing a droplet of a second aqueous medium from the second droplet generator into the hydrophobic medium, in the presence of amphipathic molecules, and thereby forming in the hydrophobic medium a droplet which comprises (i) said second aqueous medium and (ii) an outer layer of amphipathic molecules around the surface of the aqueous medium,
wherein the first aqueous medium and the second aqueous medium are the same or different.

13. A process according to claim 12 wherein the first and second aqueous media have different osmolarities.

14. A process for producing a droplet assembly according to claim 1 wherein the droplet medium is an aqueous medium and the bulk medium is a hydrophobic medium, and wherein said bulk medium which is a hydrophobic medium is a drop of a hydrophobic medium.

15. A process for producing a droplet assembly according to claim 14 wherein the drop of the hydrophobic medium is within a second bulk medium which is an aqueous medium, wherein the container of the apparatus contains said second bulk medium which is an aqueous medium and the drop of hydrophobic medium, and the drop of the hydrophobic medium further comprises a peripheral layer of amphipathic molecules around the surface of the drop, as an interface between the drop and the second bulk medium.

16. A process according to claim 12 wherein the first and second aqueous media comprise different concentrations of a salt or buffer.

17. A process according to claim 12 wherein the first aqueous medium comprises a membrane protein and the second aqueous medium does not comprise said membrane protein.

18. A process according to claim 12 wherein the droplet or droplets of the first aqueous medium, which are dispensed by the first droplet generator, have a different size from the droplet or droplets of the second aqueous medium, which are dispensed by the second droplet generator.

19. A process according to claim 1 wherein the droplets are dispensed at a rate of at least $1\ s^{-1}$.

20. A process according to claim 1 wherein the droplets are dispensed at a rate of at least $1\ s^{-1}$, n is equal to or greater than 500, and each droplet dispensed from the droplet generator has a volume of less than 100 nL.

21. A process for producing a droplet assembly using an apparatus for producing the droplet assembly,
which droplet assembly comprises: a plurality of droplets, wherein each of said droplets comprises: (i) a droplet medium, and (ii) an outer layer of amphipathic molecules around the surface of the droplet medium, wherein the droplet medium is an aqueous medium or a hydrophobic medium, and wherein each of said droplets contacts another of said droplets to form a bilayer of said amphipathic molecules as an interface between the contacting droplets wherein the droplet assembly comprises at least n of said droplets, and at least n−1 of said interfaces between contacting droplets, wherein n is equal to or greater than 500;
which apparatus comprises: at least one droplet generator; a container which is moveable relative to the at least one droplet generator; and a control unit, which control unit is adapted to control the dispensing of droplets from the at least one droplet generator and the movement of the container relative to the at least one droplet generator;
wherein said container of the apparatus contains a bulk medium, wherein:
when the droplet medium is an aqueous medium the bulk medium is a hydrophobic medium, and when the droplet medium is a hydrophobic medium the bulk medium is an aqueous medium;
which process comprises:
 (a) at least n dispensing steps, wherein each dispensing step comprises dispensing a droplet of the droplet medium which has a volume of less than 100 nL from a said droplet generator into the bulk medium, in the presence of amphipathic molecules, and thereby forming in the bulk medium a droplet which comprises (i) said droplet medium and (ii) an outer layer of amphipathic molecules around the surface of the droplet medium; and
 (b) between the dispensing steps, or between and during the dispensing steps, moving the container relative to the at least one droplet generator, to control the relative positioning of the droplets in the bulk medium and to position each droplet adjacent to at least one other droplet, so that each of said droplets contacts another of said droplets to form a bilayer of said amphipathic molecules as an interface between contacting droplets,
wherein the control unit coordinates the dispensing steps, and the movement of the container relative to the at least one droplet generator, to produce the droplet assembly, and the droplets are dispensed at a rate of at least $0.5\ s^{-1}$.

22. A process according to claim 21 wherein each droplet dispensed from the droplet generator has a volume of less than or equal to 0.5 nL.

23. A process according to claim 21 wherein each droplet dispensed from the droplet generator has a diameter of equal to or less than 200 μm.

24. A process for producing a droplet assembly using an apparatus for producing the droplet assembly,
which droplet assembly comprises: a plurality of droplets, wherein each of said droplets comprises: (i) a droplet medium, and (ii) an outer layer of amphipathic molecules around the surface of the droplet medium, wherein the droplet medium is an aqueous medium or a hydrophobic medium, and wherein each of said droplets contacts another of said droplets to form a bilayer of said amphipathic molecules as an interface between the contacting droplets wherein the droplet assembly comprises at least n of said droplets, and at least n−1 of said interfaces between contacting droplets, wherein n is equal to or greater than 500;
which apparatus comprises: at least one droplet generator; a container which is moveable relative to the at least one droplet generator; and a control unit, which control unit is adapted to control the dispensing of droplets from the at least one droplet generator and the movement of the container relative to the at least one droplet generator;

wherein said container of the apparatus contains a bulk medium, wherein:

when the droplet medium is an aqueous medium the bulk medium is a hydrophobic medium, and when the droplet medium is a hydrophobic medium the bulk medium is an aqueous medium;

which process comprises:
- (a) at least n dispensing steps, wherein each dispensing step comprises dispensing a droplet of the droplet medium which has a volume of less than 100 nL from a said droplet generator into the bulk medium, in the presence of amphipathic molecules, and thereby forming in the bulk medium a droplet which comprises (i) said droplet medium and (ii) an outer layer of amphipathic molecules around the surface of the droplet medium, wherein each droplet is dispensed from said droplet generator into the bulk medium when a tip of the droplet generator is immersed in said bulk medium; and
- (b) between the dispensing steps, or between and during the dispensing steps, moving the container relative to the at least one droplet generator, to control the relative positioning of the droplets in the bulk medium and to position each droplet adjacent to at least one other droplet, so that each of said droplets contacts another of said droplets to form a bilayer of said amphipathic molecules as an interface between contacting droplets, wherein the control unit coordinates the dispensing steps, and the movement of the container relative to the at least one droplet generator, to produce the droplet assembly, and the droplets are dispensed at a rate of at least $0.5\ s^{-1}$.

25. A process according to claim 24 wherein each droplet dispensed from the droplet generator has a volume of less than or equal to 0.5 nL.

26. A process according to claim 24 wherein the droplets are dispensed at a rate of at least $1\ s^{-1}$.

27. A process according to claim 24 wherein each droplet dispensed from the droplet generator has a volume of less than or equal to 0.5 nL and the droplets are dispensed at a rate of at least $1\ s^{-1}$.

28. A process according to claim 24 wherein each droplet dispensed from the droplet generator has a volume of less than or equal to 0.5 nL and n is equal to or greater than 1000.

29. A process according to claim 24 wherein each droplet dispensed from the droplet generator has a diameter of equal to or less than 200 μm and the droplets are dispensed at a rate of at least $1\ s^{-1}$.

* * * * *